(12) United States Patent
Muehlebach et al.

(10) Patent No.: US 8,084,474 B2
(45) Date of Patent: Dec. 27, 2011

(54) INSECTICIDES

(75) Inventors: Michel Muehlebach, Basel (CH); Andre Jeanguenat, Basel (CH); Roger Graham Hall, Basel (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 800 days.

(21) Appl. No.: 12/160,794

(22) PCT Filed: Jan. 15, 2007

(86) PCT No.: PCT/EP2007/000302
§ 371 (c)(1),
(2), (4) Date: Jul. 14, 2008

(87) PCT Pub. No.: WO2007/080131
PCT Pub. Date: Jul. 19, 2007

(65) Prior Publication Data
US 2010/0168066 A1    Jul. 1, 2010

(30) Foreign Application Priority Data

Jan. 16, 2006  (EP) .................................... 06000826
Feb. 13, 2006  (EP) .................................... 06002803

(51) Int. Cl.
*A61K 31/4439*   (2006.01)
*C07D 401/04*    (2006.01)
(52) U.S. Cl. ..................................... 514/341; 546/275.4
(58) Field of Classification Search .................. 514/341; 546/275.4
See application file for complete search history.

(56) References Cited

FOREIGN PATENT DOCUMENTS
| WO | 0170671    | 9/2001 |
| WO | 03015518   | 2/2003 |
| WO | 2006055922 | 5/2006 |

OTHER PUBLICATIONS

Unterhaltb et al: "Synthese thiaanaloger Cyclamate—Synthesis of Thia-analogous Cyclamates"; Archiv Der Pharmazie, VCH Verlagsgesellshaft MFBH, Weinheim, DE, vol. 323, 1990, pp. 317-318, XP007903047 ISSN: 0365-6233, p. 317, col. 2, paragraph 4.

Diggle, A.W. et al: "Pathways in fission of strained rings;" Bulletin De La Societe Chimique De France, 1988, p. 317-321, XP009090142, compound 10A.

Romvrdowska M.D.: "Synthesis of (2S, 3S)-3-Amino-2-Phenylthietane" Tetrahedron: Asymmetry, Pergamon, Oxford, GB., vol. 5, No. 7, 1994, pp. 1327-1332, XP007903048, ISSN: 0957-4166, compound 6.

Frigola J et al: "7-Azetidinylquinolones as Antibacterial Agents. 3. Synthesis, Properties and Structure-Activity Relationships of the Stereoisomers Containing a 7-(3-Amino-2-methyl-1-azetidinyl) Moiety"; Journal of Medicinal Chemistry, American Chemical Society, Washington, US, vol. 38, No. 7, 1995, pp. 1203-1215, XP002115345, ISSN: 0022-2623, compounds 18A-19D.

Kuramoto Y et al: "A Novel Antibacterial 8-Chloroquinolone with a Distorted Orientation of the N1-(5-Amino-2,4-diflurophenyl) Group"; Journal of Medicinal Chemistry American Chemical Society, Washington, US, vol. 46, No. 10, Sep. 4, 2003, pp. 1905-1917, XP007903053, ISSN: 0022-2623, figures 4, 5.

Grzegorz Mloston et al: "Ring Opening of 1-AzabicycloA1.1. OUbutanes with Hydrazoic Acid a Facile Access to N-Unsubstituted Azetidin-3-Amines;" Helvetica Chimica Acta, Verlag Helvetica Chimica Acta, Basel, CH, vol. 88, Mar. 1, 2005, pp. 1658-1663, XP007903054, ISSN: 0018-019X, compounds 4A-4D.

Baum K. et al: "Synthesis of Electron-Deficient Oxetanes, and 3,3-Dinitroxetane"; Journal of Organic Chemistry, American Chemical Society, Easton, US, vol. 48, No. 18, Sep. 9, 1983, pp. 2953-2956, XP000602197, ISSN: 0022-3263, figure 2.

*Primary Examiner* — Taofiq A Solola
(74) *Attorney, Agent, or Firm* — Rebecca Howard

(57) ABSTRACT

Compounds of formula (I) wherein the substituents are as defined in claim (1), and the agrochemically acceptable salts and all stereoisomers and tautomeric forms of the compounds of formula (I) can be used as agrochemical active ingredients and can be prepared in a manner known per se.

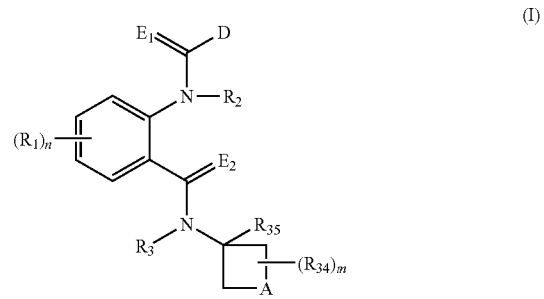

19 Claims, No Drawings

INSECTICIDES

"This application is a 371 of International Application No. PCT/EP2007/000302 filed Jan. 15, 2007, which claims priority to EP 06000826.5 filed Jan. 16, 2006, and EP 06002803.2 filed Feb. 13, 2006, the contents of which are incorporated herein by reference."

The present invention relates to novel anthranilamide derivatives, to processes for their preparation, to compositions comprising those compounds, and to their use for controlling insects or representatives of the order Acarina.

Anthranilamide derivatives with insecticidal properties are known and described, for example, in WO 03/015518 or WO 2006/055922. There have now been found novel anthranilamide derivatives with pesticidal properties, especially for the control of insects and members of the order Acarina. The novel compounds are characterised by a 4-membered, saturated heterocyclic ring attached to the aminocarbonyl substituent of the phenyl ring.

The present invention accordingly relates to compounds of formula I

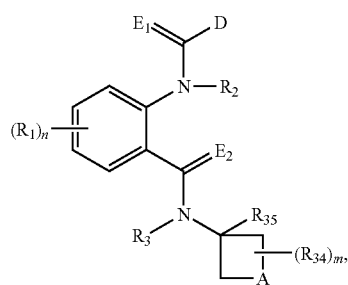

(I)

wherein

D is phenyl, 2-pyridyl, 3-pyridyl or 4-pyridyl; or phenyl, 2-pyridyl, 3-pyridyl or 4-pyridyl mono-, di- or trisubstituted by $C_1$-$C_6$alkyl, $C_3$-$C_6$cycloalkyl, $C_1$-$C_6$haloalkyl, halogen, cyano, $C_1$-$C_4$alkoxy, $C_1$-$C_4$haloalkoxy, $C_1$-$C_4$alkylthio, $C_1$-$C_4$haloalkylthio, $C_1$-$C_4$alkylsulfiny, $C_1$-$C_4$alkylsulfonyl, $C_1$-$C_4$haloalkylsulfinyl or $C_1$-$C_4$haloalkylsulfonyl;

or D is a group

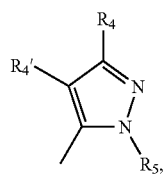

(D₁)

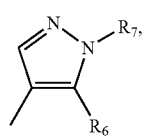

(D₂)

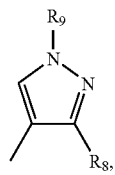

(D₃)

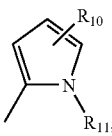

(D₄)

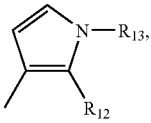

(D₅)

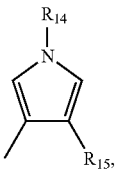

(D₆)

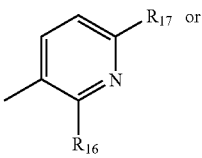

(D₇) or

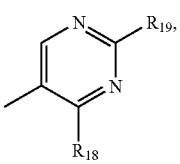

(D₈)

$R_4$, $R_4'$, and $R_{10}$ independently from each other, are hydrogen, $C_1$-$C_6$alkyl, $C_3$-$C_6$cycloalkyl, $C_1$-$C_6$haloalkyl, halogen, cyano, $C_1$-$C_4$alkoxy, $C_1$-$C_4$haloalkoxy, $C_2$-$C_4$alkoxycarbonyl, $C_1$-$C_4$alkylthio, $C_1$-$C_4$haloalkylthio, $C_1$-$C_4$alkylsulfinyl, $C_1$-$C_4$alkylsulfonyl, $C_1$-$C_4$haloalkylsulfinyl or $C_1$-$C_4$haloalkylsulfonyl;

$R_5$, $R_6$, $R_8$, $R_{11}$, $R_{12}$, $R_{15}$ independently from each other, are $C_1$-$C_6$alkyl, or $C_1$-$C_6$alkyl mono-, di- or trisubstituted by halogen, cyano, nitro, hydroxy, $C_1$-$C_4$alkoxy, $C_2$-$C_4$alkoxycarbonyl, $C_1$-$C_4$alkylthio, $C_1$-$C_4$alkylsulfinyl, $C_1$-$C_4$alkylsulfonyl, $C_1$-$C_4$alkylamino, $C_2$-$C_4$dialkylamino or $C_3$-$C_6$cycloalkylamino; or are phenyl, 2-pyridyl, 3-pyridyl, 4-pyridyl; or are phenyl, 2-pyridyl, 3-pyridyl or 4-pyridyl mono-, di- or trisubstituted by $C_1$-$C_6$alkyl, $C_3$-$C_6$cycloalkyl, $C_1$-$C_6$haloalkyl, halogen, cyano, $C_1$-$C_4$alkoxy, $C_1$-$C_4$haloalkoxy, $C_1$-$C_4$alkylthio, $C_1$-$C_4$haloalkylthio, $C_1$-$C_4$alkylsulfinyl, $C_1$-$C_4$alkylsulfonyl, $C_1$-$C_4$haloalkylsulfinyl or $C_1$-$C_4$haloalkylsulfonyl;

$R_7$, $R_9$, $R_{13}$ and $R_{14}$ independently from each other, are hydrogen, $C_1$-$C_6$alkyl, $C_1$-$C_6$haloalkyl, $C_2$-$C_6$alkenyl, $C_2$-$C_6$haloalkenyl, $C_3$-$C_6$alkenyl or $C_3$-$C_6$haloalkenyl;

each $R_1$ independently is halogen, nitro, cyano, hydroxy, $C_1$-$C_6$alkyl, $C_2$-$C_6$alkenyl, $C_2$-$C_6$alkynyl, $C_3$-$C_6$cycloalkyl, $C_1$-$C_6$haloalkyl, $C_2$-$C_6$haloalkenyl, $C_2$-$C_6$haloalkynyl, $C_3$-$C_6$halocycloalkyl, $C_1$-$C_4$alkoxy, $C_1$-$C_4$haloalkoxy, $C_1$-$C_4$alkylthio, $C_1$-$C_4$haloalkylthio, $C_1$-$C_4$haloalkylsulfinyl, $C_1$-$C_4$haloalkylsulfonyl, $C_1$-$C_4$alkylsulfinyl, $C_1$-$C_4$alkylsulfonyl, $C_1$-$C_4$alkylamino, $C_2$-$C_4$dialkylamino, $C_3$-$C_6$cycloalkylamino, $C_1$-$C_6$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, $C_3$-$C_6$dialkylaminocarbonyl, $C_2$-$C_6$alkoxycarbonyloxy, $C_2$-$C_6$alkylaminocarbonyloxy, $C_3$-$C_6$dialkylaminocarbonyloxy or $C_3$-$C_6$trialkylsilyl, phenyl, benzyl or phenoxy, or phenyl, benzyl or phenoxy mono-, di- or trisubstituted by halogen, cyano, nitro, halogen, $C_1$-$C_6$alkyl, $C_2$-$C_6$alkenyl, $C_2$-$C_6$alkynyl, $C_3$-$C_6$cycloalkyl, $C_1$-$C_6$haloalkyl, $C_2$-$C_6$haloalkenyl, $C_2$-$C_6$haloalkynyl, $C_3$-$C_6$halocycloalkyl, $C_1$-$C_4$alkoxy, $C_1$-$C_4$haloalkoxy, $C_1$-$C_4$alkylthio, $C_1$-$C_4$haloalkylthio, $C_1$-$C_4$alkylsulfinyl, $C_1$-$C_4$alkylsulfonyl, $C_1$-$C_4$alkylamino, $C_2$-C4dialkylamino, $C_3$-$C_6$cycloalkylamino, $C_1$-$C_6$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, $C_3$-$C_6$dialkylaminocarbonyl, $C_2$-$C_6$alkoxycarbonyloxy, $C_2$-$C_6$alkylaminocarbonyloxy, $C_3$-$C_6$dialkylaminocarbonyloxy or $C_3$-$C_6$trialkylsilyl;

n is 0, 1, 2 or 3;

each of $R_2$ and $R_3$, which may be the same or different, represents hydrogen, $C_1$-$C_6$alky, $C_2$-$C_6$alkenyl, $C_2$-$C_6$alkynyl or $C_3$-$C_8$cycloalkyl; or $C_1$-$C_6$alkyl, $C_2$-$C_6$alkenyl, $C_2$-$C_6$alkynyl or $C_3$-$C_8$cycloalkyl substituted by one or more substituents selected from halogen nitro, cyano, hydroxy, $C_1$-$C_4$alkoxy, $C_1$-$C_4$haloalkoxy, $C_1$-$C_4$alkylthio, $C_1$-$C_4$haloalkylthio, $C_1$-$C_4$alkylsulfinyl, $C_1$-$C_4$alkylsulfonyl, $C_1$-$C_4$alkylamino, $C_2$-$C_4$dialkylamino, $C_3$-$C_6$cycloalkylamino and $C_1$-$C_6$alkyl-$C_3$-$C_6$cycloalkylamino;

each of $E_1$ and $E_2$, which may be the same or different, represents oxygen or sulfur;

A is oxygen, sulfur, SO, $SO_2$, $S(O)_p$=N—R, C=N—$OR_{36}$, N—$R_0$, C=O or $P(X)_t$—$R_{33}$;

$R_{33}$ is hydrogen, $C_1$-$C_6$alkyl, $C_2$-$C_6$alkenyl, $C_2$-$C_6$alkynyl, $C_1$-$C_6$haloalkyl, $C_1$-$C_6$alkoxy, hydroxy, $C_3$-$C_6$cycloalkyl, $C_3$-$C_6$cycloalkyl-$C_1$-$C_6$alkyl, benzyl or phenyl; where phenyl and benzyl for their part may be mono- di- or trisubstituted by $C_1$-$C_6$alkyl, $C_1$-$C_8$haloalkyl, halogen, cyano or nitro; or $R_{33}$ is $O^-Na^+$, $O^-Li^+$, or $O^-K^+$;

$R_{36}$ is hydrogen, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, $C_1$-$C_6$alkoxy-$C_1$-$C_6$alkyl, $C_1$-$C_6$haloalkoxy-$C_1$-$C_6$alkyl or benzyl;

X is oxygen or sulfur;

p is 0 or 1;

t is 0 or 1;

each of $R_{34}$ and $R_{35}$, which may be the same or different, represents hydrogen, COOH, halogen, nitro, cyano, hydroxy, $C_1$-$C_6$alkyl, $C_1$-$C_6$haloalkyl, $C_2$-$C_6$alkenyl, $C_2$-$C_6$alkynyl, $C_2$-$C_6$haloalkenyl, $C_2$-$C_6$haloalkynyl, $C_1$-$C_6$alkylthio, $C_1$-$C_6$alkylsulfinyl, $C_1$-$C_6$alkylsulfonyl, $C_1$-$C_6$haloalkylthio, $C_1$-$C_6$haloalkylsulfinyl, $C_1$-$C_6$haloalkylsulfonyl, $C_1$-$C_6$alkoxycarbonyl, $C_1$-$C_6$alkylcarbonyl, $C_3$-$C_6$alkylaminocarbonyl, $C_3$-$C_6$dialkylaminocarbonyl, $C_1$-$C_6$alkoxy-$C_1$-$C_6$alkyl, $C_1$-$C_6$haloalkoxy-$C_1$-$C_6$alkyl, $C_1$-$C_6$alkoxy, $C_1$-$C_6$haloalkoxy, $C_1$-$C_6$alkylamino, $C_2$-$C_6$dialkylamino, $C_3$-$C_6$trialkylsilyl, benzyl or phenyl; where phenyl and benzyl for their part may be mono- di- or trisubstituted by $C_1$-$C_6$alkyl, $C_1$-$C_6$haloalkyl, $C_1$-$C_6$alkoxy, $C_1$-$C_6$haloalkoxy, halogen, cyano, hydroxyl or nitro;

m is 0, 1, 2, 3 or 4;

R is hydrogen, $C_1$-$C_6$alkyl, $C_1$-$C_6$haloalkyl, $C_3$-$C_6$cycloalkyl, $C_3$-$C_6$halocycloalkyl, $C_1$-$C_6$alkylthio, $C_1$-$C_6$haloalkylthio, $C_1$-$C_6$alkoxy-$C_1$-$C_6$alkyl or $C_1$-$C_6$haloalkoxy-$C_1$-$C_6$alkyl; or R is $C_1$-$C_6$alkyl, $C_1$-$C_6$haloalkyl, $C_3$-$C_6$cycloalkyl, $C_3$-$C_6$halocycloalkyl, $C_1$-$C_6$alkylthio, $C_1$-$C_6$haloalkylthio, $C_1$-$C_6$alkoxy-$C_1$-$C_6$alkyl or $C_1$-$C_6$haloalkoxy-$C_1$-$C_6$alkyl substituted by $C_1$-$C_6$alkyl, $C_1$-$C_6$haloalkyl, $C_3$-$C_6$cycloalkyl, $C_3$-$C_6$halocycloalkyl, $C_1$-$C_6$alkoxy, or $C_1$-$C_6$haloalkoxy, or $C_1$-$C_6$haloalkoxy; or R is cyano, nitro, —$C(O)R_{26}$, —$C(O)OR_{27}$, —$CONR_{28}R_{29}$, —$SO_2R_{30}$ or —$P(O)(OR_{31})(OR_{32})$;

$R_0$ is hydrogen, $C_1$-$C_6$alkyl, $C_1$-$C_6$haloalkyl, $C_3$-$C_6$cycloalkyl, $C_3$-$C_6$halocycloalkyl, $C_1$-$C_6$alkylthio, $C_1$-$C_6$haloalkylthio, $C_1$-$C_6$alkoxy-$C_1$-$C_6$alkyl or $C_1$-$C_6$haloalkoxy-$C_1$-$C_6$alkyl; or $R_0$ is $C_1$-$C_6$alkyl, $C_1$-$C_6$haloalkyl, $C_3$-$C_6$cycloalkyl, $C_3$-$C_6$halocycloalkyl, $C_1$-$C_6$alkylthio, $C_1$-$C_6$haloalkylthio, $C_1$-$C_6$alkoxy-$C_1$-$C_6$alkyl or $C_1$-$C_6$haloalkoxy-$C_1$-$C_6$alkyl substituted by $C_1$-$C_6$alkyl, $C_1$-$C_6$haloalkyl, $C_3$-$C_6$cycloalkyl, $C_3$-$C_6$halocycloalkyl, $C_1$-$C_6$alkoxy, or $C_1$-$C_6$haloalkoxy; or $R_0$ is cyano, nitro, —$C(O)R_{026}$, —$C(O)OR_{027}$, —$CONR_{028}R_{029}$, —$SO_2R_{030}$ or —$P(O)(OR_{031})(OR_{032})$; or $R_0$ is phenyl or benzyl, or phenyl or benzyl mono-, di- or trisubstituted by substituents selected from $C_1$-$C_6$alkyl, $C_3$-$C_6$cycloalkyl, $C_1$-$C_6$haloalkyl, halogen, cyano, $C_1$-$C_4$alkoxy, $C_1$-$C_4$haloalkoxy, $C_1$-$C_4$alkylthio, $C_1$-$C_4$haloalkylthio, $C_1$-$C_4$alkylsulfinyl, $C_1$-$C_4$alkylsulfonyl, $C_1$-$C_4$haloalkylsulfinyl and $C_1$-$C_4$haloalkylsulfonyl;

each of $R_{26}$ and $R_{026}$, which may be the same or different, represents hydrogen, $C_1$-$C_6$alkyl, $C_1$-$C_6$haloalkyl, $C_3$-$C_6$cycloalkyl, $C_1$-$C_6$halocycloalkyl, $C_1$-$C_6$alkylthio, $C_1$-$C_6$haloalkylthio, $C_1$-$C_6$alkoxycarbonyl, $C_1$-$C_6$alkylcarbonyl or $C_1$-$C_6$alkoxy-$C_1$-$C_6$alkyl; or $C_1$-$C_6$alkyl, $C_1$-$C_6$haloalkyl, $C_3$-$C_6$cycloalkyl, $C_3$-$C_6$halocycloalkyl, $C_1$-$C_6$alkylthio, $C_1$-$C_6$haloalkylthio, $C_1$-$C_6$alkoxycarbonyl, $C_1$-$C_6$alkylcarbonyl or $C_1$-$C_6$alkoxy-$C_1$-$C_6$alkyl substituted by $C_1$-$C_6$alkyl, $C_1$-$C_6$haloalkyl, $C_3$-$C_6$cycloalkyl, $C_3$-$C_6$halocycloalkyl, $C_1$-$C_6$alkoxy, or $C_1$-$C_6$haloalkoxy;

each of $R_{27}$, $R_{28}$, $R_{29}$, $R_{38}$, $R_{31}$, $R_{32}$, $R_{027}$, $R_{028}$, $R_{029}$, $R_{030}$, $R_{031}$ and $R_{032}$ which may be the same or different, represents $C_1$-$C_6$alkyl, $C_1$-$C_6$haloalkyl, $C_3$-$C_6$cycloalkyl or $C_3$-$C_6$halocycloalkyl; or $C_1$-$C_6$alkyl, $C_1$-$C_6$haloalkyl, $C_3$-$C_6$cycloalkyl or $C_1$-$C_6$halocycloalkyl substituted by $C_1$-$C_6$alkyl, $C_1$-$C_6$haloalkyl, $C_3$-$C_6$cycloalkyl, $C_3$-$C_6$halocycloalkyl, $C_1$-$C_6$alkoxy or $C_1$-$C_6$haloalkoxy;

with the proviso that $E_1$ or $E_2$ is sulfur if A is oxygen, sulfur or N—$R_0$, wherein $R_0$ is hydrogen, $C_1$-$C_3$alkyl, $C_1$-$C_3$haloalkyl, $C_2$-$C_4$alkylcarbonyl, $C_2$-$C_4$haloalkylcarbonyl, $C_2$-$C_4$alkoxycarbonyl or $C_1$-$C_3$alkylsulfonyl;

and agronomically acceptable salts/isomers/diastereomers/enantiomers/tautomers/N-oxides of those compounds.

Compounds of formula I which have at least one basic centre can form, for example, acid addition salts, for example with strong inorganic acids such as mineral acids, for example perchloric acid, sulfuric acid, nitric acid, nitrose acid, a phosphorus acid or a hydrohalic acid, with strong organic carboxylic acids, such as $C_1$-$C_4$alkanecarboxylic acids which are unsubstituted or substituted, for example by halogen, for example acetic acid, such as saturated or unsaturated dicarboxylic acids, for example oxalic acid, malonic acid, succinic acid, maleic acid, fumaric acid or phthalic acid, such as hydroxycarboxylic acids, for example ascorbic acid, lactic acid, malic acid, tartaric acid or citric acid, or such as benzoic acid, or with organic sulfonic acids, such as $C_1$-$C_4$alkane- or arylsulfonic acids which are unsubstituted or substituted, for example by halogen, for example methane- or p-toluene-sulfonic acid. Compounds I which have at least one acidic group can form, for example, salts with bases, for example mineral salts such as alkali metal or alkaline earth metal salts, for example sodium, potassium or magnesium salts, or salts with ammonia or an organic amine, such as morpholine, piperidine, pyrrolidine, a mono-, di- or tri-lower-alkylamine, for example ethyl-, diethyl-, triethyl- or dimethylpropy-lamine, or a mono-, di- or trihydroxy-lower-alkylamine, for example mono-, di- or triethanolamine. Where appropriate, the corresponding internal salts can furthermore be formed.

Preferred within the scope of the invention are agrochemically advantageous salts; however, the invention also encompasses salts which have disadvantage for agrochemical use, for example salts which are toxic to bees or fish, and which are employed, for example, for the isolation or purification of free compounds of formula I or agrochemically utilizable salts thereof. Owing to the close relationship between the compounds of formula I in free form and in the form of their salts, for the purposes of the invention the free compounds of formula I or their salts hereinabove and hereinbelow are respectively to be understood as including, where appropriate, the corresponding salts or the free compounds of formula I. The same applies analogously to tautomers of compounds of formula I and salts thereof. In general, the free form is preferred in each case.

The alkyl groups occurring in the definitions of the substituents can be straight-chain or branched and are, for example, methyl, ethyl, n-propyl, isopropyl, n-butyl, sec-butyl, iso-butyl, tert-butyl, pentyl, hexyl, heptyl and octyl and their branched isomers. Alkoxy, alkenyl and alkynyl radicals are derived from the alkyl radicals mentioned. The alkenyl and alkynyl groups can be mono- or polyunsaturated.

Halogen is generally fluorine, chlorine, bromine or iodine. This also applies, correspondingly, to halogen in combination with other meanings, such as haloalkyl or halophenyl.

Haloalkyl groups preferably have a chain length of from 1 to 6 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl; preferably trichloro-methyl, difluorochloromethyl, difluoromethyl, trifluoromethyl and dichlorofluoromethyl.

Suitable haloalkenyl groups are alkenyl groups which are mono- or polysubstituted by halogen, halogen being fluorine, chlorine, bromine and iodine and in particular fluorine and chlorine, for example 2,2-difluoro-1-methylvinyl, 3-fluoropropenyl, 3-chloropropenyl, 3-bromopropenyl, 2,3,3-trifluoropropenyl, 2,3,3-trichloropropenyl and 4,4,4-trifluorobut-2-en-1-yl. Among the alkenyl groups which are mono-, di- or trisubstituted by halogen, preference is given to those having a chain length of from 3 to 5 carbon atoms.

Suitable haloalkynyl groups are, for example, alkynyl groups which are mono- or polysubstituted by halogen, halogen being bromine, iodine and in particular fluorine and chlorine, for example 3-fluoropropynyl, 3-chloropropynyl, 3-bromopropynyl, 3,3,3-trifluoro-propynyl and 4,4,4-trifluorobut-2-yn-1-yl. Among the alkynyl groups which are mono- or polysubstituted by halogen, preference is given to those having a chain length of from 3 to 5 carbon atoms.

Alkoxy groups preferably have a preferred chain length of from 1 to 6 carbon atoms. Alkoxy is, for example, methoxy, ethoxy, propoxy, i-propoxy, n-butoxy, isobutoxy, sec-butoxy and tert-butoxy and also the isomeric pentyloxy and hexyloxy radicals; preferably methoxy and ethoxy.

Alkoxycarbonyl is, for example, methoxycarbonyl, ethoxycarbonyl, propoxycarbonyl, isopropoxycarbonyl, n-butoxycarbonyl, isobutoxycarbonyl, sec-butoxycarbonyl or tert-butoxycarbonyl; preferably methoxycarbonyl or ethoxycarbonyl. Haloalkoxy groups preferably have a chain length of from 1 to 6 carbon atoms. Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy and 2,2,2-trichloroethoxy; preferably difluoromethoxy, 2-chloroethoxy and trifluoromethoxy. Alkylthio groups preferably have a chain length of from 1 to 6 carbon atoms. Alkylthio is, for example, methylthio, ethylthio, propylthio, isopropylthio, n-butylthio, isobutylthio, sec-butylthio or tert-butylthio, preferably methylthio and ethylthio. Alkylsulfinyl is, for example, methylsulfinyl, ethylsulfinyl, propylsulfinyl, isopropylsulfinyl, n-butylsulfinyl, isobutylsulfinyl, sec-butylsulfinyl, tert-butylsulfinyl; preferably methylsulfinyl and ethylsulfinyl.

Alkylsulfonyl is, for example, methylsulfonyl, ethylsulfonyl, propylsulfonyl, isopropylsulfonyl, n-butylsulfonyl, isobutylsulfonyl, sec-butylsulfonyl or tert-butylsulfonyl; preferably methylsulfonyl or ethylsulfonyl. Alkoxyalkoxy groups preferably have a chain length of from 1 to 8 carbon atoms. Examples of alkoxyalkoxy groups are: methoxymethoxy, methoxyethoxy, methoxypropoxy, ethoxymethoxy, ethoxyethoxy, propoxymethoxy or butoxybutoxy. Alkylamino is, for example, methylamino, ethylamino, n-propylamino, isopropylamino or the isomeric butylamines. Dialkylamino is, for example, dimethylamino, methylethylamino, diethylamino, n-propylmethylamino, dibutylamino and diisopropylamino. Preference is given to alkylamino groups having a chain length of from 1 to 4 carbon atoms. Alkoxyalkyl groups preferably have a chain length of 1 to 6 carbon atoms. Alkoxyalkyl is, for example, methoxymethyl, methoxyethyl, ethoxymethyl, ethoxyethyl, n-propoxymethyl, n-propoxyethyl, isopropoxymethyl or isopropoxyethyl. Alkylthioalkyl groups preferably have from 1 to 8 carbon atoms. Alkylthioalkyl is, for example, methylthiomethyl, methylthioethyl, ethylthiomethyl, ethylthioethyl, n-propylthiomethyl, n-propylthioethyl, isopropylthiomethyl, isopropylthioethyl, butylthiomethyl, butylthioethyl or butylthiobutyl. The cycloalkyl groups preferably have from 3 to 6 ring carbon atoms, for example cyclopropyl, cyclobutyl, cyclopentyl and cyclohexyl. Phenyl, also as part of a substituent such as phenoxy, benzyl, benzyloxy, benzoyl, phenylthio, phenylalkyl, phenoxyalkyl, may be substituted. In this case, the substituents can be in ortho, meta and/or para position. The preferred substituent positions are the ortho and para positions to the ring attachment point.

$E_1$ and/or $E_2$ is preferably oxygen.

Preference is given to subgroups of compounds of formula I wherein
 a) $R_2$ is hydrogen or $C_1$-$C_4$alkyl; and/or
 b) $R_3$ is hydrogen or $C_1$-$C_4$alkyl; and/or
 c) D is a group $D_1$ and/or.
 d) $E_2$ is sulfur.

Further compounds of formula I are preferred, wherein A is N-benzyl, SO or $SO_2$, in particular SO or $SO_2$.

A preferred subgroup of compounds of formula I is represented by the compounds of formula Ia

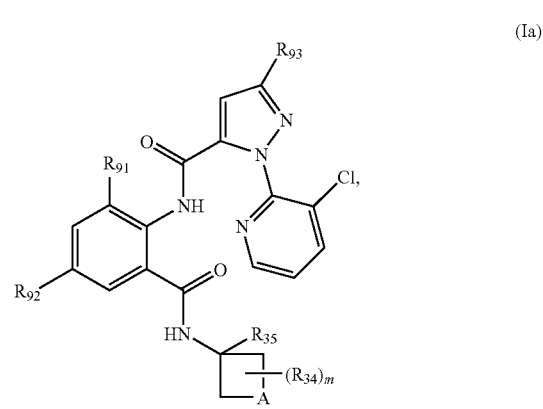

(Ia)

wherein $R_{91}$ is $C_1$-$C_4$alkyl or halogen, preferably chloro, bromo or methyl;

$R_{92}$ is halogen or cyano, preferably fluoro, chloro, bromo or cyano;

$R_{33}$ is halogen, $C_1$-$C_4$haloalkyl or $C_1$-$C_4$haloalkoxy; and

A, $R_{34}$ and $R_{35}$ and m have the meanings given under formula I.

In a preferred subgroup of compounds of formula I or of formula Ia, A is SO, SO$_2$, S(O)$_p$=N—R, C=N—OR$_{36}$, C=O, P(X)$_t$—R$_{33}$ or N—R$_0$; wherein p, t, X, R$_{33}$ and R$_{36}$ have the meanings given under formula I and $R_0$ is $C_3$-$C_6$cycloalkyl, $C_3$-$C_6$halocycloalkyl, $C_1$-$C_6$alkylthio, $C_1$-$C_6$haloalkylthio, $C_1$-$C_6$alkoxy-$C_1$-$C_6$alkyl or $C_1$-$C_6$haloalkoxy-$C_1$-$C_6$alkyl; or $R_0$ is $C_1$-$C_6$alkyl, $C_1$-$C_6$haloalkyl, $C_3$-$C_6$cycloalkyl, $C_3$-$C_6$halocycloalkyl, $C_1$-$C_6$alkylthio, $C_1$-$C_6$haloalkylthio, $C_1$-$C_6$alkoxy-$C_1$-$C_6$alkyl or $C_1$-$C_6$haloalkoxy-$C_1$-$C_6$alkyl substituted by $C_3$-$C_6$cycloalkyl, $C_3$-$C_6$halocycloalkyl, $C_1$-$C_6$alkoxy, or $C_1$-$C_6$haloalkoxy; or $R_0$ is cyano, nitro, —CONR$_{028}$R$_{029}$ or —P(O)(OR$_{031}$)(OR$_{032}$) wherein R$_{028}$, R$_{029}$, R$_{031}$ and R$_{032}$ have the meanings given under formula I, or $R_0$ is phenyl or benzyl, or phenyl or benzyl mono-, di- or trisubstituted by substituents selected from $C_1$-$C_6$alkyl, $C_3$-$C_6$cycloalkyl, $C_1$-$C_6$haloalkyl, halogen, cyano, $C_1$-$C_4$alkoxy, $C_1$-$C_4$haloalkoxy, $C_1$-$C_4$alkylthio, $C_1$-$C_4$haloalkylthio, $C_1$-$C_4$alkylsulfinyl, $C_1$-$C_4$alkylsulfonyl, $C_1$-$C_4$haloalkylsulfinyl and $C_1$-$C_4$haloalkylsulfonyl.

In a further preferred subgroup of compounds of formula I or of formula Ia, A is SO, SO$_2$, S(O)$_p$=N—R, C=N—OR$_{36}$, C=O, P(X)$_t$—R$_{33}$ or N—R$_0$; wherein p, t, X, R$_{33}$ and R$_{36}$ have the meanings given under formula I and $R_0$ is $C_3$-$C_6$cycloalkyl, $C_3$-$C_6$halocycloalkyl, $C_1$-$C_6$alkylthio, $C_1$-$C_6$haloalkylthio, $C_1$-$C_6$alkoxy-$C_1$-$C_6$alkyl or $C_1$-$C_6$haloalkoxy-$C_1$-$C_6$alkyl; or $R_0$ is $C_1$-$C_6$alkyl, $C_1$-$C_6$haloalkyl, $C_3$-$C_6$cycloalkyl, $C_3$-$C_6$halocycloalkyl, $C_1$-$C_6$alkylthio, $C_1$-$C_6$haloalkylthio, $C_1$-$C_6$alkoxy-$C_1$-$C_6$alkyl or $C_1$-$C_6$haloalkoxy-$C_1$-$C_6$alkyl substituted by $C_3$-$C_6$cycloalkyl, $C_3$-$C_6$halocycloalkyl, $C_1$-$C_6$alkoxy, or $C_1$-$C_6$haloalkoxy; or $R_0$ is cyano, nitro, —CONR$_{028}$R$_{029}$ or —P(O)(OR$_{031}$)(OR$_{032}$) wherein R$_{028}$, R$_{029}$, R$_{031}$ and R$_{032}$ have the meanings formula I.

Special emphasis should also be given to compounds of formula I wherein e) $R_{34}$ is hydrogen or $C_1$-$C_4$alkyl, preferably hydrogen or methyl; and/or f) $R_{35}$ is hydrogen or $C_1$-$C_4$alkyl, preferably hydrogen or methyl; and/or g) A is oxygen, sulfur, SO, SO$_2$, S=NR or S(O)$_p$=NR, preferably S, SO, SO$_2$ or S(O)$_p$=NR, wherein p is 1; most preferably oxygen or sulfur; and/or h) R is hydrogen, cyano, nitro, —C(O)R$_{26}$, —C(O)OR$_{27}$, —CONR$_{28}$R$_{29}$, —SO$_2$R$_{30}$ or —P(O)(OR$_{31}$)(OR$_{32}$), preferably hydrogen, cyano, —COOMe, —SO$_2$Me or —C(O)CF$_3$ and/or i) $R_0$ is hydrogen, cyano, nitro, —C(O)R$_{026}$, —C(O)OR$_{027}$, —CONR$_{028}$R$_{029}$, —SO$_2$R$_{030}$ or —P(O)(OR$_{031}$)(OR$_{032}$), preferably hydrogen, cyano, —COOMe, —SO$_2$Me or —C(O)CF$_3$ and/or j) $R_4$' is different from hydrogen.

"Me" represents the methyl group.

In preferred compounds of formula I, $R_{26}$ is hydrogen, $C_1$-$C_6$alkyl, $C_1$-$C_6$haloalkyl or $C_3$-$C_6$cycloalkyl. In preferred compounds of formula I, R$_{27}$, R$_{28}$, R$_{29}$, R$_{30}$, R$_{31}$ and R$_{32}$ independently of one another are $C_1$-$C_6$alkyl or $C_1$-$C_6$haloalkyl; or $C_1$-$C_6$alkyl or $C_1$-$C_6$haloalkyl substituted with $C_1$-$C_6$alkyl or $C_1$-$C_6$haloalkyl.

In preferred compounds of formula I, $R_{026}$ is hydrogen, $C_1$-$C_6$alkyl, $C_1$-$C_6$haloalkyl or $C_3$-$C_6$cycloalkyl. In preferred compounds of formula I, R$_{027}$, R$_{028}$, R$_{029}$, R$_{030}$, R$_{031}$ and R$_{032}$ independently of one another are $C_1$-$C_6$alkyl or $C_1$-$C_6$haloalkyl; or $C_1$-$C_6$alkyl or $C_1$-$C_6$haloalkyl substituted with $C_1$-$C_6$alkyl or $C_1$-$C_6$haloalkyl.

The process according to the invention for preparing compounds of the formula I or, where appropriate, a tautomer and/or salt thereof, is carried out analogously to known processes, for example those described in WO 01/70671, WO 03/016284, WO 03/015518 and WO 04/033468.

The process for the preparation of a compound of the formula I, or, when appropriate, a tautomer thereof, in each case in free form or in salt form, comprises, for example, a) to prepare a compound of formula I, in which $R_2$ is hydrogen and $E_1$ and $E_2$ are oxygen, or, where appropriate, a tautomer and/or salt thereof, by reacting a compound of formula II

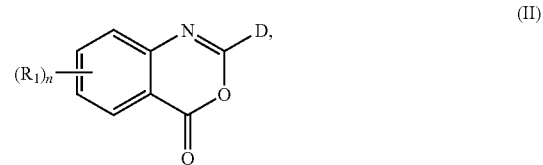

in which R$_1$, n, and D have the meanings given for formula I, or, where appropriate, a tautomer and/or salt thereof with a compound of formula III

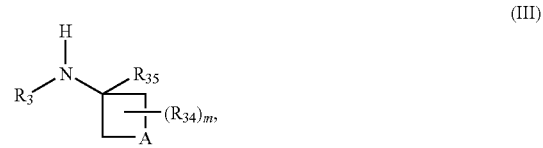

in which A, R$_3$, R$_{34}$, R$_{35}$ and m have the meanings given for the formula I, or, where appropriate, with a tautomer and/or salt thereof or, b) to prepare a compound of formula I, or, where appropriate, a tautomer and/or salt thereof, reacting a compound of formula IV

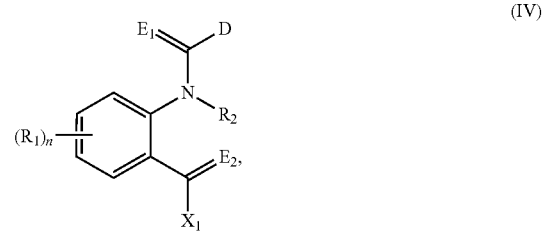

in which R$_1$, R$_2$, n, E$_1$, E$_2$ and D have the meanings given for the formula I; and X$_1$ is a leaving group, or, where appropriate, a tautomer and/or salt thereof with a compound of formula III

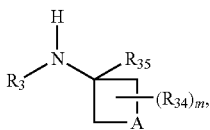

in which A, $R_3$, $R_{34}$, $R_{35}$ and m have the meanings given for formula I, or, where appropriate, with a tautomer and/or salt thereof or, c) to prepare a compound of formula I, or, where appropriate, a tautomer and/or salt thereof, by reacting a compound of formula V

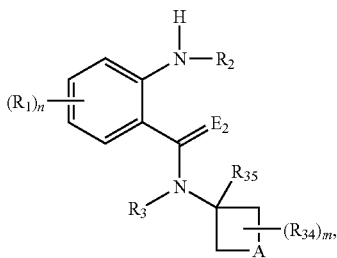

in which n, $R_1$, $R_2$, $R_3$, $E_2$, $R_{34}$, $R_{35}$, A and m have the meanings given for formula I, or, where appropriate, a tautomer and/or salt thereof with a compound of formula VI $$X_2C(=E_1)D \quad (VI),$$

in which $E_1$ and D have the meanings given for formula I; and $X_2$ is a leaving group, or, where appropriate, with a tautomer and/or salt thereof and/or converting a compound of formula I or, where appropriate, a tautomer thereof, in each case in free form or in salt form, into another compound of formula I or, where appropriate, a tautomer thereof, separating an isomer mixture, which can be obtained in accordance with the process, and isolating the desired isomer and/or converting a free compound of formula I or, where appropriate, a tautomer thereof into a salt or a salt of a compound of formula I or, where appropriate, a tautomer thereof into the free compound of formula I or, where appropriate, a tautomer thereof or into another salt.

The compounds of formula II are described in WO 04/111030. The compounds of formula III and V are novel and especially developed for the preparation of the compounds of formula I and constitute therefore a further embodiment of the present invention. The preferences for the substituents of formula I mentioned above are also valid for the compounds of formula III and V.

In especially preferred compounds of formula III
$R_3$ is hydrogen;
$R_{34}$ is hydrogen or $C_1$-$C_4$alkyl, preferably hydrogen or methyl;
$R_{35}$ is hydrogen, halogen, cyano, $C_1$-$C_4$alkyl, $C_1$-$C_4$haloalkyl, $C_1$-$C_4$alkoxycarbonyl, $C_1$-$C_4$alkoxy-$C_1$-$C_4$alkyl, $C_1$-$C_4$haloalkoxy-$C_1$-$C_4$alkyl;
A is oxygen, sulfur, SO, $SO_2$, S=NR or $S(O)_p$=NR, preferably S, SO, $SO_2$ or $S(O)_p$=NR, wherein p is 1 and wherein R is hydrogen, cyano, nitro, —C(O)$R_{26}$, —C(O)O$R_{27}$, —CON$R_{28}R_{29}$, —$SO_2R_{30}$ or —P(O)(O$R_{31}$)(O$R_{32}$), preferably hydrogen, cyano, —COOMe, —$SO_2$Me or —C(O)CF$_3$;
m is 0,1,2,3 or 4.

In especially preferred compounds of formula V
$R_1$ is $C_1$-$C_4$alkyl, halogen, $C_1$-$C_5$haloalkyl, cyano, nitro, $C_1$-$C_4$alkoxy, $C_1$-$C_4$-haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl or $C_1$-$C_4$haloalkylsulfonyl;
$R_2$ and $R_3$ are hydrogen;
$E_2$ is oxygen or sulfur;
$R_{34}$ is hydrogen or $C_1$-$C_4$alkyl, preferably hydrogen or methyl; $R_{35}$ is hydrogen, halogen, cyano, $C_1$-$C_4$alkyl, $C_1$-$C_4$haloalkyl, $C_1$-$C_4$alkoxycarbonyl, $C_1$-$C_4$alkoxy-$C_1$-$C_4$alkyl, $C_1$-$C_4$haloalkoxy-$C_1$-$C_6$alkyl;
A is oxygen, sulfur, SO, $SO_2$, S=NR or $S(O)_p$=NR, preferably S, SO, $SO_2$ or $S(O)_p$=NR, wherein p is 1 and wherein R is hydrogen, cyano, nitro, —C(O)$R_{26}$, —C(O)O$R_{27}$, —CON$R_{28}R_{29}$, —$SO_2R_{30}$ or —P(O)(O$R_{31}$)(O$R_{32}$), preferably hydrogen, cyano, —COOMe, —$SO_2$Me or —C(O)CF$_3$;
m is 0, 1, 2, 3 or 4.
n is 1, 2 or 3.

TABLE C

Preferred compounds of formula III represented by the formula IIIa:

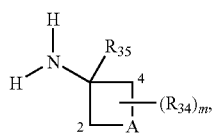

| Cmpd No. | A | $R_{34}$ | $R_{35}$ |
|---|---|---|---|
| C1 | O | H | H |
| C2 | O | H | CH$_3$ |
| C3 | O | H | CH$_2$OCH$_3$ |
| C4 | O | H | CF$_3$ |
| C5 | O | 2,2-diMe | H |
| C6 | O | 2,2-diMe | CH$_3$ |
| C7 | O | 2,2,4,4-tetraMe | H |
| C8 | O | 2,2,4,4-tetraMe | CH$_3$ |
| C9 | S | H | H |
| C10 | S | H | CH$_3$ |
| C11 | S | H | CH$_2$OCH$_3$ |
| C12 | S | H | CF$_3$ |
| C13 | S | 2,2-diMe | H |
| C14 | S | 2,2-diMe | CH$_3$ |
| C15 | S | 2,2,4,4-tetraMe | H |
| C16 | S | 2,2,4,4-tetraMe | CH$_3$ |
| C17 | SO | H | H |
| C18 | SO | H | CH$_3$ |
| C19 | SO | H | CH$_2$OCH$_3$ |
| C20 | SO | H | CF$_3$ |
| C21 | SO | 2,2-diMe | H |
| C22 | SO | 2,2-diMe | CH$_3$ |
| C23 | SO | 2,2,4,4-tetraMe | H |
| C24 | SO | 2,2,4,4-tetraMe | CH$_3$ |
| C25 | SO$_2$ | H | H |
| C26 | SO$_2$ | H | CH$_3$ |
| C27 | SO$_2$ | H | CH$_2$OCH$_3$ |
| C28 | SO$_2$ | H | CF$_3$ |
| C29 | SO$_2$ | 2,2-diMe | H |
| C30 | SO$_2$ | 2,2-diMe | CH$_3$ |
| C31 | SO$_2$ | 2,2,4,4-tetraMe | H |
| C32 | SO$_2$ | 2,2,4,4-tetraMe | CH$_3$ |
| C33 | S(O)NH | H | H |
| C34 | S(O)NH | H | CH$_3$ |
| C35 | S(O)NH | H | CH$_2$OCH$_3$ |
| C36 | S(O)NH | H | CF$_3$ |
| C37 | S(O)NH | 2,2-diMe | H |
| C38 | S(O)NH | 2,2-diMe | CH$_3$ |
| C39 | S(O)NH | 2,2,4,4-tetraMe | H |
| C40 | S(O)NH | 2,2,4,4-tetraMe | CH$_3$ |
| C41 | N—CH$_2$—C$_6$H$_5$ | H | H |
| C42 | N—CH$_2$—C$_6$H$_5$ | H | CH$_3$ |
| C43 | N—CH$_2$—C$_6$H$_5$ | H | CH$_2$OCH$_3$ |
| C44 | N—CH$_2$—C$_6$H$_5$ | H | CF$_3$ |

TABLE C-continued

Preferred compounds of formula III represented by the formula IIIa:

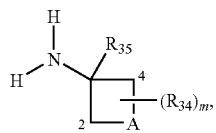
(IIIa)

| Cmpd No. | A | $R_{34}$ | $R_{35}$ |
|---|---|---|---|
| C45 | N—CH$_2$—C$_6$H$_5$ | 2,2-diMe | H |
| C46 | N—CH$_2$—C$_6$H$_5$ | 2,2-diMe | CH$_3$ |
| C47 | N—CH$_2$—C$_6$H$_5$ | 2,2,4,4-tetraMe | H |
| C48 | N—CH$_2$—C$_6$H$_5$ | 2,2,4,4-tetraMe | CH$_3$ |

TABLE D

Preferred compounds of formula V represented by formula Vb where $E_2$ is oxygen

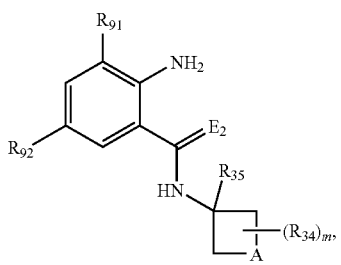
(Vb)

| Cmpd No. | $R_{91}$ | $R_{92}$ | A | $R_{34}$ | $R_{35}$ |
|---|---|---|---|---|---|
| D1 | Me | Cl | O | H | H |
| D2 | Me | Cl | O | H | CH$_3$ |
| D3 | Me | Cl | O | 2,2-diMe | H |
| D4 | Me | Cl | O | 2,2,4,4-tetraMe | H |
| D5 | Me | Br | O | H | H |
| D6 | Me | Br | O | H | CH$_3$ |
| D7 | Me | NO$_2$ | O | H | H |
| D8 | Me | NO$_2$ | O | H | CH$_3$ |
| D9 | Me | CN | O | H | H |
| D10 | Me | CN | O | H | CH$_3$ |
| D11 | Me | CN | O | 2,2-diMe | H |
| D12 | Me | CN | O | 2,2,4,4-tetraMe | H |
| D13 | Me | Cl | S | H | H |
| D14 | Me | Cl | S | H | CH$_3$ |
| D15 | Me | Cl | S | H | CH$_2$OCH$_3$ |
| D16 | Me | Cl | S | H | CF$_3$ |
| D17 | Me | Cl | S | 2,2-diMe | H |
| D18 | Me | Cl | S | 2,2-diMe | CH$_3$ |
| D19 | Me | Cl | S | 2,2,4,4-tetraMe | H |
| D20 | Me | Cl | S | 2,2,4,4-tetraMe | CH$_3$ |
| D21 | Me | Br | S | H | H |
| D22 | Me | Br | S | H | CH$_3$ |
| D23 | Me | NO$_2$ | S | H | H |
| D24 | Me | NO$_2$ | S | H | CH$_3$ |
| D25 | Me | CN | S | H | H |
| D26 | Me | CN | S | H | CH$_3$ |
| D27 | Me | CN | S | H | CH$_2$OCH$_3$ |
| D28 | Me | CN | S | H | CF$_3$ |
| D29 | Me | CN | S | 2,2-diMe | H |
| D30 | Me | CN | S | 2,2-diMe | CH$_3$ |
| D31 | Me | CN | S | 2,2,4,4-tetraMe | H |
| D32 | Me | CN | S | 2,2,4,4-tetraMe | CH$_3$ |
| D33 | Me | Cl | SO | H | H |
| D34 | Me | Cl | SO | H | CH$_3$ |
| D35 | Me | Cl | SO | H | CH$_2$OCH$_3$ |
| D36 | Me | Cl | SO | H | CF$_3$ |
| D37 | Me | Cl | SO | 2,2-diMe | H |
| D38 | Me | Cl | SO | 2,2-diMe | CH$_3$ |
| D39 | Me | Cl | SO | 2,2,4,4-tetraMe | H |
| D40 | Me | Cl | SO | 2,2,4,4-tetraMe | CH$_3$ |
| D41 | Me | Br | SO | H | H |
| D42 | Me | Br | SO | H | CH$_3$ |
| D43 | Me | NO$_2$ | SO | H | H |
| D44 | Me | NO$_2$ | SO | H | CH$_3$ |
| D45 | Me | CN | SO | H | H |
| D46 | Me | CN | SO | H | CH$_3$ |
| D47 | Me | CN | SO | H | CH$_2$OCH$_3$ |
| D48 | Me | CN | SO | H | CF$_3$ |
| D49 | Me | CN | SO | 2,2-diMe | H |
| D50 | Me | CN | SO | 2,2-diMe | CH$_3$ |
| D51 | Me | CN | SO | 2,2,4,4-tetraMe | H |
| D52 | Me | CN | SO | 2,2,4,4-tetraMe | CH$_3$ |
| D53 | Me | Cl | SO$_2$ | H | H |
| D54 | Me | Cl | SO$_2$ | H | CH$_3$ |
| D55 | Me | Cl | SO$_2$ | H | CH$_2$OCH$_3$ |
| D56 | Me | Cl | SO$_2$ | H | CF$_3$ |
| D57 | Me | Cl | SO$_2$ | 2,2-diMe | H |
| D58 | Me | Cl | SO$_2$ | 2,2-diMe | CH$_3$ |
| D59 | Me | Cl | SO$_2$ | 2,2,4,4-tetraMe | H |
| D60 | Me | Cl | SO$_2$ | 2,2,4,4-tetraMe | CH$_3$ |
| D61 | Me | Br | SO$_2$ | H | H |
| D62 | Me | Br | SO$_2$ | H | CH$_3$ |
| D63 | Me | NO$_2$ | SO$_2$ | H | H |
| D64 | Me | NO$_2$ | SO$_2$ | H | CH$_3$ |
| D65 | Me | CN | SO$_2$ | H | H |
| D66 | Me | CN | SO$_2$ | H | CH$_3$ |
| D67 | Me | CN | SO$_2$ | H | CH$_2$OCH$_3$ |
| D68 | Me | CN | SO$_2$ | H | CF$_3$ |
| D69 | Me | CN | SO$_2$ | 2,2-diMe | H |
| D70 | Me | CN | SO$_2$ | 2,2-diMe | CH$_3$ |
| D71 | Me | CN | SO$_2$ | 2,2,4,4-tetraMe | H |
| D72 | Me | CN | SO$_2$ | 2,2,4,4-tetraMe | CH$_3$ |
| D73 | Me | Cl | S(O)NH | H | H |
| D74 | Me | Cl | S(O)NH | H | CH$_3$ |
| D75 | Me | Cl | S(O)NH | H | CH$_2$OCH$_3$ |
| D76 | Me | Cl | S(O)NH | H | CF$_3$ |
| D77 | Me | Cl | S(O)NH | 2,2-diMe | H |
| D78 | Me | Cl | S(O)NH | 2,2-diMe | CH$_3$ |
| D79 | Me | Cl | S(O)NH | 2,2,4,4-tetraMe | H |
| D80 | Me | Cl | S(O)NH | 2,2,4,4-tetraMe | CH$_3$ |
| D81 | Me | Br | S(O)NH | H | H |
| D82 | Me | Br | S(O)NH | H | CH3 |
| D83 | Me | NO$_2$ | S(O)NH | H | H |
| D84 | Me | NO$_2$ | S(O)NH | H | CH$_3$ |
| D85 | Me | CN | S(O)NH | H | H |
| D86 | Me | CN | S(O)NH | H | CH$_3$ |
| D87 | Me | CN | S(O)NH | H | CH$_2$OCH$_3$ |
| D88 | Me | CN | S(O)NH | H | CF$_3$ |
| D89 | Me | CN | S(O)NH | 2,2-diMe | H |
| D90 | Me | CN | S(O)NH | 2,2-diMe | CH$_3$ |
| D91 | Me | CN | S(O)NH | 2,2,4,4-tetraMe | H |
| D92 | Me | CN | S(O)NH | 2,2,4,4-tetraMe | CH$_3$ |

TABLE G

Preferred compounds of formula V represented by formula Vb where $E_2$ is sulfur listing compounds G1 to G92 wherein $R_{91}$, $R_{92}$, A, $R_{34}$ and $R_{35}$ have the meanings given in Table D lines D1 to D92. Physical data for compounds of formula IIIa and Vb according to Tables C, D and G:

| Compound No. | melting point | $^1$H-NMR |
|---|---|---|
| C10 | liquid | CDCl$_3$: 3.25 (d, 2H), 3.04 (d, 2H), 1.78 (s, 2H), 1.53 (s, 3H). |
| C42 | oil | CDCl$_3$: 7.2 (m, 5H), 3.62 (s, 2H), 3.27 (d, 2H), 2.88 (d, 2H), 1.68 (bs, 2H), 1.4 (s, 3H). |
| C9, as hydrobromide salt | 186-190° C. | d$_6$-DMSO: 8.23 (br s, 3H), 4.52 (m, 1H), 3.47 (m, 2H), 3.18 (m, 2H). |
| C26, as trifluoroacetic acid salt | 208-210° C. | d$_6$-DMSO: 8.82 (br s, 3H), 4.56 (d, 2H), 4.29 (d, 2H), 1.68 (s, 3H). |
| C13 | oil | CDCl$_3$: 3.83 (dd, 1H), 3.19 (t, 1H), 2.95 (t, 1H), 1.63 (br s, 2H), 1.50 (s, 3H), 1.42 (s, 3H). |
| C54 | 79-82° C. | CDCl$_3$: 7.20 (s, 1H), 7.12 (s, 1H), 6.52 (s, 1H), 5.58 (br s, 2H), 4.64 (d, 2H), 4.15 (d, 2H), 2.13 (s, 3H), 1.87 (s, 3H). |
| D14 | 92-94° C. | CDCl$_3$: 7.14 (s, 1H), 7.10 (s, 1H), 6.09 (s, 1H), 5.57 (br s, 2H), 3.90 (d, 2H), 3.03 (d, 2H), 2.14 (s, 3H), 1.83 (s, 3H). |

Compounds of formula Va, a subgroup of compounds of formula V where $R_2$ is hydrogen, can be prepared for example in analogy to methods described in WO2001/070671.

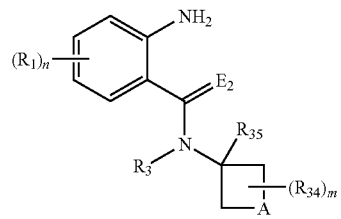

(Va)

The compounds of formula Va can also be prepared by reacting a compound of formula XI with a compound of formula III in the presence of a base and an inert solvent

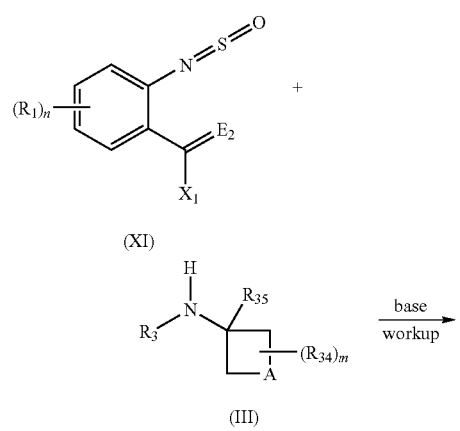

in which n, $R_1$, $R_3$, $E_2$, $R_{34}$, $R_{35}$, A and m have the meanings given in formula I; and $X_1$ is a leaving group (for example chlorine, bromine), or, where appropriate, a tautomer and/or salt thereof.

Suitable bases are for example N(C$_2$H$_5$)$_3$, DBU, DBN or imidazole. Preferred solvents are tetrahydrofurane, dioxane, glyme, ethyl acetate or toluene. The reaction is carried out at temperatures of from 0° C. to 100° C., preferably at +15° C. to +30° C. in particular at ambient temperature. A further process for the preparation of compounds of formula V is described in PCT/EP2006/003504.

Special emphasis should also be given to a subgroup of compounds of formula V represented by the compounds of formula Vb

(Vb)

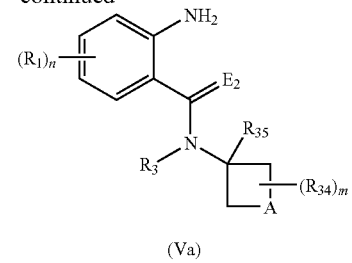

wherein $R_{91}$ is C$_1$-C$_4$alkyl or halogen, preferably chloro, bromo or methyl;

$R_{92}$ is halogen or cyano, preferably fluoro, chloro, bromo or cyano; and $E_2$, A, $R_{34}$, $R_{35}$ and m have the meanings given under formula I.

Amides of formula V/Va/Vb where $E_2$ is oxygen are readily converted to thioamides of formula V/Va/Vb where $E_2$ is sulfur by using commercially available thio transfer reagents such as phosphorus pentasulfide and Lawesson's reagent, for example in analogy to X. Fontrodona et al., Synthesis, 2001, (13), 2021-27.

Compounds of formula XI, in particular those compounds of formula XI where $X_1$ is chlorine, can be prepared for example in analogy to J. Garin et al., Tetrahedron Letters, 1991, 32, 3263-64.

Compounds of formula III are either known in the literature or can be prepared in analogy according to known methods.

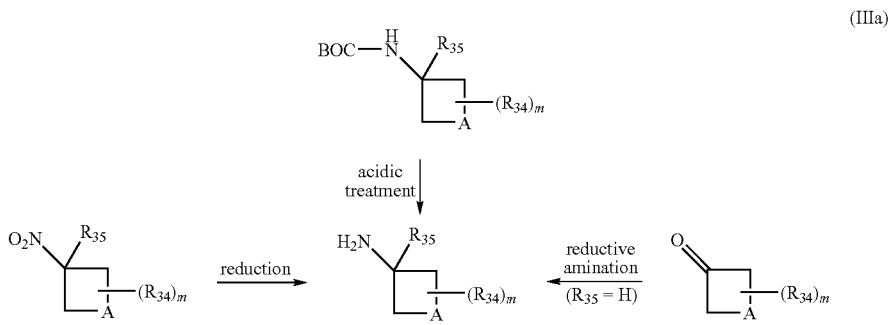

(IIIa)

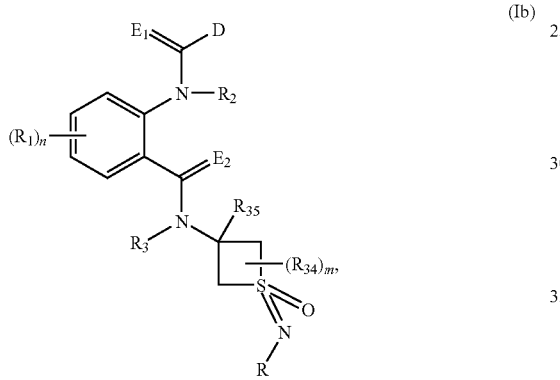

Compounds of formula IIIa, a subgroup of compounds of formula III where $R_3$ is hydrogen, can be prepared for example as described above via reduction, or via reductive amination, or via acidic treatment, or in further analogy according to known methods.

A subgroup of compounds of formula I represented by the compounds of formula Ib

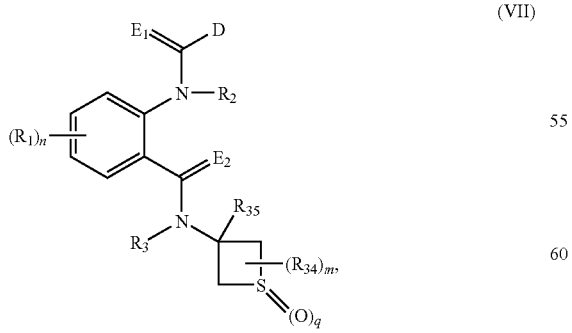

(Ib)

in which n, $R_1$, $R_2$, $R_3$, D, $E_1$, $E_2$, $R_{34}$, $R_{35}$, m and R have the meanings given in formula I, is prepared, for example, under similar conditions as described for a compound of formula I in variants a), b) or c), wherein the group A of formula I, III and V in variants a), b) or c) is replaced by the group $S(O)_p$=NR, wherein p is 1.

Alternatively, a compound of the formula Ib, or, where appropriate, a tautomer and/or salt thereof, in each case in free form or in salt form, is prepared, for example, from a compound of the formula (VII)

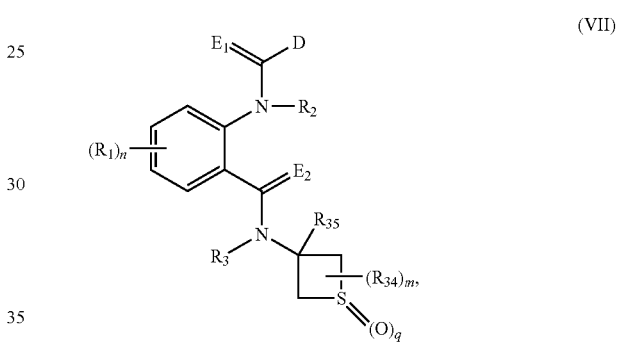

in which n, $R_1$, $R_2$, $R_3$, D, $E_1$, $E_2$, $R_{34}$, $R_{35}$ and m have the meanings given in formula I and q is 0 or 1, according to known procedures (H. Okamura, C. Bolm, Org. Lett. 2004, 6, 1305; H. Okamura, C. Bolm, Chem. Lett. 2004, 33, 482; D. Leca, K. Song, M. Amatore, L. Fensterbank, E. Lacote, M. Malacria, Chem. Eur. J. 2004, 10, 906) or as described below.

A compound of formula I or a compound of formula III, where the group A of formula I and III is replaced by the group $S(O)_p$=NR, wherein p is 1, are prepared, for example, from a compound of formula VII (VII)

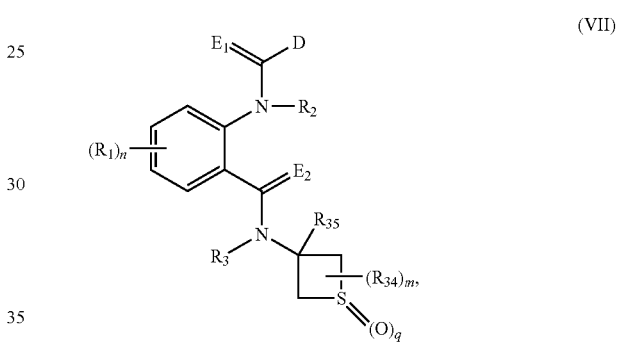

in which n, $R_1$, $R_2$, $R_3$, D, $E_1$, $E_2$, $R_{34}$, $R_{35}$ and m have the meanings given in formula I and q is 0 or 1, respectively from a compound of formula VIII (VIII)

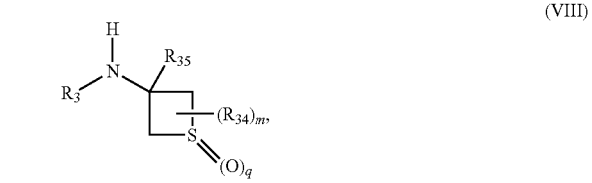

in which $R_3$, $R_{34}$, $R_{35}$ and m have the meanings given in the formula I and q is 0 or 1, according to known procedures (scheme 1: q=0: step A and then B; q=1: step B, see e.g. M. Reggelin, C. Zur, Synthesis, 2000, 1). The compounds of formulae III, V and VIII are novel, especially developed for the preparation of the compounds of formula I and therefore constitute a further object of the present invention.

Scheme 1

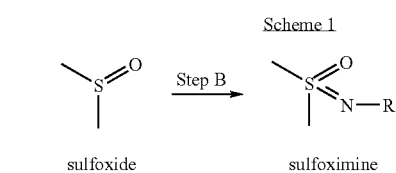

sulfoxide    sulfoximine

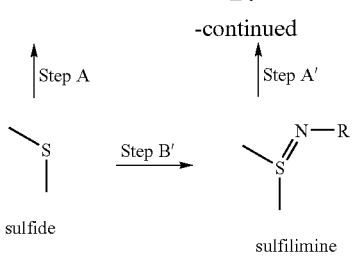

Alternatively, a compound of formula I or a compound of formula III, where the group A of formula I and III is replaced by the group $S(O)_p$=NR, wherein p is 1, are prepared, for example, from a compound of formula IX

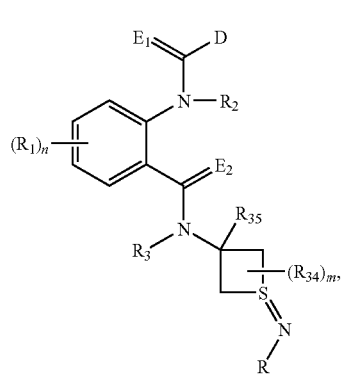

in which n, $R_1$, $R_2$, $R_3$, D, $E_1$, $E_2$, $R_{34}$, $R_{35}$, m and R have the meanings given in formula I, respectively from a compound of formula X

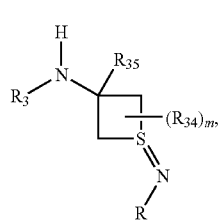

in which $R_3$, $R_{34}$, $R_{35}$, m and R have the meanings given in the formula I, according to known methods (scheme 1, step A'), wherein a compound of formula IX or a compound of formula X are prepared, for example, from a compound of formula VII (q=0) respectively from a compound of formula VIII (q=0) according to known methods, as described in scheme 1, step B'.

For the transformation of a sulfide to a sulfoxide or a sulfilimine to a sulfoximine (scheme 1, step A or A'), classical oxidation reagents are $KMnO_4$, mCPBA, $NaIO_4/RuO_2$, $H_2O_2$, oxone. For the transformation of a sulfoxide to a sulfoximine or a sulfide to a sulfilimine (scheme 1, step B or B'), typical reagents are $NaN_3/H_2SO_4$, O-mesitylenesulfonylhydroxylamine (MSH), or metal-catalyzed methods such as $RN_3/FeCl_2$, PhI=N—R/Cu(OTf)$_2$, PhI=N—R/Cu(OTf)$_2$, PhI=N—R/CuPF$_6$, PHI(OAc)$_2$/R—NH$_2$/MgO/Ru$_2$(OAc)$_4$ or oxaziridines (e.g. 3-(4-cyano-phenyl)-oxaziridine-2-carboxylic acid tert-butyl ester).

Detailed preparation conditions useful for the synthesis of compounds of formula Ib (preparation of sulfoximines) are given in WO2006/061200.

What has been said above for tautomers and/or salts of compounds of formula I applies analogously to starting materials mentioned hereinabove and hereinbelow with regard to the tautomers and/or salts thereof.

The reactions described hereinabove and hereinbelow are carried out in a manner known per se, for example in the absence or, normally, in the presence of a suitable solvent or diluent or of a mixture of these, the process being carried out, as required, with cooling, at room temperature or with heating, for example in a temperature range of from approximately −80° C. to the boiling point of the reaction mixture, preferably from approximately −20° C. to approximately +150° C., and, if required, in a sealed vessel, under reduced, normal or elevated pressure, in an inert gas atmosphere and/or under anhydrous conditions. Especially advantageous reaction conditions can be seen from the examples.

Unless otherwise specified, the starting materials mentioned hereinabove and hereinbelow, which are used for the preparation of the compounds of formula I or, where appropriate, the tautomers thereof, in each case in free form or in salt form, are known or can be prepared by methods known per se, for example in accordance with the information given below. The reactants can be reacted in the presence of a base. Examples of suitable bases for facilitating the detachment of $HX_2$ are alkali metal or alkaline earth metal hydroxides, alkali metal or alkaline earth metal hydrides, alkali metal or alkaline earth metal amides, alkali metal or alkaline earth metal alkoxides, alkali metal or alkaline earth metal acetates, alkali metal or alkaline earth metal carbonates, alkali metal or alkaline earth metal dialkylamides or alkali metal or alkaline earth metal alkylsilylamides, alkylamines, alkylenediamines, free or N-alkylated saturated or unsaturated cycloalkylamines, basic heterocycles, ammonium hydroxides and carbocyclic amines. Examples which may be mentioned are sodium hydroxide, sodium hydride, sodium amide, sodium methoxide, sodium acetate, sodium carbonate, potassium tert-butoxide, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,8-diazabicyclo[5.4.0]undec-7-ene (DBU).

The reactants can be reacted with each other as such, i.e. without adding a solvent or diluent. In most cases, however, it is advantageous to add an inert solvent or diluent or a mixture of these. If the reaction is carried out in the presence of a base, bases which are employed in excess, such as triethylamine, pyridine, N-methylmorpholine or N,N-diethylaniline, may also act as solvents or diluents.

The reaction is advantageously carried out in a temperature range from approximately −80° C. to approximately +140° C., preferably from approximately −30° C. to approximately +100° C., in many cases in the range between room temperature and approximately +80° C.

A compound of formula I can be converted in a manner known per se into another compound I by replacing one or more substituents of the starting compound of formula I in the customary manner by (an)other substituent(s) according to the invention.

Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

Salts of compounds of formula I can be prepared in a manner known per se. Thus, for example, acid addition salts of compounds of formula I are obtained by treatment with a suitable acid or a suitable ion exchanger reagent and salts with bases are obtained by treatment with a suitable base or with a suitable ion exchanger reagent.

Salts of compounds of formula I can be converted in the customary manner into the free compounds of formula I, acid addition salts, for example, by treatment with a suitable basic compound or with a suitable ion exchanger reagent and salts with bases, for example, by treatment with a suitable acid or with a suitable ion exchanger reagent.

Salts of compounds of formula I can be converted in a manner known per se into other salts of compounds of formula I, acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds of formula I, which have salt-forming properties can be obtained in free form or in the form of salts.

The compounds of formula I and, where appropriate, the tautomers thereof, in each case in free form or in salt form, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

Diastereomer mixtures or racemate mixtures of compounds of formula I, in free form or in salt form, which can be obtained depending on which starting materials and procedures have been chosen can be separated in a known manner into the pure diasteromers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl cellulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

It is advantageous to isolate or synthesize in each case the biologically more effective isomer, for example enantiomer or diastereomer, or isomer mixture, for example enantiomer mixture or diastereomer mixture, if the individual components have a different biological activity.

The compounds according to the invention and, where appropriate, the tautomers thereof, in each case in free form or in salt form, can, if appropriate, also be obtained in the form of hydrates and/or include other solvents, for example those which may have been used for the crystallization of compounds which are present in solid form.

The compounds according to the invention are preventively and/or curatively valuable active ingredients in the field of pest control, even at low rates of application, which have a very favorable biocidal spectrum and are well tolerated by warm-blooded species, fish and plants. The active ingredients according to the invention act against all or individual developmental stages of normally sensitive, but also resistant, animal pests, such as insects or representatives of the order Acarina. The insecticidal or acaricidal activity of the active ingredients according to the invention can manifest itself directly, i.e. in destruction of the pests, which takes place either immediately or only after some time has elapsed, for example during ecdysis, or indirectly, for example in a reduced oviposition and/or hatching rate, a good activity corresponding to a destruction rate (mortality) of at least 50 to 60%.

Examples of the abovementioned animal pests are:
from the order Acaria, for example,
*Acarus siro, Aceria sheldoni, Aculus schlechtendali, Amblyomma* spp., *Argas* spp., *Boophilus* spp., *Brevipalpus* spp., *Bryobia praetiosa, Calipitrimerus* spp., *Chorioptes* spp., *Dermanyssus gallinae, Eotetranychus carpini, Eriophyes* spp., *Hyalomma* spp., *Ixodes* spp., *Olygonychus pratensis, Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Tarsonemus* spp. and *Tetranychus* spp.;
from the order Anoplura, for example,
*Haematopinus* spp., *Linognathus* spp., *Pediculus* spp., *Pemphigus* spp. and *Phylloxera* spp.;
from the order Coleoptera, for example,
*Agriotes* spp., *Anthonomus* spp., *Atomaria linearis, Chaetocnema tibialis, Cosmopolites* spp., *Curculio* spp., *Dermestes* spp., *Diabrotica* spp., *Epilachna* spp., *Eremnus* spp., *Leptinotarsa decemlineata, Lissorhoptrus* spp., *Melolontha* spp., *Orycaephilus* spp., *Otiorhynchus* spp., *Phlyctinus* spp., *Popillia* spp., *Psylliodes* spp., *Rhizopertha* spp., *Scarabeidae, Sitophilus* spp., *Sitotroga* spp., *Tenebrio* spp., *Tribolium* spp. and *Trogoderma* spp.;
from the order Diptera, for example,
*Aedes* spp., *Antherigona soccata, Bibio hortulanus, Calliphora erythrocephala, Ceratitis* spp., *Chrysomyia* spp., *Culex* spp., *Cuterebra* spp., *Dacus* spp., *Drosophila melanogaster, Fannia* spp., *Gastrophilus* spp., *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit, Pegomyia hyoscyami, Phorbia* spp., *Rhagoletis pomonella, Sciara* spp., *Stomoxys* spp., *Tabanus* spp., *Tannia* spp. and *Tipula* spp.;
from the order Heteroptera, for example,
*Cimex* spp., *Distantiella theobroma, Dysdercus* spp., *Euchistus* spp., *Eurygaster* spp., *Leptocorisa* spp., *Nezara* spp., *Piesma* spp., *Rhodnius* spp., *Sahlbergella singularis, Scotinophara* spp. and *Triatoma* spp.;

from the order *Homoptera*, for example,

*Aleurothrixus floccosus, Aleyrodes brassicae, Aonidiella* spp., *Aphididae, Aphis* spp., *Aspidiotus* spp., *Bemisia tabaci, Ceroplaster* spp., *Chrysomphalus aonidium, Chrysomphalus dictyospermi, Coccus hesperidum, Empoasca* spp., *Eriosoma larigerum, Erythroneura* spp., *Gascardia* spp., *Laodelphax* spp., *Lecanium corni, Lepidosaphes* spp., *Macrosiphus* spp., *Myzus* spp., *Nephotettix* spp., *Nilaparvata* spp., *Parlatoria* spp., *Pemphigus* spp., *Planococcus* spp., *Pseudaulacaspis* spp., *Pseudococcus* spp., *Psylla* spp., *Pulvinaria aethiopica, Quadraspidiotus* spp., *Rhopalosiphum* spp., *Saissetia* spp., *Scaphoideus* spp., *Schizaphis* spp., *Sitobion* spp., *Trialeurodes vaporariorum, Trioza erytreae* and *Unaspis citri;* from the order *Hymenoptera*, for example,

*Acromyrmex, Atta* spp., *Cephus* spp., *Diprion* spp., *Diprionidae, Gilpinia polytoma, Hoplocampa* spp., *Lasius* spp., *Monomorium pharaonis, Neodiprion* spp., *Solenopsis* spp. and *Vespa* spp.;

from the order Isoptera, for example, *Reticulitermes* spp.;

from the order *Lepidoptera*, for example,

*Acleris* spp., *Adoxophyes* spp., *Aegeria* spp., *Agrotis* spp., *Alabama argillaceae, Amylois* spp., *Anticarsia gemmatalis, Archips* spp., *Argyrotaenia* spp., *Autographa* spp., *Busseola fusca, Cadra cautella, Carposina nipponensis, Chilo* spp., *Choristoneura* spp., *Clysia ambiguella, Cnaphalocrocis* spp., *Cnephasia* spp., *Cochylis* spp., *Coleophora* spp., *Crocidolomia binotalis, Cryptophlebia leucotreta, Cydia* spp., *Diatraea* spp., *Diparopsis castanea, Earias* spp., *Ephestia* spp., *Eucosma* spp., *Eupoecilia ambiguella, Euproctis* spp., *Euxoa* spp., *Grapholita* spp., *Hedya nubiferana, Heliothis* spp., *Hellula undalis, Hyphantria cunea, Keiferia lycopersicella, Leucoptera scitella, Lithocollethis* spp., *Lobesia botrana, Lymantria* spp., *Lyonetia* spp., *Malacosoma* spp., *Mamestra brassicae, Manduca sexta, Operophtera* spp., *Ostrinia nubilalis, Pammene* spp., *Pandemis* spp., *Panolis flammea, Pectinophora gossypiela, Phthorimaea operculella, Pieris rapae, Pieris* spp., *Plutella xylostella, Prays* spp., *Scirpophaga* spp., *Sesamia* spp., *Sparganothis* spp., *Spodoptera* spp., *Synanthedon* spp., *Thaumetopoea* spp., *Tortrix* spp., *Trichoplusia ni* and *Yponomeuta* spp.;

from the order Mallophaga, for example,

*Damalinea* spp. and *Trichodectes* spp.;

from the order Orthoptera, for example,

*Blatta* spp., *Blattella* spp., *Gryllotalpa* spp., *Leucophaea maderae, Locusta* spp., *Periplaneta* spp. and *Schistocerca* spp.;

from the order Psocoptera, for example,

*Liposcelis* spp.;

from the order *Siphonaptera*, for example,

*Ceratophyllus* spp., *Ctenocephalides* spp. and *Xenopsylla cheopis;* from the order Thysanoptera, for example,

*Frankliniella* spp., *Hercinothrips* spp., *Scirtothrips aurantii, Taeniothrips* spp., *Thrips palmi* and *Thrips tabaci;* and from the order Thysanura, for example,

*Lepisma saccharine.*

The active ingredients according to the invention can be used for controlling, i. e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family, latex plants and ornamentals.

The active ingredients according to the invention are especially suitable for controlling *Aphis craccivora, Diabrotica balteata, Heliothis virescens, Myzus persicae, Plutella xylostella* and *Spodoptera littoralis* in cotton, vegetable, maize, rice and soya crops. The active ingredients according to the invention are further especially suitable for controlling Mamestra (preferably in vegetables), *Cydia pomonella* (preferably in apples), *Empoasca* (preferably in vegetables, vineyards), *Leptinotarsa* (preferably in potatos) and *Chilo supressalis* (preferably in rice).

The term "crops" is to be understood as including also crops that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady® and LibertyLink®.

The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins, for example insecticidal proteins from *Bacillus cereus* or *Bacillus popliae*; or insecticidal proteins from *Bacillus thuringiensis*, such as δ-endotoxins, e.g. CryIA(b), CryIA(c), CryIF, CryIF(a2), CryIIA(b), CryIIIA, CryIIIB(b1) or Cry9c, or vegetative insecticidal proteins (VIP), e.g. VIP1, VIP2, VIP3 or VIP3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as *Streptomycetes* toxins, plant lectins, such as pea lectins, barley lectins or snowdrop lectins; agglutinins; proteinase inhibitors, such as trypsine inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example CryIA(b), CryIA (c), CryIF, CryIF(a2), CryIIA(b), CryIIIA, CryIIIB(b1) or Cry9c, or vegetative insecticidal proteins (VIP), for example VIP1, VIP2, VIP3 or VIP3A, expressly also hybrid toxins, truncated toxins and modified toxins. Hybrid toxins are produced recombinantly by a new combination of different domains of those proteins (see, for example, WO 02/15701). Truncated toxins, for example a truncated CryIA(b), are known. In the case of modified toxins, one or more amino acids of the naturally occurring toxin are replaced. In such amino acid replacements, preferably non-naturally present protease recognition sequences are inserted into the toxin, such as, for example, in the case of CryIIIA055, a cathepsin-D-recognition sequence is inserted into a CryIIIA toxin (see WO 03/018810).

Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. CryI-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (*Coleoptera*), two-winged insects (*Diptera*) and butterflies (*Lepidoptera*).

Transgenic plants containing one or more genes that code for an insecticidal resistance and express one or more toxins are known and some of them are commercially available. Examples of such plants are: YieldGard® (maize variety that expresses a CryIA(b) toxin); YieldGard Rootworm® (maize variety that expresses a CryIIIB(b1) toxin); YieldGard Plus® (maize variety that expresses a CryIA(b) and a CryIIIB(b1) toxin); Starlink® (maize variety that expresses a Cry9(c) toxin); Herculex I® (maize variety that expresses a CryIF(a2) toxin and the enzyme phosphinothricine N-acetyltransferase (PAT) to achieve tolerance to the herbicide glufosinate ammonium); NuCOTN 33B® (cotton variety that expresses a CryIA(c) toxin); Bollgard I® (cotton variety that expresses a CryIA(c) toxin); Bollgard II® (cotton variety that expresses a CryIA(c) and a CryIIA(b) toxin); VIPCOT® (cotton variety that expresses a VIP toxin); NewLeaf® (potato variety that expresses a CryIIIA toxin); Nature-Gard® Agrisure® GT Advantage (GA21 glyphosate-tolerant trait), Agrisure® CB Advantage (Bt11 corn borer (CB) trait) and Protecta®.

Further examples of such transgenic crops are:

1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated CryIA(b) toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a CryIA(b) toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified CryIIIA toxin. This toxin is Cry3A055 modified by insertion of a cathepsin-D-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9. MON 863 expresses a CryIIIB(b1) toxin and has resistance to certain Coleoptera insects.

5. IPC 531 Cotton from Monsanto Europe S.A. 270-272 Avenue de Tervuren, B-1150 Brussels, Belgium, registration number C/ES/96/02.

6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain *Lepidoptera* insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a CryIA(b) toxin obtained from *Bacillus thuringiensis* subsp. *kurstaki* which brings about tolerance to certain *Lepidoptera*, include the European corn borer.

Transgenic crops of insect-resistant plants are also described in BATS (Zentrum für Biosicherheit and Nachhaltigkeit, Zentrum BATS, Clarastrasse 13, 4058 Basel, Switzerland) Report 2003, (http://bats.ch).

The term "crops" is to be understood as including also crop plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818, and EP-A-0 353 191. The methods of producing such transgenic plants are generally known to the person skilled in the art and are described, for example, in the publications mentioned above.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defence (so-called "plant disease resistance genes", as described in WO 03/000906).

Further areas of use of the compounds according to the invention are the protection of stored goods and storerooms and the protection of raw materials, such as wood, textiles, floor coverings or buildings, and also in the hygiene sector, especially the protection of humans, domestic animals and productive livestock against pests of the mentioned type.

In the hygiene sector, the compounds according to the invention are active against ectoparasites such as hard ticks, soft ticks, mange mites, harvest mites, flies (biting and licking), parasitic fly larvae, lice, hair lice, bird lice and fleas.

Examples of such parasites are:

Of the order Anoplurida: *Haematopinus* spp., *Linognathus* spp., *Pediculus* spp. and *Phtirus* spp., *Solenopotes* spp.

Of the order Mallophagida: *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

Of the order Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

Of the order Siphonapterida, for example *Pulex* spp., *Ctenocephalides* spp., *Xenopsylla* spp., *Ceratophyllus* spp.

Of the order Heteropterida, for example *Cimex* spp., *Triatoma* spp., *Rhodnius* spp., *Panstrongylus* spp.

Of the order Blattarida, for example *Blatta orientalis*, *Periplaneta americana, Blattelagermanica* and *Supella* spp.

Of the subclass Acaria (Acarida) and the orders Meta- and Meso-stigmata, for example *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

Of the orders Actinedida (Prostigmata) and Acaridida (Astigmata), for example *Acarapis* spp., *Cheyletiella* spp., *Ornithocheyletia* spp., *Myobia* spp., *Psorergatesspp., Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The compounds according to the invention are also suitable for protecting against insect infestation in the case of materials such as wood, textiles, plastics, adhesives, glues, paints, paper and card, leather, floor coverings and buildings.

The invention therefore also relates to pesticidal compositions such as emulsifiable concentrates, suspension concentrates, directly sprayable or dilutable solutions, spreadable pastes, dilute emulsions, soluble powders, dispersible powders, wettable powders, dusts, granules or encapsulations in polymeric substances, which comprise—at least—one of the active ingredients according to the invention and which are to be selected to suit the intended aims and the prevailing circumstances.

In these compositions, the active ingredient is employed in pure form, a solid active ingredient for example in a specific particle size, or, preferably, together with—at least—one of the auxiliaries conventionally used in the art of formulation, such as extenders, for example solvents or solid carriers, or such as surface-active compounds (surfactants).

Examples of suitable solvents are: unhydrogenated or partially hydrogenated aromatic hydrocarbons, preferably the fractions $C_8$ to $C_{12}$ of alkylbenzenes, such as xylene mixtures, alkylated naphthalenes or tetrahydronaphthalene, aliphatic or cycloaliphatic hydrocarbons, such as paraffins or cyclohexane, alcohols such as ethanol, propanol or butanol, glycols and their ethers and esters such as propylene glycol, dipropylene glycol ether, ethylene glycol or ethylene glycol monomethyl ether or ethylene glycol monoethyl ether, ketones, such as cyclohexanone, isophorone or diacetone alcohol, strongly polar solvents, such as N-methylpyrrolid-2-one, dimethyl sulfoxide or N,N-dimethylformamide, water, unepoxidized or epoxidized vegetable oils, such as unexpodized or epoxidized rapeseed, castor, coconut or soya oil, and silicone oils.

Solid carriers which are used for example for dusts and dispersible powders are, as a rule, ground natural minerals such as calcite, talc, kaolin, montmorillonite or attapulgite. To improve the physical properties, it is also possible to add highly disperse silicas or highly disperse absorbtive polymers. Suitable particulate adsorptive carriers for granules are porous types, such as pumice, brick grit, sepiolite or bentonite, and suitable non-sorptive carrier materials are calcite or sand. In addition, a large number of granulated materials of inorganic or organic nature can be used, in particular dolomite or comminuted plant residues.

Suitable surface-active compounds are, depending on the type of the active ingredient to be formulated, non-ionic, cationic and/or anionic surfactants or surfactant mixtures which have good emulsifying, dispersing and wetting properties. The surfactants mentioned below are only to be considered as examples; a large number of further surfactants which are conventionally used in the art of formulation and suitable according to the invention are described in the relevant literature.

Suitable non-ionic surfactants are, especially, polyglycol ether derivatives of aliphatic or cycloaliphatic alcohols, of saturated or unsaturated fatty acids or of alkyl phenols which may contain approximately 3 to approximately 30 glycol ether groups and approximately 8 to approximately 20 carbon atoms in the (cyclo)aliphatic hydrocarbon radical or approximately 6 to approximately 18 carbon atoms in the alkyl moiety of the alkyl phenols. Also suitable are water-soluble polyethylene oxide adducts with polypropylene glycol, ethylenediaminopolypropylene glycol or alkyl polypropylene glycol having 1 to approximately 10 carbon atoms in the alkyl chain and approximately 20 to approximately 250 ethylene glycol ether groups and approximately 10 to approximately 100 propylene glycol ether groups. Normally, the abovementioned compounds contain 1 to approximately 5 ethylene glycol units per propylene glycol unit. Examples which may be mentioned are nonylphenoxypolyethoxyethanol, castor oil polyglycol ether, polypropylene glycol/polyethylene oxide adducts, tributylphenoxypolyethoxyethanol, polyethylene glycol or octylphenoxypolyethoxyethanol. Also suitable are fatty acid esters of polyoxyethylene sorbitan, such as polyoxyethylene sorbitan trioleate.

The cationic surfactants are, especially, quarternary ammonium salts which generally have at least one alkyl radical of approximately 8 to approximately 22 C atoms as substituents and as further substituents (unhalogenated or halogenated) lower alkyl or hydroxyalkyl or benzyl radicals. The salts are preferably in the form of halides, methylsulfates or ethylsulfates.

Examples are stearyltrimethylammonium chloride and benzylbis(2-chloroethyl)ethyl-ammonium bromide.

Examples of suitable anionic surfactants are water-soluble soaps or water-soluble synthetic surface-active compounds. Examples of suitable soaps are the alkali, alkaline earth or (unsubstituted or substituted) ammonium salts of fatty acids having approximately 10 to approximately 22 C atoms, such as the sodium or potassium salts of oleic or stearic acid, or of natural fatty acid mixtures which are obtainable for example from coconut or tall oil; mention must also be made of the fatty acid methyl taurates. However, synthetic surfactants are used more frequently, in particular fatty sulfonates, fatty sulfates, sulfonated benzimidazole derivatives or alkylaryl sulfonates. As a rule, the fatty sulfonates and fatty sulfates are present as alkali, alkaline earth or (substituted or unsubstituted) ammonium salts and they generally have an alkyl radical of approximately 8 to approximately 22 C atoms, alkyl also to be understood as including the alkyl moiety of acyl radicals; examples which may be mentioned are the sodium or calcium salts of lignosulfonic acid, of the dodecylsulfuric ester or of a fatty alcohol sulfate mixture prepared from natural fatty acids. This group also includes the salts of the sulfuric esters and sulfonic acids of fatty alcohol/ethylene oxide adducts. The sulfonated benzimidazole derivatives preferably contain 2 sulfonyl groups and a fatty acid radical of approximately 8 to approximately 22 C atoms. Examples of alkylarylsulfonates are the sodium, calcium or triethanolammonium salts of decylbenzenesulfonic acid, of dibutyl-naphthalenesulfonic acid or of a naphthalenesulfonic acid/formaldehyde condensate. Also possible are, furthermore, suitable phosphates, such as salts of the phosphoric ester of a p-nonylphenol/(4-14)ethylene oxide adduct, or phospholipids.

As a rule, the compositions comprise 0.1 to 99%, especially 0.1 to 95%, of active ingredient and 1 to 99.9%, especially 5 to 99.9%, of at least one solid or liquid adjuvant, it being possible as a rule for 0 to 25%, especially 0.1 to 20%, of the composition to be surfactants (% in each case meaning percent by weight). Whereas concentrated compositions tend to be preferred for commercial goods, the end consumer as a rule uses dilute compositions which have substantially lower concentrations of active ingredient. Preferred compositions are composed in particular as follows (%=percent by weight):

Emulsifiable Concentrates:

| active ingredient: | 1 to 95%, preferably 5 to 20% |
|---|---|
| surfactant: | 1 to 30%, preferably 10 to 20% |
| solvent: | 5 to 98%, preferably 70 to 85% |

Dusts:

| active ingredient: | 0.1 to 10%, preferably 0.1 to 1% |
|---|---|
| solid carrier: | 99.9 to 90%, preferably 99.9 to 99% |

Suspension Concentrates:

| active ingredient: | 5 to 75%, preferably 10 to 50% |
|---|---|
| water: | 94 to 24%, preferably 88 to 30% |
| surfactant: | 1 to 40%, preferably 2 to 30% |

Wettable Powders:

| active ingredient: | 0.5 to 90%, preferably 1 to 80% |
|---|---|
| surfactant: | 0.5 to 20%, preferably 1 to 15% |
| solid carrier: | 5 to 99%, preferably 15 to 98% |

Granulates:

| active ingredient: | 0.5 to 30%, preferably 3 to 15% |
|---|---|
| solid carrier: | 99.5 to 70%, preferably 97 to 85% |

The compositions can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds I for the preparation of these compositions are also a subject of the invention.

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compositions according to the invention are also suitable for the protection of plant propagation material, for example seeds, such as fruit, tubers or kernels, or nursery plants, against pests of the abovementioned type. The propagation material can be treated with the compositions prior to planting, for example seed can be treated prior to sowing. Alternatively, the compositions can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention.

PREPARATION EXAMPLES

The examples which follow are intended to illustrate the invention and show preferred compounds of formula I. Free valences represent the methyl group.

Example P1

Preparation of Compound T13.1.2

Step 1: Preparation of 2-methyl-2-nitro-1,3-propanediol ditosylate:

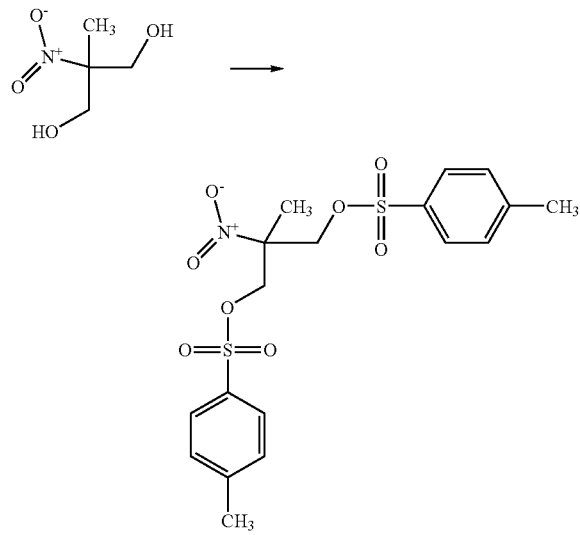

In analogy to F. I. Carroll, J. Org. Chem. 1969, 34, 466-8:

To a solution of 2-methyl-2-nitro-1,3-propanediol (80 g, 0.592 mol) and triethylamine (131.8 g, 1.303 mol) in diethyl ether (250 ml) is added a solution of tosyl chloride (225.7 g, 1.184 mol) in diethyl ether (800 ml) between −15° and −20° C. The resulting suspension is stirred at 0° C. for 1 hour, then 18 hours at ambient temperature. The reaction mixture is filtered, the solid residue is taken up twice in ethyl acetate and stirred, the suspension being filtered again. The combined ethyl acetate layers are evaporated to dryness giving a first crop of crude product (175.8 g). The ether filtrate is washed with water (2×) and brine, dried ($Na_2SO_4$), filtered, and partly concentrated. The suspension is filtered giving another 15.0 g of product. The crude solid product (190.8 g, 73%) is used in the next step without further purification.

Step 2: Preparation of 3-methyl-3-nitro-thietane:

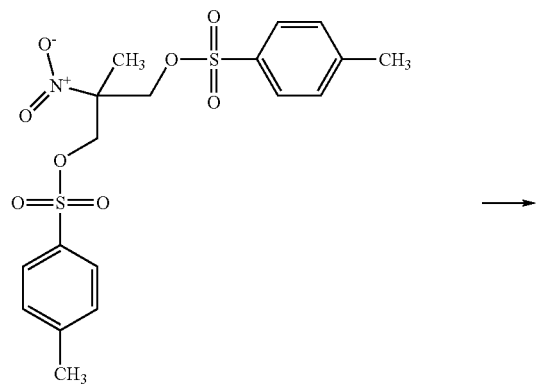

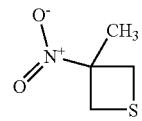

In analogy to K. K. Andersen et al., J. Org. Chem. 1978, 43, 3827-34:

A solution of 2-methyl-2-nitro-1,3-propanediol ditosylate (the product of step 1) (17 g, 38.3 mmol) in DMSO (130 ml) is treated with sodium sulfide ($Na_2S.xH_2O$ 32-38%, 11.92 g, ~53.5 mmol) and the mixture is stirred at a temperature of 90° C. (bath 110° C.) for 2 hours. The cooled reaction mixture is poured into water, extracted with $Et_2O$, the combined organic layers washed with water (2×) and brine, dried ($Na_2SO_4$), filtered, and concentrated. The crude liquid product (3.52 g, 69%) is used in the next step without further purification.

Step 3: Preparation of 3-amino-3-methyl-thietane:

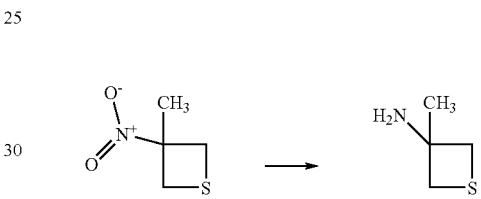

To a solution of 3-methyl-3-nitro-thietane (the product of step 2) (3.52 g, 26.4 mmol) in ethanol (100 ml) and water (50 ml) is added ammonium chloride (1.55 g, 29.0 mmol), followed by iron powder (14.0 g, 250.7 mmol) and the mixture is heated to reflux for 1 hour. The cooled reaction mixture is filtered through Hyflo, the residue washed with diethyl ether and dichloromethane, and the combined filtrate is concentrated carefully under reduced pressure. The product, a yellowish liquid (0.66 g, 24%), is used in the next step without further purification.

$^1$H-NMR ($CDCl_3$): 3.25 (d, J=9.3 Hz, 2H), 3.04 (d, J=9.8 Hz, 2H), 1.78 (s, 2H), 1.53 (s, 3H).

Step 4: Preparation of (2-(3-Chloro-pyridin-2-yl)-5-trifluoromethyl-2H-pyrazole-3-carboxylic acid [4-chloro-2-methyl-6-(3-methyl-thietan-3-ylcarbamoyl)-phenyl]-amide):

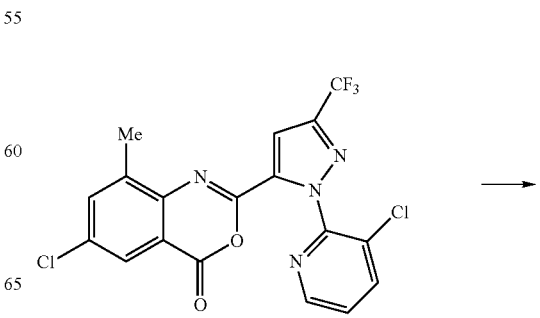

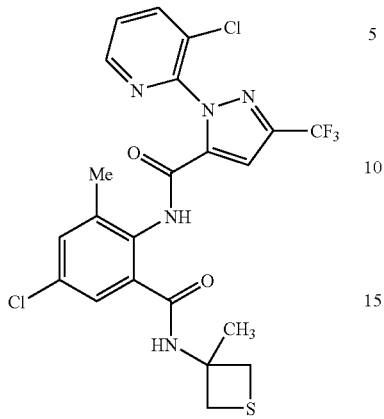

To a solution of 6-chloro-2-[1-(3-chloro-2-pyridinyl)-3-(trifluoromethyl)-1H-pyrazol-5-yl]-8-methyl-4H-3,1-benzoxazin-4-one (1.13 g, 2.56 mmol) (prepared according to WO 02/48115, example 2D) in tetrahydrofuran (15 ml) is added 3-amino-3-methyl-thietane (the product of step 3) (0.66 g, 6.40 mmol), and the mixture is heated for 48 hours at 50° C., then to reflux for 12 hours. The cooled reaction mixture is poured into water, extracted with ethyl acetate, the combined organic layers washed with water and brine, dried ($Na_2SO_4$), filtered, and concentrated. The crude product is purified by flash chromatography (ethyl acetate/hexane 1:2) to afford 560 mg (40%) of the title compound as a white solid, m.p. 238-241° C.

$^1$H-NMR ($CDCl_3$): 10.19 (s, 1H), 8.46 (d, 1H), 7.88 (d, 1H), 7.69 (s, 1H), 7.41 (dd, 1H), 7.10 (s, 2H), 6.39 (s, 1H), 3.63 (d, 2H), 2.98 (d, 2H), 2.09 (s, 3H), 1.68 (s, 3H); MS (electrospray ES+): 544, 546 (M+H)$^+$.

Step 5: Preparation of compound T13.1.2 (2-(3-Chloro-pyridin-2-yl)-5-trifluoromethyl-2H-pyrazole-3-carboxylic acid [4-chloro-2-methyl-6-(3-methyl-1,1-dioxo-1λ$^6$-thietan-3-ylcarbamoyl)-phenyl]-amide):

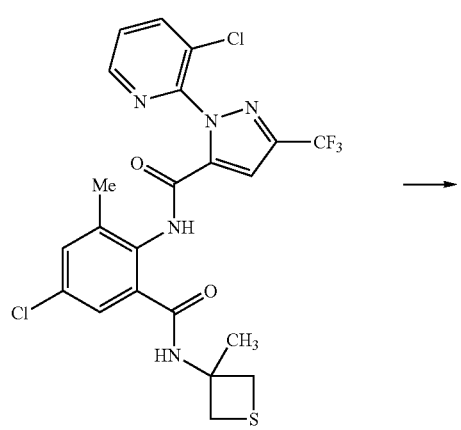

T13.1.2

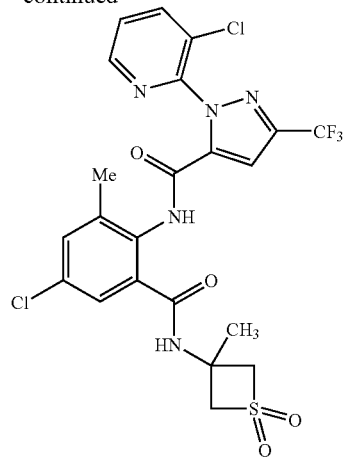

To a solution of 2-(3-chloro-pyridin-2-yl)-5-trifluoromethyl-2H-pyrazole-3-carboxylic acid [4-chloro-2-methyl-6-(3-methyl-thietan-3-ylcarbamoyl)-phenyl]-amide (the product of step 4, 150 mg, 0.275 mmol) in dichloromethane (10 ml) is added m-chloroperbenzoic acid (143 mg, 0.579 mmol), and the mixture is stirred at room temperature for 1 hour. The reaction mixture is partly concentrated, taken up in ethyl acetate, the organic layer washed with $Na_2CO_3$ aq. sat. (3×) and brine, dried ($Na_2SO_4$), filtered, and concentrated. The crude product is purified by flash chromatography (ethyl acetate) to afford 78 mg (49%) of the title compound T13.1.2 as a white solid, m.p. 168-171° C.

$^1$H-NMR ($CDCl_3$): 9.61 (s, 1H), 8.48 (d, 1H), 7.90 (d, 1H), 7.42 (dd, 1H), 7.33 (s, 1H), 7.25-7.22 (2×s, 2H), 6.72 (s, 1H), 4.38 (d, 2H), 4.09 (d, 2H), 2.14 (s, 3H), 1.75 (s, 3H); MS (electrospray ES+): 576, 578 (M+H)$^+$.

Example P2

Preparation of Compound T44.1.2

Step 1: Preparation of 2-methyl-2-nitro-1,3-propanediol ditriflate:

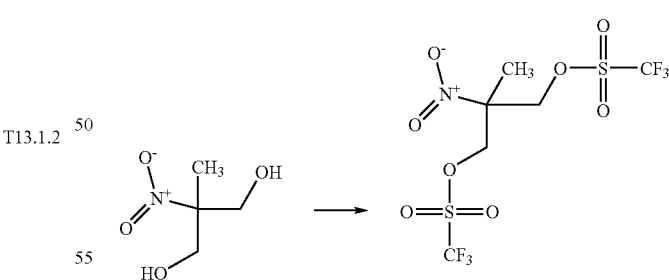

To a solution of triflic anhydride (16.5 ml, 0.1 mol) in chloroform (50 ml) is added a solution of 2-methyl-2-nitro-1,3-propanediol (6.75 g, 0.05 mol) and pyridine (8.85 ml, 0.11 mol) in chloroform (50 ml) with external cooling to ensure a temperature of between 0° and 5° C. during the addition. After the addition the cooling bath is removed and the reaction stirred for 18 hours at ambient temperature. The reaction mixture is transferred to a separating funnel and washed with water. The organic layer is dried ($Na_2SO_4$), filtered and evaporated to dryness. The crude product is purified by chromatography using a 4:1 mixture of Hexane:Ethyl acetate as eluant; the product is obtained as a solid with melting point 50-52° C.

Step 2: Preparation of 3-methyl-3-nitro-N-benzylazetidine:

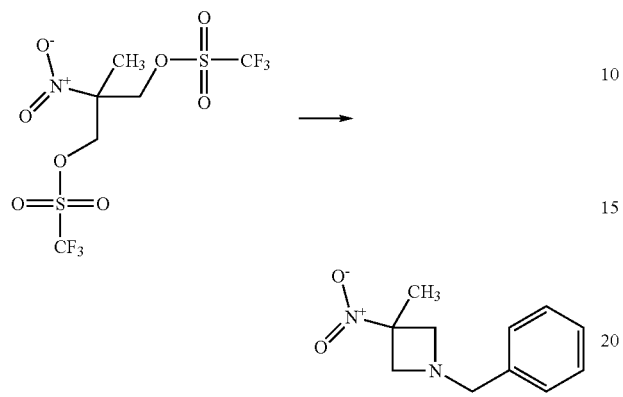

A solution of 2-methyl-2-nitro-1,3-propanediol ditriflate [the product of step 1] (4.0 g, 10 mmol) in acetonitrile (70 ml) is cooled to 0° C.-5° C. and N-ethyl-diisopropylamine (3.23 g, 25 mmol) is added, followed by benzylamine (1.60 g, 15 mmol) and the mixture is stirred at a temperature of 80° C. for 12 hours. The cooled reaction mixture concentrated under reduced pressure, dissolved in ethyl acetate and transferred to a separating funnel. This is then washed with water (2×) and brine, dried (Na$_2$SO$_4$), filtered, and concentrated. The crude liquid product is used in the next step without further purification. The crude product is purified by chromatography using a 3:1 mixture of Hexane: Ethyl acetate as eluant; the product is obtained as an oil. $^1$H-NMR (CDCl$_3$): 7.3 (m, 5H), 3.75 (d, 2H), 3.68 (s, 2H), 3.42 (d, 2H), 1.88 (s, 3H).

Step 3: Preparation of 3-amino-3-methyl-N-benzylazetidine:

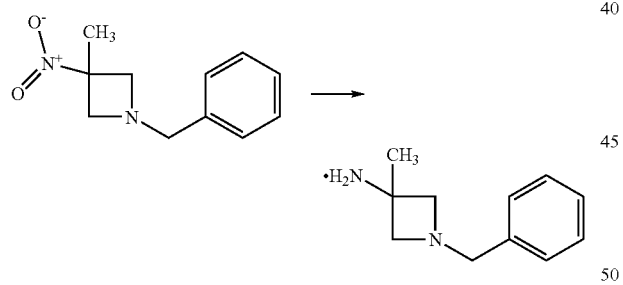

A solution of 3-methyl-3-nitro-N-benzylazetidine [the product of step 2] (3.9 g, 18.9 mmol) in ethyl acetate (370 ml) and 5% acetic acid (370 ml) is heated to reflux. Iron powder (5.25 g, 94.1 mmol) is added portion-wise every 5 minutes. After the addition is complete the reaction mixture is heated at reflux for 6 hours. The cooled reaction mixture is filtered through Hyflo, and the residue washed with ethyl acetate. The filtrate is transferred to a separating funnel and the organic layer separated and discarded. The aqueous layer is treated with 30% NaOH solution with ice cooling to give a pH of ca. 11. Dichloromethane is then added and the mixture vigorously stirred at ambient temperature for 10 minutes. This mixture is filtered through Hyfol, the filtrate transferred to a separating funnel and the organic layer is separated, dried (Na$_2$SO$_4$), filtered, and concentrated. The crude oily product (2.30 g, 69%) is used in the next step without further purification. $^1$H-NMR (CDCl$_3$): 7.2 (m, 5H), 3.62 (s, 2H), 3.27 (d, 2H), 2.88 (d, 2H), 1.68 (bs, 2H), 1.4 (s, 3H).

Step 4: Preparation of compound T44.1.2 (2-(3-chloropyridin-2-yl)-5-trifluoromethyl-2H-pyrazole-3-carboxylic acid [4-chloro-2-methyl-6-(3-methyl-N-benzylazetidine-3-ylcarbamoyl)-phenyl]-amide):

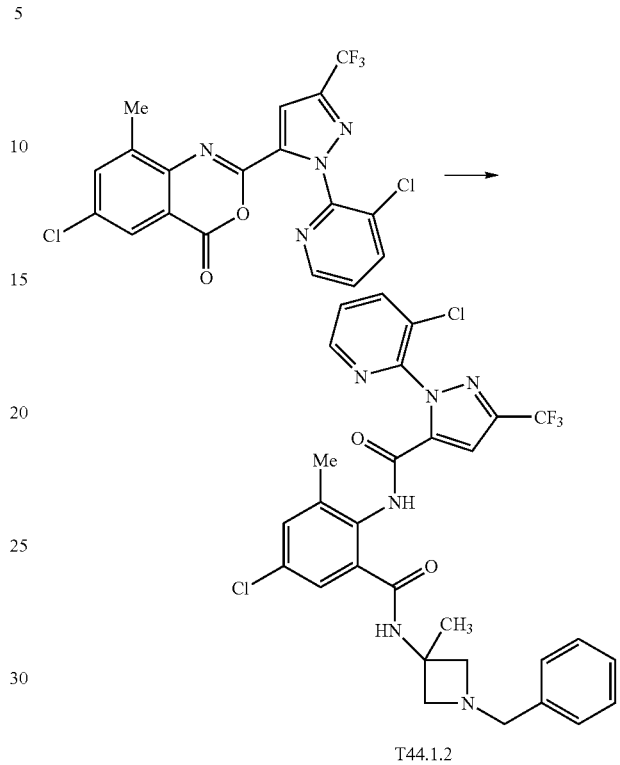

T44.1.2

To a solution of 6-chloro-2-[1-(3-chloro-2-pyridinyl)-3-(trifluoromethyl)-1H-pyrazol-5-yl]-8-methyl-4H-3,1-benzoxazin-4-one (353 mg, 0.8 mmol) [prepared according to WO 02/48115, example 2D] in tetrahydrofuran (10 ml) is added 3-amino-3-methyl-N-benzylazetidine [the product of step 3] (176 mg, 0.8 mmol), and the mixture is stirred at ambient temperature for 18 hours. The reaction mixture is concentrated and the crude product is purified by flash chromatography (ethyl acetate) to afford 250 mg (45%) of the title compound T44.1.2 as a white solid, m.p. 127-130° C.

$^1$H-NMR (CDCl$_3$): 10.4 (s, 1H), 8.4 (d, 1H), 7.85 (d, 1H), 7.75 (s, 1H), 7.4 (dd, 1H), 7.26 (m, 5H), 7.1 (d, 2H), 6.5 (s, 1H), 3.5 (s, 2H), 3.35 (d, 2H), 3.07 (d, 2H), 2.1 (s, 3H), 1.57 (s, 3H).

Example P3

Preparation of Compound T9.1.1

Step 1: Preparation of N-(tert-butyloxycarbonyl)-3-thietanamine:

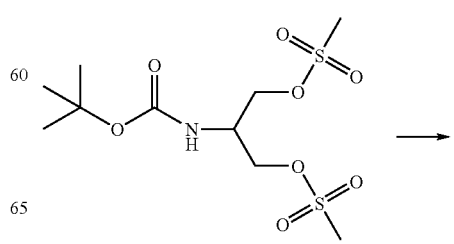

-continued

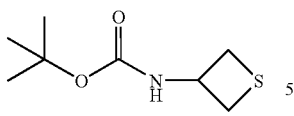

A solution of N-(tert-butyloxycarbonyl)-2-amino-1,3-propanediol dimesylate [prepared according to E. Benoist et al., Synthesis 1998, (8), 1113-1118] (25 g, 72.0 mmol) in ethanol (375 ml) is treated with sodium sulfide (Na$_2$S.xH$_2$O 32-38%, 16.82 g, ~75.4 mmol) and the mixture is stirred at a temperature of 50° C. (bath 60° C.) for 45 minutes. The cooled reaction mixture is concentrated under reduced pressure and the solid residue poured into water, extracted with Et$_2$O, the combined organic layers washed with brine, dried (Na$_2$SO$_4$), filtered, and concentrated. The crude solid product (12.6 g, 92%) is used in the next step without further purification.

Step 2: Preparation of 3-thietanamine hydrobromide salt:

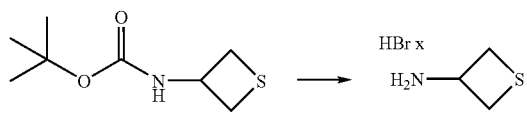

A 5.7M solution of HBr in acetic acid (11.0 ml, 62.7 mmol) is added dropwise to a solution of N-(tert-butyloxycarbonyl)-3-thietanamine [the product of step 1] (9.17 g, 48.5 mmol) in diethyl ether (250 ml) cooled at −20° C. and the mixture is stirred at −20° C. for 10 minutes. The cooling bath is removed and the reaction stirred for 3 hours at ambient temperature. The resulting white suspension is filtered and the residue washed with diethyl ether yielding a first crop of product (6.0 g). The ether filtrate is concentrated and the residue resubjected to the same reaction conditions and workup giving another 1.3 g of product. The crude solid product (7.3 g, 89%) with a melting point of 186-190° C. is used in the next step without further purification.

$^1$H-NMR (d$_6$-DMSO): 8.23 (br s, 3H), 4.52 (m, 1H), 3.47 (m, 2H), 3.18 (m, 2H).

Step 3: Preparation of 2-(3-chloro-pyridin-2-yl)-5-trifluoromethyl-2H-pyrazole-3-carboxylic acid [4-chloro-2-methyl-6-(thietan-3-ylcarbamoyl)-phenyl]-amide:

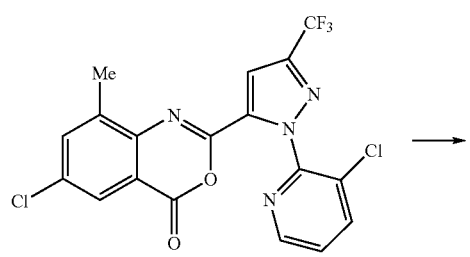

-continued

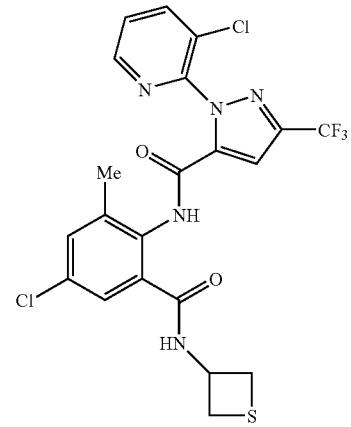

To a solution of 6-chloro-2-[1-(3-chloro-2-pyridinyl)-3-(trifluoromethyl)-1H-pyrazol-5-yl]-8-methyl-4H-3,1-benzoxazin-4-one (500 mg, 1.13 mmol) [prepared according to WO 02/48115, example 2D] in tetrahydrofuran (10 ml) is added triethylamine (0.4 ml, 2.87 mmol) and 3-thietanamine hydrobromide salt [the product of step 2] (250 mg, 1.47 mmol), and the mixture is heated to reflux overnight. The cooled reaction mixture is poured into water, extracted with ethyl acetate, the combined organic layers washed with water and brine, dried (Na$_2$SO$_4$), filtered, and concentrated. The crude product is purified by flash chromatography (ethyl acetate/hexane 1:2) to afford 250 mg (41%) of the title compound as a white solid.

$^1$H-NMR (CDCl$_3$): 9.94 (s, 1H), 8.48 (d, 1H), 7.88 (d, 1H), 7.42 (dd, 1H), 7.29 (s, 2H), 7.24 (s, 1H), 6.53 (d, 1H), 5.31 (m, 1H), 3.41 (m, 2H), 3.33 (m, 2H), 2.18 (s, 3H); MS (electrospray ES+): 530, 532 (M+H)$^+$.

Step 4: Preparation of compound T9.1.1 (2-(3-chloro-pyridin-2-yl)-5-trifluoromethyl-2H-pyrazole-3-carboxylic acid [4-chloro-2-methyl-6-(1-oxo-1λ$^4$-thietan-3-ylcarbamoyl)-phenyl]-amide);

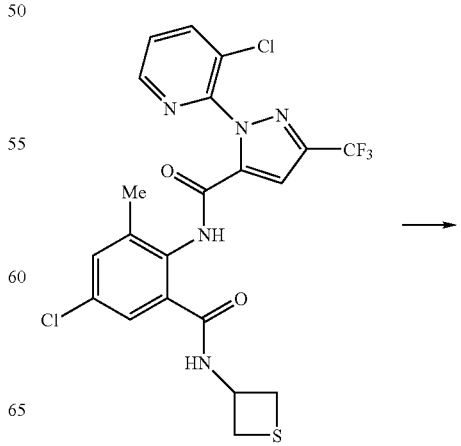

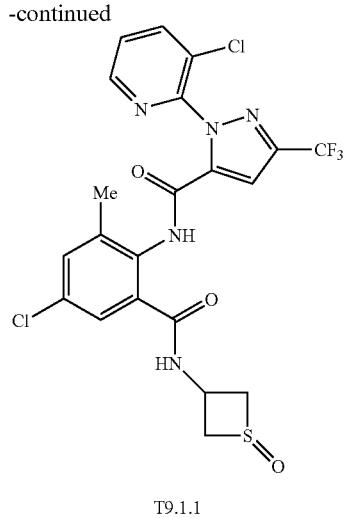

T9.1.1

To a solution of 2-(3-chloro-pyridin-2-yl)-5-trifluoromethyl-2H-pyrazole-3-carboxylic acid [4-chloro-2-methyl-6-(thietan-3-ylcarbamoyl)-phenyl]-amide [the product of step 3] (200 mg, 0.377 mmol) in dichloromethane (10 ml) at 0° C. is added m-chloro-perbenzoic acid (93 mg, 0.377 mmol) in dichloromethane (2 ml) dropwise. Another 10 mg of m-chloro-perbenzoic acid is needed to complete the reaction after stirring at 0° C. for 40 minutes. The reaction mixture is treated with NaHCO$_3$ aq. sat. and extracted with dichloromethane, the combined organic layer washed with brine, dried (Na$_2$SO$_4$), filtered, and concentrated. The crude product is purified by flash chromatography (ethyl acetate) to afford 50 mg (24%) of the title compound T9.1.1 as a white solid, m.p. 241-244° C. (major diastereomer called T9.1.1 diastereomer A).

$^1$H-NMR (d$_6$-DMSO): 10.38 (s, 1H), 8.91 (d, 1H), 8.54 (d, 1H), 8.23 (d, 1H), 7.75 (s, 1H), 7.67 (dd, 1H), 7.52 (s, 1H), 7.42 (s, 1H), 4.22 (m, 1H), 3.95 (m, 2H), 3.16 (m, 2H), 2.20 (s, 3H); MS (electrospray ES+): 546, 548 (M+H)$^+$.

Example P4

Preparation of Compound T13.1.22

Step 1: Preparation of 1,1-dioxo-3-methyl-3-thietanamine trifluoroacetic acid salt:

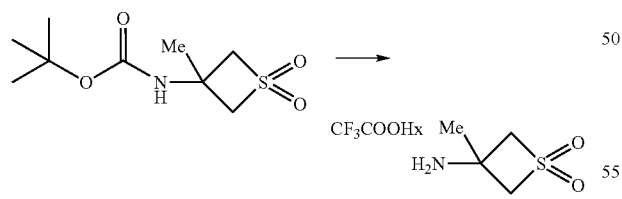

A solution of N-(tert-butyloxycarbonyl)-1,1-dioxo-3-methyl-3-thietanamine [prepared in analogy to Example P3, step 1 and Example P1, step 5] (1.7 g, 7.2 mmol) in dichloromethane (20 ml) at 0° C. is treated with trifluoroacetic acid (13 ml) and the reaction mixture stirred overnight at ambient temperature. The mixture is concentrated under reduced pressure, the solid residue suspended in diethyl ether, stirred, filtered and dried. The crude solid product (1.4 g, 78%) with a melting point of 208-210° C. is used in the next step without further purification.

$^1$H-NMR (d$_6$-DMSO): 8.82 (br s, 3H), 4.56 (d, 2H), 4.29 (d, 2H), 1.68 (s, 3H).

Step 2: Preparation of 5-chloro-3-methyl-2-sulfinylaminobenzoyl chloride

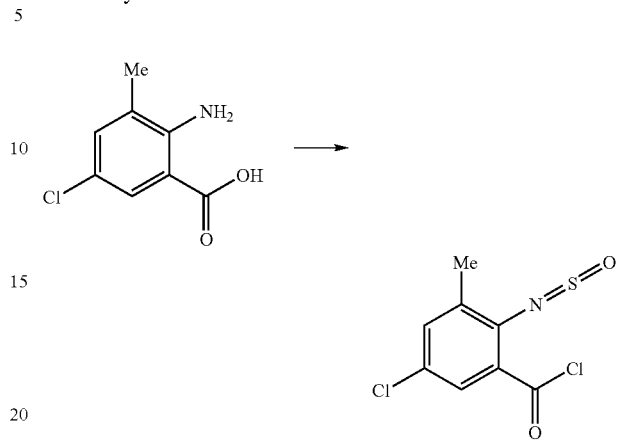

In analogy to J. Garin et al., Tetrahedron Lett. 1991, 32, 3263-3264:

To a suspension of 2-amino-5-chloro-3-methyl-benzoic acid (18.5 g, 100 mmol) in toluene (200 ml) is added thionyl chloride (36 ml, 500 mmol) and the mixture is heated to reflux and stirred at that temperature until the rapid gas evolution slowed down. The resulting solution is concentrated under reduced pressure to give a solid residue which is dried under high vacuum. The crude solid product (23.7 g, 95%) is used in the next step without further purification.

$^1$H-NMR (CDCl$_3$): 8.07 (d, 1H), 7.56 (d, 1H), 2.30 (s, 3H).

Step 3: Preparation of 2-amino-5-chloro-3-methyl-N-(3-methyl-1,1-dioxo-1λ$^6$-thietan-3-yl)-benzamide

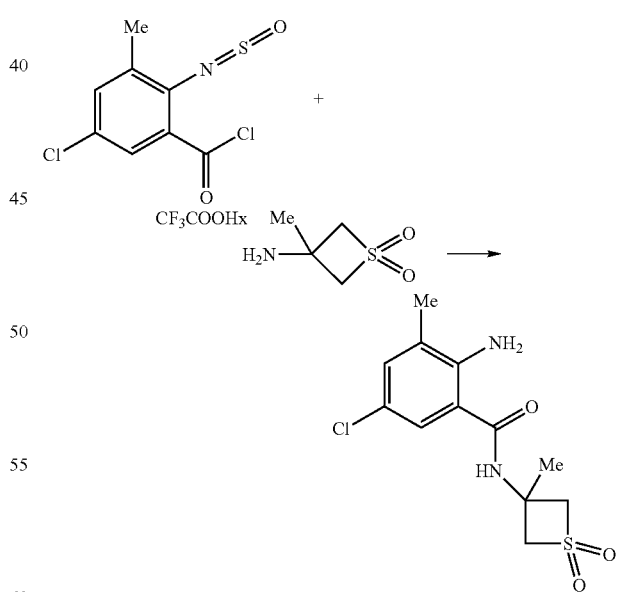

To a solution of 1,1-dioxo-3-methyl-3-thietanamine trifluoroacetic acid salt [the product of step 1] (598 mg, 2.40 mmol) and triethylamine (0.836 ml, 6.00 mmol) in tetrahydrofuran (6 ml) cooled at 0-5° C. is added a solution of 5-chloro-3-methyl-2-sulfinylaminobenzoyl chloride [the product of step 2] (600 mg, 2.4 mmol) in tetrahydrofuran (4 ml). The reaction mixture is stirred at room temperature overnight, and then poured into water. After extraction with ethyl acetate, the combined organic layers are washed with brine, dried (Na$_2$SO$_4$), filtered and concentrated. The crude product is purified by column chromatography on silica gel (ethyl acetate/hexane 1:4) to afford the title benzamide [compound D54 from Table D] (410 mg, 56%) as a white solid with a melting point of 79-82° C.

$^1$H-NMR (CDCl$_3$): 7.20 (s, 1H), 7.12 (s, 1H), 6.52 (s, 1H), 5.58 (br s, 2H), 4.64 (d, 2H), 4.15 (d, 2H), 2.13 (s, 3H), 1.87 (s, 3H); MS (electrospray ES+): 303, 305 ((M+H)$^+$).

Step 4: Preparation of compound T13.1.22 (2-(3-chloro-pyridin-2-yl)-5-(2,2,2-trifluoro-ethoxy)-2H-pyrazole-3-carboxylic acid [4-chloro-2-methyl-6-(3-methyl-1,1-dioxo-1λ$^6$-thietan-3-ylcarbamoyl)-phenyl]-amide)

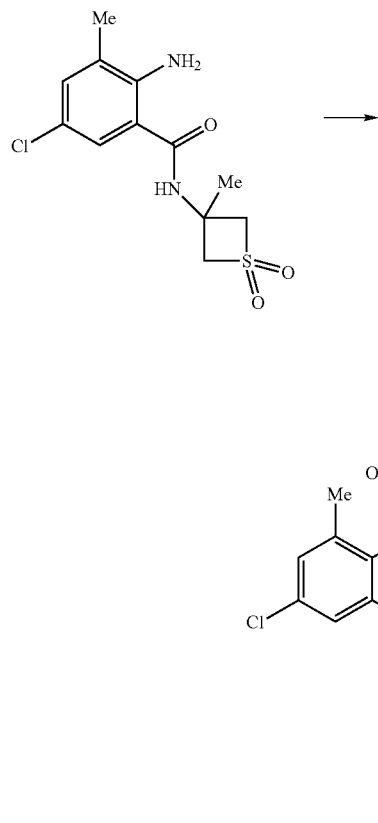

T13.1.22

To a solution of 2-amino-5-chloro-3-methyl-N-(3-methyl-1,1-dioxo-1λ$^6$-thietan-3-yl)-benzamide [the product of step 3] (340 mg, 1.12 mmol) in tetrahydrofuran (6 ml) cooled at 0-5° C. is added a solution of 2-(3-chloro-pyridin-2-yl)-5-(2,2,2-trifluoro-ethoxy)-2H-pyrazole-3-carbonyl chloride (1.12 mmol, 1 eq.) in tetrahydrofuran (4 ml). The reaction mixture is stirred at room temperature overnight, and the solvent evaporated in vacuo. The crude product is purified by column chromatography on silica gel (gradient ethyl acetate/hexane 1:4→1:1) to afford the title bisamide compound T13.1.22 (279 mg, 41%) as a white solid with a melting point>250° C.

$^1$H-NMR (CDCl$_3$): 10.05 (s, 1H), 8.83 (s, 1H), 8.45 (d, 1H), 7.85 (d, 1H), 7.42 (s, 1H), 7.38 (dd, 1H), 7.29 (s, 1H), 6.67 (s, 1H), 4.69 (q, 2H), 4.54 (d, 2H), 4.08 (d, 2H), 2.22 (s, 3H), 1.76 (s, 3H); MS (electrospray ES+): 606, 608 ((M+H)$^+$).

Example P5

Preparation of Compound D14 from Table D: (2-amino-5-chloro-3-methyl-N-(3-methyl-thietan-3-yl)-benzamide)

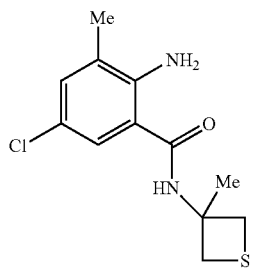

D14 from Table D

This benzamide is prepared in analogy to Example P4, step 3 from the starting materials Example P4, step 2 and Example P1, step 3 giving a white solid with a melting point of 92-94° C.

$^1$H-NMR (CDCl$_3$): 7.14 (s, 1H), 7.10 (s, 1H), 6.09 (s, 1H), 5.57 (br s, 2H), 3.90 (d, 2H), 3.03 (d, 2H), 2.14 (s, 3H), 1.83 (s, 3H); MS (electrospray ES+): 271, 273 ((M+H)$^+$).

Example P6

Preparation of Compound C13 from Table C: (2,2-dimethyl-thietan-3-ylamine)

C13 from Table C

To a solution of 2,2-dimethyl-thietan-3-one [prepared according to W. Luettke et al., Chemische Berichte 1977, 110, 1421-31] (8.9 g, 76.6 mmol) in methanol (200 ml) is added ammonium acetate (59 g, 765 mmol) and sodium cyanoborohydride (7.8 g, 118.7 mmol) and the reaction mixture is heated to reflux for 2 hours. The cooled reaction mixture is flushed with nitrogen, acidified to pH 2 with concentrated hydrochloric acid (maintaining the temperature under 10° C.), and concentrated under reduced pressure. The residue is poured into water, extracted with diethyl ether (2×), the pH of the aqueous phase adjusted to pH 11 with 30% sodium hydroxide and the product extracted with diethyl ether. The combined organic layers are washed with brine, dried (Na$_2$SO$_4$), filtered and concentrated. The crude oily product (1.47 g, 16%) is used without further purification.

$^1$H-NMR (CDCl$_3$): 3.83 (dd, 1H), 3.19 (t, 1H), 2.95 (t, 1H), 1.63 (br s, 2H), 1.50 (s, 3H), 1.42 (s, 3H).

The compounds listed in the following Table P can be prepared analogous to the procedures described above (m.p.=melting point in ° C.).

TABLE P

| Cmpd No. | Structure | Phys. Data |
|---|---|---|
| T13.1.2 | 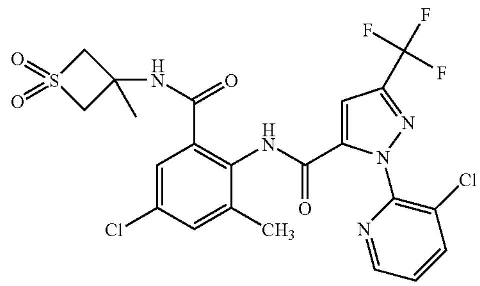 | m.p. 168-171 |
| T15.1.1 | 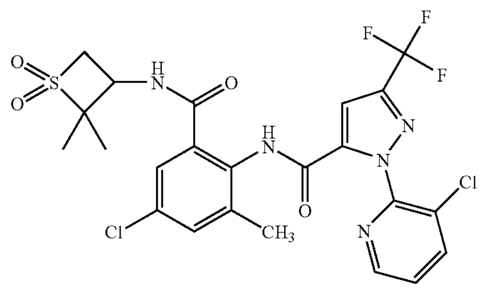 | m.p. 161-163 |
| T15.1.91 | 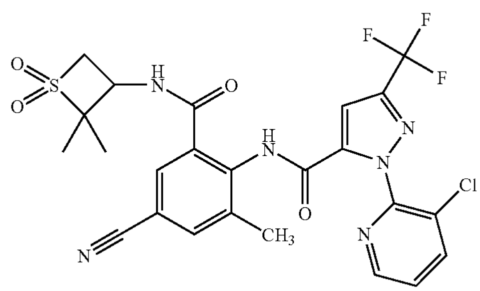 | m.p. 198-200 |
| T13.1.1 | 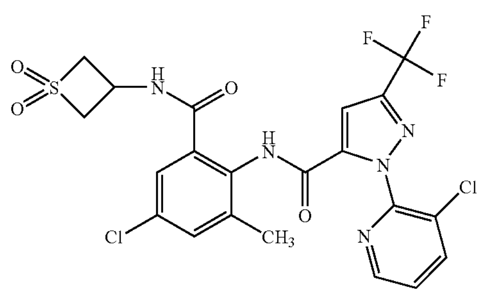 | 238-241 |
| T9.1.2 | Diastereomer A | m.p. 239-241 |

TABLE P-continued
Compounds of formula I:
| Cmpd No. | Structure | Phys. Data |
|---|---|---|
| T9.1.2 | 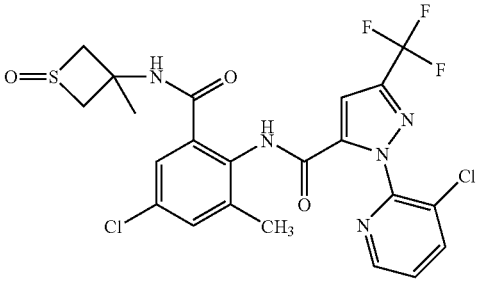 Diastereomer A | m.p. 263-265 |
| T16.1.1 | 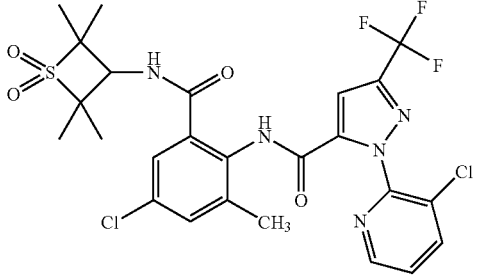 | m.p. >250, MS (ES+): 618, 620 (M + H)+ |
| T17.1.2 | 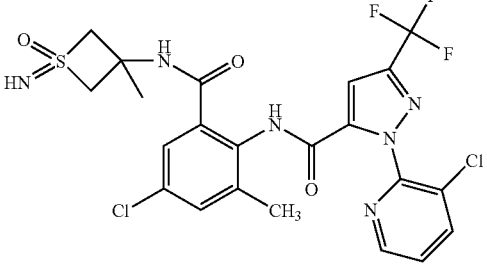 Diastereomer A | m.p. 153-155 |
| T17.1.2 | 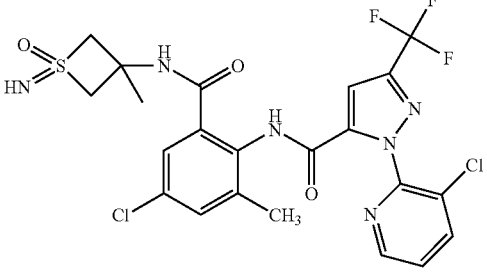 Diastereomer B | m.p. 216-220 |
| T16.1.91 | 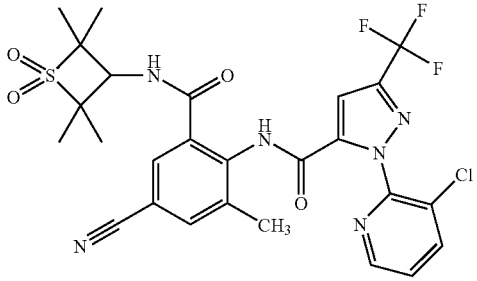 | m.p. >250, MS (ES+): 609, 611 (M + H)+ |

TABLE P-continued

Compounds of formula I:

| Cmpd No. | Structure | Phys. Data |
|---|---|---|
| T13.1.92 | 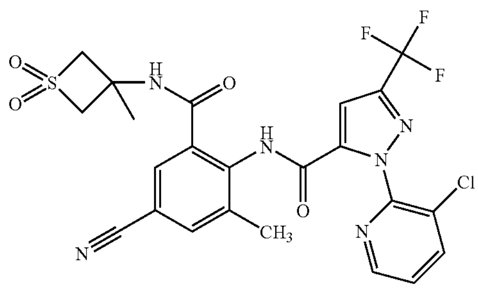 | m.p. 231-235 |
| T13.1.361 | 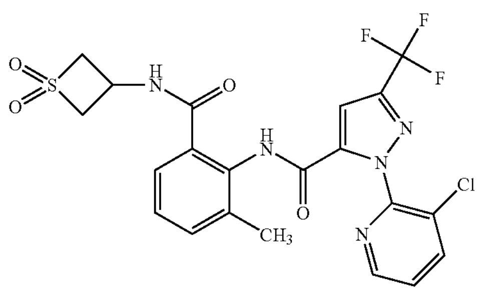 | m.p. 242-244 |
| T13.1.391 | 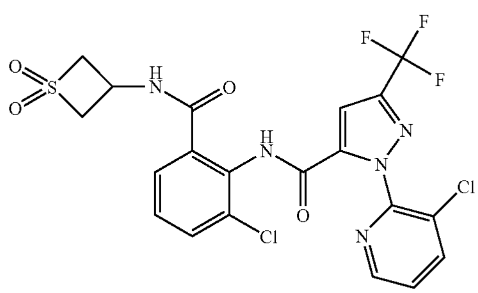 | m.p. 218 |
| T13.1.91 | 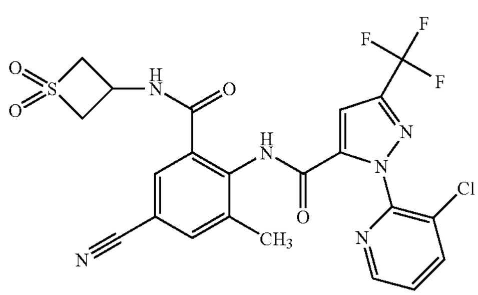 | m.p. 160-163 |
| T13.1.6 | 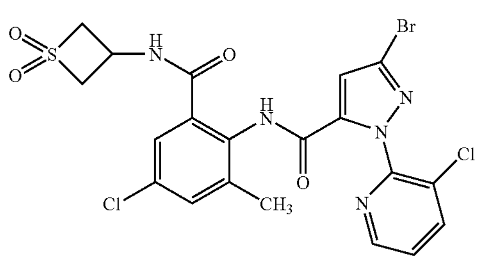 | m.p. 156-158 |

TABLE P-continued

Compounds of formula I:

| Cmpd No. | Structure | Phys. Data |
|---|---|---|
| T13.1.96 | 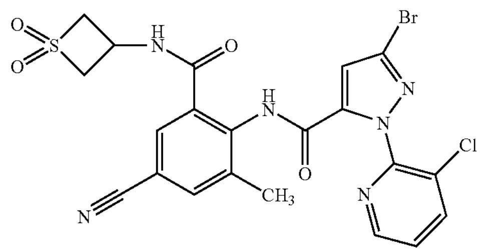 | m.p. 157-158 |
| T44.1.2 | 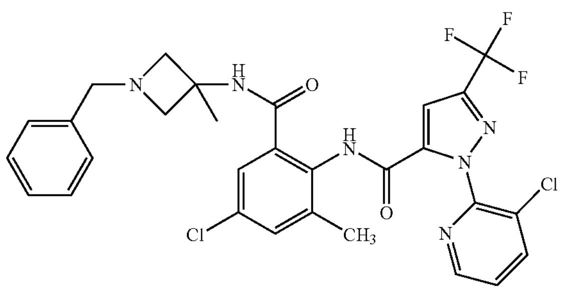 | m.p. 127-130 |
| T13.1.8 | 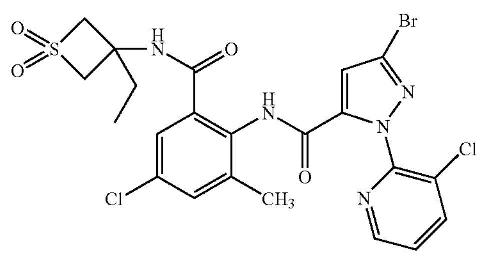 | Solid, MS (ES+): 600, 602, 604 (M + H)+ |
| T13.1.23 | 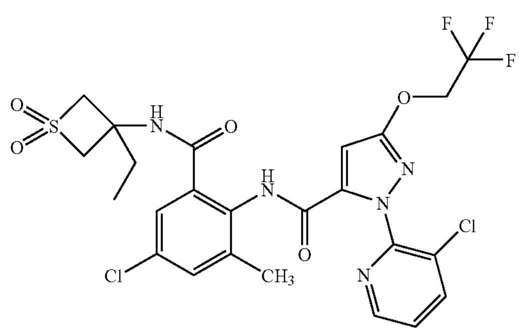 | m.p. 263-267 |
| T13.1.93 | 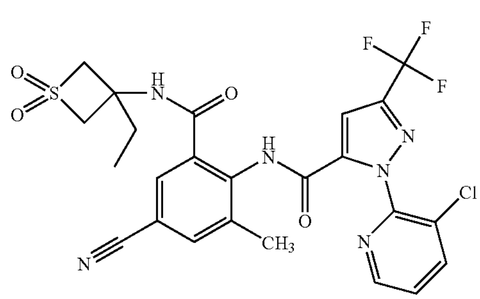 | m.p. 249-252 |

TABLE P-continued

Compounds of formula I:

| Cmpd No. | Structure | Phys. Data |
|---|---|---|
| T13.1.113 | 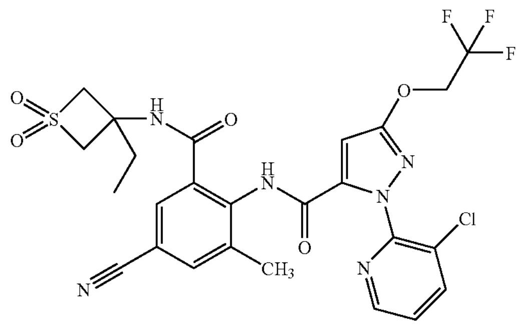 | m.p. 240-242 |
| T13.1.21 | 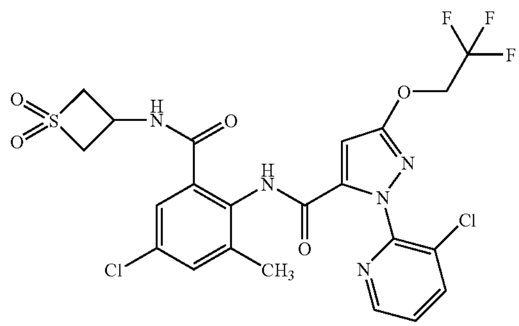 | m.p. 179-181 |
| T13.1.111 | 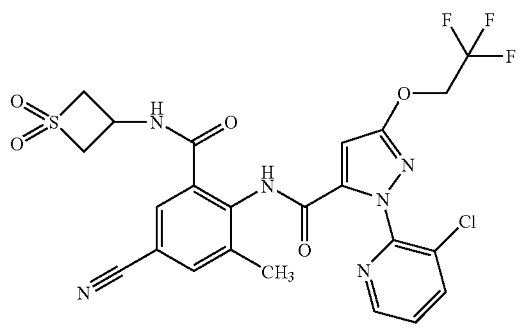 | m.p. 158-160 |
| T13.1.3 | 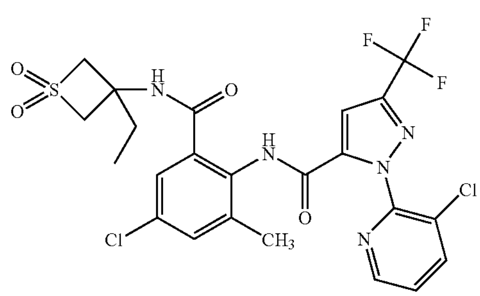 | m.p. 234-236 |
| T13.1.98 | 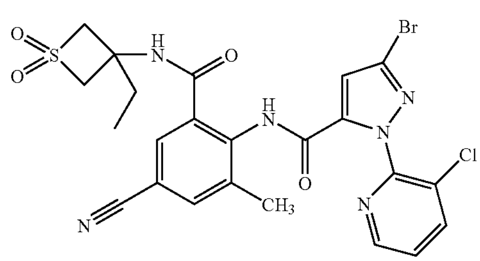 | Solid, MS (ES+): 591, 593, 595 (M + H)+ |

TABLE P-continued

Compounds of formula I:

| Cmpd No. | Structure | Phys. Data |
| --- | --- | --- |
| T9.1.1 | Diastereomer A | m.p. 241-244 |
| T13.1.112 | 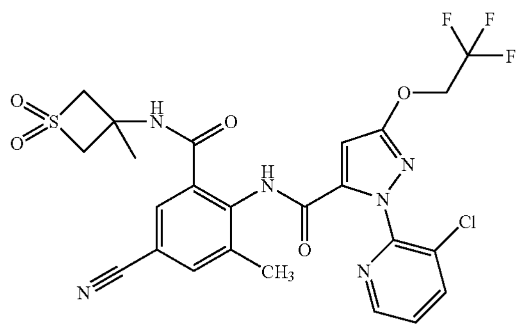 | m.p. 216-219 |
| T13.1.7 | 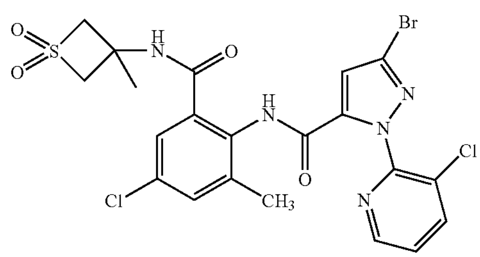 | m.p. 191-193 |
| T13.1.97 | 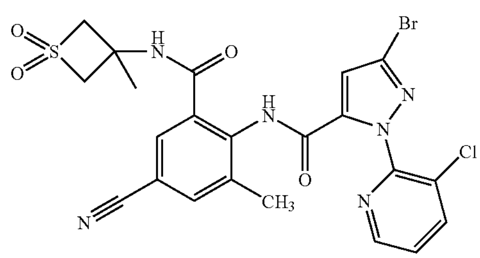 | m.p. >250, MS (ES+): 577, 579, 581 (M + H)+ |
| T9.1.7 | Diastereomer A | m.p. 244-247 |

TABLE P-continued

Compounds of formula I:

| Cmpd No. | Structure | Phys. Data |
|---|---|---|
| T13.1.422 | 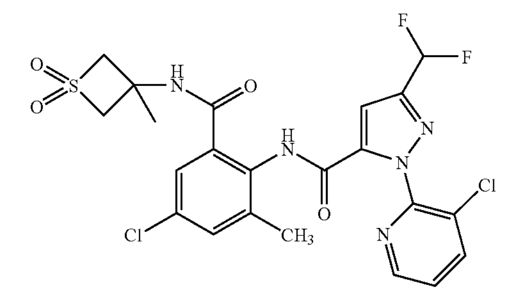 | m.p. 170-173 |
| T13.1.432 | 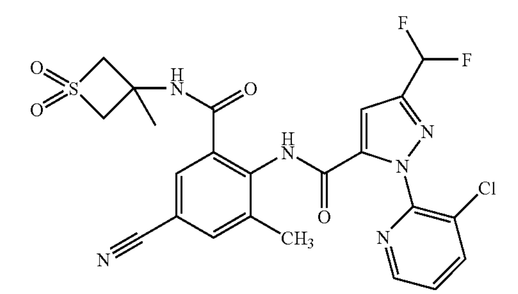 | m.p. 238-241 |
| T9.1.22 | Diastereomer A | m.p. 220-222 |
| T9.1.112 | Diastereomer A | m.p. 223-225 |

TABLE P-continued
Compounds of formula I:
| Cmpd No. | Structure | Phys. Data |
|---|---|---|
| T9.1.97 | 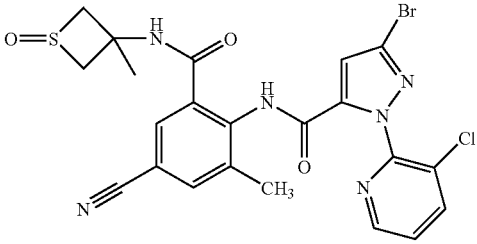<br>Diastereomer A | m.p. 244-249 |
| T13.1.22 | 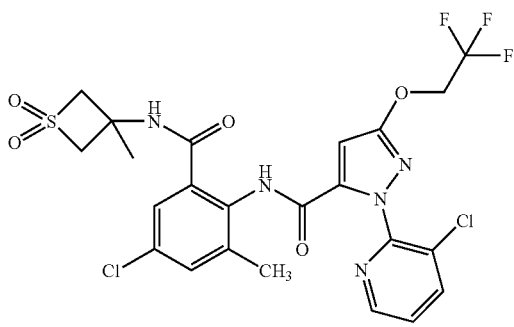 | m.p. >250, MS (ES+): 606, 608 (M + H)+ |
| T13.1.421 | 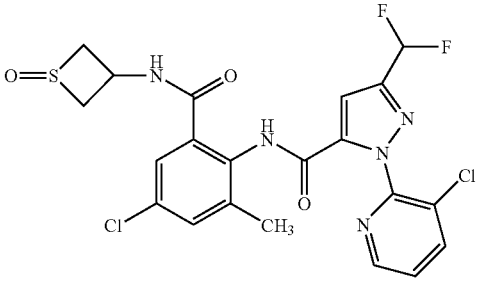<br>Diastereomer A | m.p. 151-155 |
| T9.1.421 | 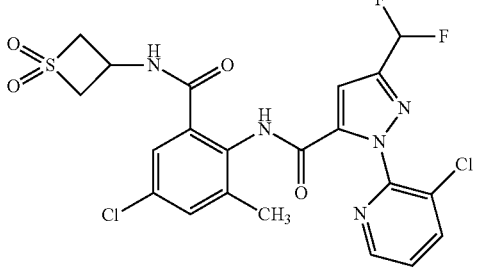 | m.p. 171-173 |
| T13.1.431 | 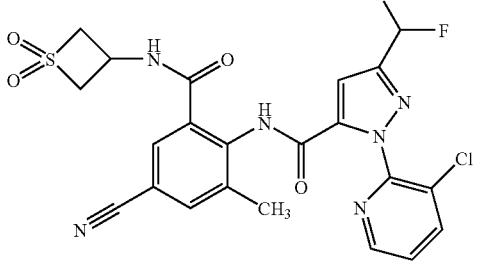 | m.p. 158-160 |

TABLE P-continued

Compounds of formula I:

| Cmpd No. | Structure | Phys. Data |
|---|---|---|
| T9.1.431 | (structure: Diastereomer A) | m.p. 230-233 |
| T9.1.422 | (structure: Diastereomer A) | m.p. 169-173 |
| T9.1.432 | (structure: Diastereomer A) | m.p. 235-237 |

The examples which follow are intended to illustrate the invention and show further preferred compounds of formula I. They do not limit the invention. "Me" is the methyl group.

TABLE A

Substituent designations for Tables 1 to 44:

| Line | $R_{91}$ | $R_{92}$ | $R_{93}$ | $R_{35}$ |
|---|---|---|---|---|
| A.1.1 | Me | Cl | $CF_3$ | H |
| A.1.2 | Me | Cl | $CF_3$ | $CH_3$ |
| A.1.3 | Me | Cl | $CF_3$ | $CH_2CH_3$ |
| A.1.4 | Me | Cl | $CF_3$ | $CH_2OCH_3$ |
| A.1.5 | Me | Cl | $CF_3$ | $CF_3$ |
| A.1.6 | Me | Cl | Br | H |
| A.1.7 | Me | Cl | Br | $CH_3$ |
| A.1.8 | Me | Cl | Br | $CH_2CH_3$ |
| A.1.9 | Me | Cl | Br | $CH_2OCH_3$ |
| A.1.10 | Me | Cl | Br | $CF_3$ |
| A.1.11 | Me | Cl | Cl | H |
| A.1.12 | Me | Cl | Cl | $CH_3$ |
| A.1.13 | Me | Cl | Cl | $CH_2CH_3$ |
| A.1.14 | Me | Cl | Cl | $CH_2OCH_3$ |
| A.1.15 | Me | Cl | Cl | $CF_3$ |

TABLE A-continued

Substituent designations for Tables 1 to 44:

| Line | $R_{91}$ | $R_{92}$ | $R_{93}$ | $R_{35}$ |
|---|---|---|---|---|
| A.1.16 | Me | Cl | $OCF_2H$ | H |
| A.1.17 | Me | Cl | $OCF_2H$ | $CH_3$ |
| A.1.18 | Me | Cl | $OCF_2H$ | $CH_2CH_3$ |
| A.1.19 | Me | Cl | $OCF_2H$ | $CH_2OCH_3$ |
| A.1.20 | Me | Cl | $OCF_2H$ | $CF_3$ |
| A.1.21 | Me | Cl | $OCH_2CF_3$ | H |
| A.1.22 | Me | Cl | $OCH_2CF_3$ | $CH_3$ |
| A.1.23 | Me | Cl | $OCH_2CF_3$ | $CH_2CH_3$ |
| A.1.24 | Me | Cl | $OCH_2CF_3$ | $CH_2OCH_3$ |
| A.1.25 | Me | Cl | $OCH_2CF_3$ | $CF_3$ |
| A.1.26 | Me | Cl | $OCF_3$ | H |
| A.1.27 | Me | Cl | $OCF_3$ | $CH_3$ |
| A.1.28 | Me | Cl | $OCF_3$ | $CH_2CH_3$ |
| A.1.29 | Me | Cl | $OCF_3$ | $CH_2OCH_3$ |
| A.1.30 | Me | Cl | $OCF_3$ | $CF_3$ |
| A.1.31 | Me | Br | $CF_3$ | H |
| A.1.32 | Me | Br | $CF_3$ | $CH_3$ |
| A.1.33 | Me | Br | $CF_3$ | $CH_2CH_3$ |
| A.1.34 | Me | Br | $CF_3$ | $CH_2OCH_3$ |

TABLE A-continued

Substituent designations for Tables 1 to 44:

| Line | $R_{91}$ | $R_{92}$ | $R_{93}$ | $R_{35}$ |
|---|---|---|---|---|
| A.1.35 | Me | Br | $CF_3$ | $CF_3$ |
| A.1.36 | Me | Br | Br | H |
| A.1.37 | Me | Br | Br | $CH_3$ |
| A.1.38 | Me | Br | Br | $CH_2CH_3$ |
| A.1.39 | Me | Br | Br | $CH_2OCH_3$ |
| A.1.40 | Me | Br | Br | $CF_3$ |
| A.1.41 | Me | Br | Cl | H |
| A.1.42 | Me | Br | Cl | $CH_3$ |
| A.1.43 | Me | Br | Cl | $CH_2CH_3$ |
| A.1.44 | Me | Br | Cl | $CH_2OCH_3$ |
| A.1.45 | Me | Br | Cl | $CF_3$ |
| A.1.46 | Me | Br | $OCF_2H$ | H |
| A.1.47 | Me | Br | $OCF_2H$ | $CH_3$ |
| A.1.48 | Me | Br | $OCF_2H$ | $CH_2CH_3$ |
| A.1.49 | Me | Br | $OCF_2H$ | $CH_2OCH_3$ |
| A.1.50 | Me | Br | $OCF_2H$ | $CF_3$ |
| A.1.51 | Me | Br | $OCH_2CF_3$ | H |
| A.1.52 | Me | Br | $OCH_2CF_3$ | $CH_3$ |
| A.1.53 | Me | Br | $OCH_2CF_3$ | $CH_2CH_3$ |
| A.1.54 | Me | Br | $OCH_2CF_3$ | $CH_2OCH_3$ |
| A.1.55 | Me | Br | $OCH_2CF_3$ | $CF_3$ |
| A.1.56 | Me | Br | $OCF_3$ | H |
| A.1.57 | Me | Br | $OCF_3$ | $CH_3$ |
| A.1.58 | Me | Br | $OCF_3$ | $CH_2CH_3$ |
| A.1.59 | Me | Br | $OCF_3$ | $CH_2OCH_3$ |
| A.1.60 | Me | Br | $OCF_3$ | $CF_3$ |
| A.1.61 | Me | F | $CF_3$ | H |
| A.1.62 | Me | F | $CF_3$ | $CH_3$ |
| A.1.63 | Me | F | $CF_3$ | $CH_2CH_3$ |
| A.1.64 | Me | F | $CF_3$ | $CH_2OCH_3$ |
| A.1.65 | Me | F | $CF_3$ | $CF_3$ |
| A.1.66 | Me | F | Br | H |
| A.1.67 | Me | F | Br | $CH_3$ |
| A.1.68 | Me | F | Br | $CH_2CH_3$ |
| A.1.69 | Me | F | Br | $CH_2OCH_3$ |
| A.1.70 | Me | F | Br | $CF_3$ |
| A.1.71 | Me | F | Cl | H |
| A.1.72 | Me | F | Cl | $CH_3$ |
| A.1.73 | Me | F | Cl | $CH_2CH_3$ |
| A.1.74 | Me | F | Cl | $CH_2OCH_3$ |
| A.1.75 | Me | F | Cl | $CF_3$ |
| A.1.76 | Me | F | $OCF_2H$ | H |
| A.1.77 | Me | F | $OCF_2H$ | $CH_3$ |
| A.1.78 | Me | F | $OCF_2H$ | $CH_2CH_3$ |
| A.1.79 | Me | F | $OCF_2H$ | $CH_2OCH_3$ |
| A.1.80 | Me | F | $OCF_2H$ | $CF_3$ |
| A.1.81 | Me | F | $OCH_2CF_3$ | H |
| A.1.82 | Me | F | $OCH_2CF_3$ | $CH_3$ |
| A.1.83 | Me | F | $OCH_2CF_3$ | $CH_2CH_3$ |
| A.1.84 | Me | F | $OCH_2CF_3$ | $CH_2OCH_3$ |
| A.1.85 | Me | F | $OCH_2CF_3$ | $CF_3$ |
| A.1.86 | Me | F | $OCF_3$ | H |
| A.1.87 | Me | F | $OCF_3$ | $CH_3$ |
| A.1.88 | Me | F | $OCF_3$ | $CH_2CH_3$ |
| A.1.89 | Me | F | $OCF_3$ | $CH_2OCH_3$ |
| A.1.90 | Me | F | $OCF_3$ | $CF_3$ |
| A.1.91 | Me | CN | $CF_3$ | H |
| A.1.92 | Me | CN | $CF_3$ | $CH_3$ |
| A.1.93 | Me | CN | $CF_3$ | $CH_2CH_3$ |
| A.1.94 | Me | CN | $CF_3$ | $CH_2OCH_3$ |
| A.1.95 | Me | CN | $CF_3$ | $CF_3$ |
| A.1.96 | Me | CN | Br | H |
| A.1.97 | Me | CN | Br | $CH_3$ |
| A.1.98 | Me | CN | Br | $CH_2CH_3$ |
| A.1.99 | Me | CN | Br | $CH_2OCH_3$ |
| A.1.100 | Me | CN | Br | $CF_3$ |
| A.1.101 | Me | CN | Cl | H |
| A.1.102 | Me | CN | Cl | $CH_3$ |
| A.1.103 | Me | CN | Cl | $CH_2CH_3$ |
| A.1.104 | Me | CN | Cl | $CH_2OCH_3$ |
| A.1.105 | Me | CN | Cl | $CF_3$ |
| A.1.106 | Me | CN | $OCF_2H$ | H |
| A.1.107 | Me | CN | $OCF_2H$ | $CH_3$ |
| A.1.108 | Me | CN | $OCF_2H$ | $CH_2CH_3$ |
| A.1.109 | Me | CN | $OCF_2H$ | $CH_2OCH_3$ |
| A.1.110 | Me | CN | $OCF_2H$ | $CF_3$ |
| A.1.111 | Me | CN | $OCH_2CF_3$ | H |
| A.1.112 | Me | CN | $OCH_2CF_3$ | $CH_3$ |
| A.1.113 | Me | CN | $OCH_2CF_3$ | $CH_2CH_3$ |
| A.1.114 | Me | CN | $OCH_2CF_3$ | $CH_2OCH_3$ |
| A.1.115 | Me | CN | $OCH_2CF_3$ | $CF_3$ |
| A.1.116 | Me | CN | $OCF_3$ | H |
| A.1.117 | Me | CN | $OCF_3$ | $CH_3$ |
| A.1.118 | Me | CN | $OCF_3$ | $CH_2CH_3$ |
| A.1.119 | Me | CN | $OCF_3$ | $CH_2OCH_3$ |
| A.1.120 | Me | CN | $OCF_3$ | $CF_3$ |
| A.1.121 | Cl | Cl | $CF_3$ | H |
| A.1.122 | Cl | Cl | $CF_3$ | $CH_3$ |
| A.1.123 | Cl | Cl | $CF_3$ | $CH_2CH_3$ |
| A.1.124 | Cl | Cl | $CF_3$ | $CH_2OCH_3$ |
| A.1.125 | Cl | Cl | $CF_3$ | $CF_3$ |
| A.1.126 | Cl | Cl | Br | H |
| A.1.127 | Cl | Cl | Br | $CH_3$ |
| A.1.128 | Cl | Cl | Br | $CH_2CH_3$ |
| A.1.129 | Cl | Cl | Br | $CH_2OCH_3$ |
| A.1.130 | Cl | Cl | Br | $CF_3$ |
| A.1.131 | Cl | Cl | Cl | H |
| A.1.132 | Cl | Cl | Cl | $CH_3$ |
| A.1.133 | Cl | Cl | Cl | $CH_2CH_3$ |
| A.1.134 | Cl | Cl | Cl | $CH_2OCH_3$ |
| A.1.135 | Cl | Cl | Cl | $CF_3$ |
| A.1.136 | Cl | Cl | $OCF_2H$ | H |
| A.1.137 | Cl | Cl | $OCF_2H$ | $CH_3$ |
| A.1.138 | Cl | Cl | $OCF_2H$ | $CH_2CH_3$ |
| A.1.139 | Cl | Cl | $OCF_2H$ | $CH_2OCH_3$ |
| A.1.140 | Cl | Cl | $OCF_2H$ | $CF_3$ |
| A.1.141 | Cl | Cl | $OCH_2CF_3$ | H |
| A.1.142 | Cl | Cl | $OCH_2CF_3$ | $CH_3$ |
| A.1.143 | Cl | Cl | $OCH_2CF_3$ | $CH_2CH_3$ |
| A.1.144 | Cl | Cl | $OCH_2CF_3$ | $CH_2OCH_3$ |
| A.1.145 | Cl | Cl | $OCH_2CF_3$ | $CF_3$ |
| A.1.146 | Cl | Cl | $OCF_3$ | H |
| A.1.147 | Cl | Cl | $OCF_3$ | $CH_3$ |
| A.1.148 | Cl | Cl | $OCF_3$ | $CH_2CH_3$ |
| A.1.149 | Cl | Cl | $OCF_3$ | $CH_2OCH_3$ |
| A.1.150 | Cl | Cl | $OCF_3$ | $CF_3$ |
| A.1.151 | Cl | Br | $CF_3$ | H |
| A.1.152 | Cl | Br | $CF_3$ | $CH_3$ |
| A.1.153 | Cl | Br | $CF_3$ | $CH_2CH_3$ |
| A.1.154 | Cl | Br | $CF_3$ | $CH_2OCH_3$ |
| A.1.155 | Cl | Br | $CF_3$ | $CF_3$ |
| A.1.156 | Cl | Br | Br | H |
| A.1.157 | Cl | Br | Br | $CH_3$ |
| A.1.158 | Cl | Br | Br | $CH_2CH_3$ |
| A.1.159 | Cl | Br | Br | $CH_2OCH_3$ |
| A.1.160 | Cl | Br | Br | $CF_3$ |
| A.1.161 | Cl | Br | Cl | H |
| A.1.162 | Cl | Br | Cl | $CH_3$ |
| A.1.163 | Cl | Br | Cl | $CH_2CH_3$ |
| A.1.164 | Cl | Br | Cl | $CH_2OCH_3$ |
| A.1.165 | Cl | Br | Cl | $CF_3$ |
| A.1.166 | Cl | Br | $OCF_2H$ | H |
| A.1.167 | Cl | Br | $OCF_2H$ | $CH_3$ |
| A.1.168 | Cl | Br | $OCF_2H$ | $CH_2CH_3$ |
| A.1.169 | Cl | Br | $OCF_2H$ | $CH_2OCH_3$ |
| A.1.170 | Cl | Br | $OCF_2H$ | $CF_3$ |
| A.1.171 | Cl | Br | $OCH_2CF_3$ | H |
| A.1.172 | Cl | Br | $OCH_2CF_3$ | $CH_3$ |
| A.1.173 | Cl | Br | $OCH_2CF_3$ | $CH_2CH_3$ |
| A.1.174 | Cl | Br | $OCH_2CF_3$ | $CH_2OCH_3$ |
| A.1.175 | Cl | Br | $OCH_2CF_3$ | $CF_3$ |
| A.1.176 | Cl | Br | $OCF_3$ | H |
| A.1.177 | Cl | Br | $OCF_3$ | $CH_3$ |
| A.1.178 | Cl | Br | $OCF_3$ | $CH_2CH_3$ |
| A.1.179 | Cl | Br | $OCF_3$ | $CH_2OCH_3$ |
| A.1.180 | Cl | Br | $OCF_3$ | $CF_3$ |
| A.1.181 | Cl | F | $CF_3$ | H |
| A.1.182 | Cl | F | $CF_3$ | $CH_3$ |
| A.1.183 | Cl | F | $CF_3$ | $CH_2CH_3$ |
| A.1.184 | Cl | F | $CF_3$ | $CH_2OCH_3$ |
| A.1.185 | Cl | F | $CF_3$ | $CF_3$ |
| A.1.186 | Cl | F | Br | H |

TABLE A-continued

Substituent designations for Tables 1 to 44:

| Line | $R_{91}$ | $R_{92}$ | $R_{93}$ | $R_{35}$ |
|---|---|---|---|---|
| A.1.187 | Cl | F | Br | $CH_3$ |
| A.1.188 | Cl | F | Br | $CH_2CH_3$ |
| A.1.189 | Cl | F | Br | $CH_2OCH_3$ |
| A.1.190 | Cl | F | Br | $CF_3$ |
| A.1.191 | Cl | F | Cl | H |
| A.1.192 | Cl | F | Cl | $CH_3$ |
| A.1.193 | Cl | F | Cl | $CH_2CH_3$ |
| A.1.194 | Cl | F | Cl | $CH_2OCH_3$ |
| A.1.195 | Cl | F | Cl | $CF_3$ |
| A.1.196 | Cl | F | $OCF_2H$ | H |
| A.1.197 | Cl | F | $OCF_2H$ | $CH_3$ |
| A.1.198 | Cl | F | $OCF_2H$ | $CH_2CH_3$ |
| A.1.199 | Cl | F | $OCF_2H$ | $CH_2OCH_3$ |
| A.1.200 | Cl | F | $OCF_2H$ | $CF_3$ |
| A.1.201 | Cl | F | $OCH_2CF_3$ | H |
| A.1.202 | Cl | F | $OCH_2CF_3$ | $CH_3$ |
| A.1.203 | Cl | F | $OCH_2CF_3$ | $CH_2CH_3$ |
| A.1.204 | Cl | F | $OCH_2CF_3$ | $CH_2OCH_3$ |
| A.1.205 | Cl | F | $OCH_2CF_3$ | $CF_3$ |
| A.1.206 | Cl | F | $OCF_3$ | H |
| A.1.207 | Cl | F | $OCF_3$ | $CH_3$ |
| A.1.208 | Cl | F | $OCF_3$ | $CH_2CH_3$ |
| A.1.209 | Cl | F | $OCF_3$ | $CH_2OCH_3$ |
| A.1.210 | Cl | F | $OCF_3$ | $CF_3$ |
| A.1.211 | Cl | CN | $CF_3$ | H |
| A.1.212 | Cl | CN | $CF_3$ | $CH_3$ |
| A.1.213 | Cl | CN | $CF_3$ | $CH_2CH_3$ |
| A.1.214 | Cl | CN | $CF_3$ | $CH_2OCH_3$ |
| A.1.215 | Cl | CN | $CF_3$ | $CF_3$ |
| A.1.216 | Cl | CN | Br | H |
| A.1.217 | Cl | CN | Br | $CH_3$ |
| A.1.218 | Cl | CN | Br | $CH_2CH_3$ |
| A.1.219 | Cl | CN | Br | $CH_2OCH_3$ |
| A.1.220 | Cl | CN | Br | $CF_3$ |
| A.1.221 | Cl | CN | Cl | H |
| A.1.222 | Cl | CN | Cl | $CH_3$ |
| A.1.223 | Cl | CN | Cl | $CH_2CH_3$ |
| A.1.224 | Cl | CN | Cl | $CH_2OCH_3$ |
| A.1.225 | Cl | CN | Cl | $CF_3$ |
| A.1.226 | Cl | CN | $OCF_2H$ | H |
| A.1.227 | Cl | CN | $OCF_2H$ | $CH_3$ |
| A.1.228 | Cl | CN | $OCF_2H$ | $CH_2CH_3$ |
| A.1.229 | Cl | CN | $OCF_2H$ | $CH_2OCH_3$ |
| A.1.230 | Cl | CN | $OCF_2H$ | $CF_3$ |
| A.1.231 | Cl | CN | $OCH_2CF_3$ | H |
| A.1.232 | Cl | CN | $OCH_2CF_3$ | $CH_3$ |
| A.1.233 | Cl | CN | $OCH_2CF_3$ | $CH_2CH_3$ |
| A.1.234 | Cl | CN | $OCH_2CF_3$ | $CH_2OCH_3$ |
| A.1.235 | Cl | CN | $OCH_2CF_3$ | $CF_3$ |
| A.1.236 | Cl | CN | $OCF_3$ | H |
| A.1.237 | Cl | CN | $OCF_3$ | $CH_3$ |
| A.1.238 | Cl | CN | $OCF_3$ | $CH_2CH_3$ |
| A.1.239 | Cl | CN | $OCF_3$ | $CH_2OCH_3$ |
| A.1.240 | Cl | CN | $OCF_3$ | $CF_3$ |
| A.1.241 | Br | Cl | $CF_3$ | H |
| A.1.242 | Br | Cl | $CF_3$ | $CH_3$ |
| A.1.243 | Br | Cl | $CF_3$ | $CH_2CH_3$ |
| A.1.244 | Br | Cl | $CF_3$ | $CH_2OCH_3$ |
| A.1.245 | Br | Cl | $CF_3$ | $CF_3$ |
| A.1.246 | Br | Cl | Br | H |
| A.1.247 | Br | Cl | Br | $CH_3$ |
| A.1.248 | Br | Cl | Br | $CH_2CH_3$ |
| A.1.249 | Br | Cl | Br | $CH_2OCH_3$ |
| A.1.250 | Br | Cl | Br | $CF_3$ |
| A.1.251 | Br | Cl | Cl | H |
| A.1.252 | Br | Cl | Cl | $CH_3$ |
| A.1.253 | Br | Cl | Cl | $CH_2CH_3$ |
| A.1.254 | Br | Cl | Cl | $CH_2OCH_3$ |
| A.1.255 | Br | Cl | Cl | $CF_3$ |
| A.1.256 | Br | Cl | $OCF_2H$ | H |
| A.1.257 | Br | Cl | $OCF_2H$ | $CH_3$ |
| A.1.258 | Br | Cl | $OCF_2H$ | $CH_2CH_3$ |
| A.1.259 | Br | Cl | $OCF_2H$ | $CH_2OCH_3$ |
| A.1.260 | Br | Cl | $OCF_2H$ | $CF_3$ |
| A.1.261 | Br | Cl | $OCH_2CF_3$ | H |
| A.1.262 | Br | Cl | $OCH_2CF_3$ | $CH_3$ |
| A.1.263 | Br | Cl | $OCH_2CF_3$ | $CH_2CH_3$ |
| A.1.264 | Br | Cl | $OCH_2CF_3$ | $CH_2OCH_3$ |
| A.1.265 | Br | Cl | $OCH_2CF_3$ | $CF_3$ |
| A.1.266 | Br | Cl | $OCF_3$ | H |
| A.1.267 | Br | Cl | $OCF_3$ | $CH_3$ |
| A.1.268 | Br | Cl | $OCF_3$ | $CH_2CH_3$ |
| A.1.269 | Br | Cl | $OCF_3$ | $CH_2OCH_3$ |
| A.1.270 | Br | Cl | $OCF_3$ | $CF_3$ |
| A.1.271 | Br | Br | $CF_3$ | H |
| A.1.272 | Br | Br | $CF_3$ | $CH_3$ |
| A.1.273 | Br | Br | $CF_3$ | $CH_2CH_3$ |
| A.1.274 | Br | Br | $CF_3$ | $CH_2OCH_3$ |
| A.1.275 | Br | Br | $CF_3$ | $CF_3$ |
| A.1.276 | Br | Br | Br | H |
| A.1.277 | Br | Br | Br | $CH_3$ |
| A.1.278 | Br | Br | Br | $CH_2CH_3$ |
| A.1.279 | Br | Br | Br | $CH_2OCH_3$ |
| A.1.280 | Br | Br | Br | $CF_3$ |
| A.1.281 | Br | Br | Cl | H |
| A.1.282 | Br | Br | Cl | $CH_3$ |
| A.1.283 | Br | Br | Cl | $CH_2CH_3$ |
| A.1.284 | Br | Br | Cl | $CH_2OCH_3$ |
| A.1.285 | Br | Br | Cl | $CF_3$ |
| A.1.286 | Br | Br | $OCF_2H$ | H |
| A.1.287 | Br | Br | $OCF_2H$ | $CH_3$ |
| A.1.288 | Br | Br | $OCF_2H$ | $CH_2CH_3$ |
| A.1.289 | Br | Br | $OCF_2H$ | $CH_2OCH_3$ |
| A.1.290 | Br | Br | $OCF_2H$ | $CF_3$ |
| A.1.291 | Br | Br | $OCH_2CF_3$ | H |
| A.1.292 | Br | Br | $OCH_2CF_3$ | $CH_3$ |
| A.1.293 | Br | Br | $OCH_2CF_3$ | $CH_2CH_3$ |
| A.1.294 | Br | Br | $OCH_2CF_3$ | $CH_2OCH_3$ |
| A.1.295 | Br | Br | $OCH_2CF_3$ | $CF_3$ |
| A.1.296 | Br | Br | $OCF_3$ | H |
| A.1.297 | Br | Br | $OCF_3$ | $CH_3$ |
| A.1.298 | Br | Br | $OCF_3$ | $CH_2CH_3$ |
| A.1.299 | Br | Br | $OCF_3$ | $CH_2OCH_3$ |
| A.1.300 | Br | Br | $OCF_3$ | $CF_3$ |
| A.1.301 | Br | F | $CF_3$ | H |
| A.1.302 | Br | F | $CF_3$ | $CH_3$ |
| A.1.303 | Br | F | $CF_3$ | $CH_2CH_3$ |
| A.1.304 | Br | F | $CF_3$ | $CH_2OCH_3$ |
| A.1.305 | Br | F | $CF_3$ | $CF_3$ |
| A.1.306 | Br | F | Br | H |
| A.1.307 | Br | F | Br | $CH_3$ |
| A.1.308 | Br | F | Br | $CH_2CH_3$ |
| A.1.309 | Br | F | Br | $CH_2OCH_3$ |
| A.1.310 | Br | F | Br | $CF_3$ |
| A.1.311 | Br | F | Cl | H |
| A.1.312 | Br | F | Cl | $CH_3$ |
| A.1.313 | Br | F | Cl | $CH_2CH_3$ |
| A.1.314 | Br | F | Cl | $CH_2OCH_3$ |
| A.1.315 | Br | F | Cl | $CF_3$ |
| A.1.316 | Br | F | $OCF_2H$ | H |
| A.1.317 | Br | F | $OCF_2H$ | $CH_3$ |
| A.1.318 | Br | F | $OCF_2H$ | $CH_2CH_3$ |
| A.1.319 | Br | F | $OCF_2H$ | $CH_2OCH_3$ |
| A.1.320 | Br | F | $OCF_2H$ | $CF_3$ |
| A.1.321 | Br | F | $OCH_2CF_3$ | H |
| A.1.322 | Br | F | $OCH_2CF_3$ | $CH_3$ |
| A.1.323 | Br | F | $OCH_2CF_3$ | $CH_2CH_3$ |
| A.1.324 | Br | F | $OCH_2CF_3$ | $CH_2OCH_3$ |
| A.1.325 | Br | F | $OCH_2CF_3$ | $CF_3$ |
| A.1.326 | Br | F | $OCF_3$ | H |
| A.1.327 | Br | F | $OCF_3$ | $CH_3$ |
| A.1.328 | Br | F | $OCF_3$ | $CH_2CH_3$ |
| A.1.329 | Br | F | $OCF_3$ | $CH_2OCH_3$ |
| A.1.330 | Br | F | $OCF_3$ | $CF_3$ |
| A.1.331 | Br | CN | $CF_3$ | H |
| A.1.332 | Br | CN | $CF_3$ | $CH_3$ |
| A.1.333 | Br | CN | $CF_3$ | $CH_2CH_3$ |
| A.1.334 | Br | CN | $CF_3$ | $CH_2OCH_3$ |
| A.1.335 | Br | CN | $CF_3$ | $CF_3$ |
| A.1.336 | Br | CN | Br | H |
| A.1.337 | Br | CN | Br | $CH_3$ |
| A.1.338 | Br | CN | Br | $CH_2CH_3$ |

TABLE A-continued

Substituent designations for Tables 1 to 44:

| Line | $R_{91}$ | $R_{92}$ | $R_{93}$ | $R_{35}$ |
|---|---|---|---|---|
| A.1.339 | Br | CN | Br | $CH_2OCH_3$ |
| A.1.340 | Br | CN | Br | $CF_3$ |
| A.1.341 | Br | CN | Cl | H |
| A.1.342 | Br | CN | Cl | $CH_3$ |
| A.1.343 | Br | CN | Cl | $CH_2CH_3$ |
| A.1.344 | Br | CN | Cl | $CH_2OCH_3$ |
| A.1.345 | Br | CN | Cl | $CF_3$ |
| A.1.346 | Br | CN | $OCF_2H$ | H |
| A.1.347 | Br | CN | $OCF_2H$ | $CH_3$ |
| A.1.348 | Br | CN | $OCF_2H$ | $CH_2CH_3$ |
| A.1.349 | Br | CN | $OCF_2H$ | $CH_2OCH_3$ |
| A.1.350 | Br | CN | $OCF_2H$ | $CF_3$ |
| A.1.351 | Br | CN | $OCH_2CF_3$ | H |
| A.1.352 | Br | CN | $OCH_2CF_3$ | $CH_3$ |
| A.1.353 | Br | CN | $OCH_2CF_3$ | $CH_2CH_3$ |
| A.1.354 | Br | CN | $OCH_2CF_3$ | $CH_2OCH_3$ |
| A.1.355 | Br | CN | $OCH_2CF_3$ | $CF_3$ |
| A.1.356 | Br | CN | $OCF_3$ | H |
| A.1.357 | Br | CN | $OCF_3$ | $CH_3$ |
| A.1.358 | Br | CN | $OCF_3$ | $CH_2CH_3$ |
| A.1.359 | Br | CN | $OCF_3$ | $CH_2OCH_3$ |
| A.1.360 | Br | CN | $OCF_3$ | $CF_3$ |
| A.1.361 | Me | H | $CF_3$ | H |
| A.1.362 | Me | H | $CF_3$ | $CH_3$ |
| A.1.363 | Me | H | $CF_3$ | $CH_2CH_3$ |
| A.1.364 | Me | H | $CF_3$ | $CH_2OCH_3$ |
| A.1.365 | Me | H | $CF_3$ | $CF_3$ |
| A.1.366 | Me | H | Br | H |
| A.1.367 | Me | H | Br | $CH_3$ |
| A.1.368 | Me | H | Br | $CH_2CH_3$ |
| A.1.369 | Me | H | Br | $CH_2OCH_3$ |
| A.1.370 | Me | H | Br | $CF_3$ |
| A.1.371 | Me | H | Cl | H |
| A.1.372 | Me | H | Cl | $CH_3$ |
| A.1.373 | Me | H | Cl | $CH_2CH_3$ |
| A.1.374 | Me | H | Cl | $CH_2OCH_3$ |
| A.1.375 | Me | H | Cl | $CF_3$ |
| A.1.376 | Me | H | $OCF_2H$ | H |
| A.1.377 | Me | H | $OCF_2H$ | $CH_3$ |
| A.1.378 | Me | H | $OCF_2H$ | $CH_2CH_3$ |
| A.1.379 | Me | H | $OCF_2H$ | $CH_2OCH_3$ |
| A.1.380 | Me | H | $OCF_2H$ | $CF_3$ |
| A.1.381 | Me | H | $OCH_2CF_3$ | H |
| A.1.382 | Me | H | $OCH_2CF_3$ | $CH_3$ |
| A.1.383 | Me | H | $OCH_2CF_3$ | $CH_2CH_3$ |
| A.1.384 | Me | H | $OCH_2CF_3$ | $CH_2OCH_3$ |
| A.1.385 | Me | H | $OCH_2CF_3$ | $CF_3$ |
| A.1.386 | Me | H | $OCF_3$ | H |
| A.1.387 | Me | H | $OCF_3$ | $CH_3$ |
| A.1.388 | Me | H | $OCF_3$ | $CH_2CH_3$ |
| A.1.389 | Me | H | $OCF_3$ | $CH_2OCH_3$ |
| A.1.390 | Me | H | $OCF_3$ | $CF_3$ |
| A.1.391 | Cl | H | $CF_3$ | H |
| A.1.392 | Cl | H | $CF_3$ | $CH_3$ |
| A.1.393 | Cl | H | $CF_3$ | $CH_2CH_3$ |
| A.1.394 | Cl | H | $CF_3$ | $CH_2OCH_3$ |
| A.1.395 | Cl | H | $CF_3$ | $CF_3$ |
| A.1.396 | Cl | H | Br | H |
| A.1.397 | Cl | H | Br | $CH_3$ |
| A.1.398 | Cl | H | Br | $CH_2CH_3$ |
| A.1.399 | Cl | H | Br | $CH_2OCH_3$ |
| A.1.400 | Cl | H | Br | $CF_3$ |
| A.1.401 | Cl | H | Cl | H |
| A.1.402 | Cl | H | Cl | $CH_3$ |
| A.1.403 | Cl | H | Cl | $CH_2CH_3$ |
| A.1.404 | Cl | H | Cl | $CH_2OCH_3$ |
| A.1.405 | Cl | H | Cl | $CF_3$ |
| A.1.406 | Cl | H | $OCF_2H$ | H |
| A.1.407 | Cl | H | $OCF_2H$ | $CH_3$ |
| A.1.408 | Cl | H | $OCF_2H$ | $CH_2CH_3$ |
| A.1.409 | Cl | H | $OCF_2H$ | $CH_2OCH_3$ |
| A.1.410 | Cl | H | $OCF_2H$ | $CF_3$ |
| A.1.411 | Cl | H | $OCH_2CF_3$ | H |
| A.1.412 | Cl | H | $OCH_2CF_3$ | $CH_3$ |
| A.1.413 | Cl | H | $OCH_2CF_3$ | $CH_2CH_3$ |
| A.1.414 | Cl | H | $OCH_2CF_3$ | $CH_2OCH_3$ |
| A.1.415 | Cl | H | $OCH_2CF_3$ | $CF_3$ |
| A.1.416 | Cl | H | $OCF_3$ | H |
| A.1.417 | Cl | H | $OCF_3$ | $CH_3$ |
| A.1.418 | Cl | H | $OCF_3$ | $CH_2CH_3$ |
| A.1.419 | Cl | H | $OCF_3$ | $CH_2OCH_3$ |
| A.1.420 | Cl | H | $OCF_3$ | $CF_3$ |
| A.1.421 | Me | Cl | $CHF_2$ | H |
| A.1.422 | Me | Cl | $CHF_2$ | $CH_3$ |
| A.1.423 | Me | Cl | $CHF_2$ | $CH_2CH_3$ |
| A.1.424 | Me | Cl | $CHF_2$ | $CH_2OCH_3$ |
| A.1.425 | Me | Cl | $CHF_2$ | $CF_3$ |
| A.1.426 | Me | Br | $CHF_2$ | H |
| A.1.427 | Me | Br | $CHF_2$ | $CH_3$ |
| A.1.428 | Me | Br | $CHF_2$ | $CH_2CH_3$ |
| A.1.429 | Me | Br | $CHF_2$ | $CH_2OCH_3$ |
| A.1.430 | Me | Br | $CHF_2$ | $CF_3$ |
| A.1.431 | Me | CN | $CHF_2$ | H |
| A.1.432 | Me | CN | $CHF_2$ | $CH_3$ |
| A.1.433 | Me | CN | $CHF_2$ | $CH_2CH_3$ |
| A.1.434 | Me | CN | $CHF_2$ | $CH_2OCH_3$ |
| A.1.435 | Me | CN | $CHF_2$ | $CF_3$ |
| A.1.436 | Cl | Cl | $CHF_2$ | H |
| A.1.437 | Cl | Cl | $CHF_2$ | $CH_3$ |
| A.1.438 | Cl | Cl | $CHF_2$ | $CH_2CH_3$ |
| A.1.439 | Cl | Cl | $CHF_2$ | $CH_2OCH_3$ |
| A.1.440 | Cl | Cl | $CHF_2$ | $CF_3$ |
| A.1.441 | Cl | Br | $CHF_2$ | H |
| A.1.442 | Cl | Br | $CHF_2$ | $CH_3$ |
| A.1.443 | Cl | Br | $CHF_2$ | $CH_2CH_3$ |
| A.1.444 | Cl | Br | $CHF_2$ | $CH_2OCH_3$ |
| A.1.445 | Cl | Br | $CHF_2$ | $CF_3$ |
| A.1.446 | Cl | CN | $CHF_2$ | H |
| A.1.447 | Cl | CN | $CHF_2$ | $CH_3$ |
| A.1.448 | Cl | CN | $CHF_2$ | $CH_2CH_3$ |
| A.1.449 | Cl | CN | $CHF_2$ | $CH_2OCH_3$ |
| A.1.450 | Cl | CN | $CHF_2$ | $CF_3$ |
| A.1.451 | Br | Cl | $CHF_2$ | H |
| A.1.452 | Br | Cl | $CHF_2$ | $CH_3$ |
| A.1.453 | Br | Cl | $CHF_2$ | $CH_2CH_3$ |
| A.1.454 | Br | Cl | $CHF_2$ | $CH_2OCH_3$ |
| A.1.455 | Br | Cl | $CHF_2$ | $CF_3$ |
| A.1.456 | Br | Br | $CHF_2$ | H |
| A.1.457 | Br | Br | $CHF_2$ | $CH_3$ |
| A.1.458 | Br | Br | $CHF_2$ | $CH_2CH_3$ |
| A.1.459 | Br | Br | $CHF_2$ | $CH_2OCH_3$ |
| A.1.460 | Br | Br | $CHF_2$ | $CF_3$ |
| A.1.461 | Br | CN | $CHF_2$ | H |
| A.1.462 | Br | CN | $CHF_2$ | $CH_3$ |
| A.1.463 | Br | CN | $CHF_2$ | $CH_2CH_3$ |
| A.1.464 | Br | CN | $CHF_2$ | $CH_2OCH_3$ |
| A.1.465 | Br | CN | $CHF_2$ | $CF_3$ |

TABLE 1

This table discloses the 465 compounds T1.1.1 to T1.1.465 of the formula

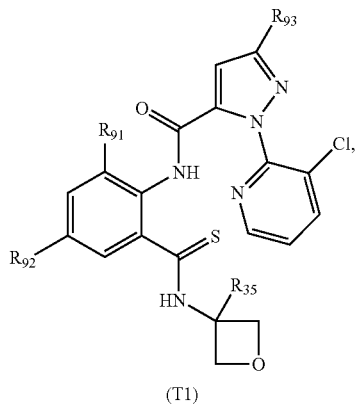

(T1)

in which, for each of these 465 specific compounds, each of the variables $R_{91}$, $R_{92}$, $R_{93}$ and $R_{35}$ has the specific meaning given in the corresponding line, appropriately selected from the 465 lines A.1.1 to A.1.465, of the Table A.

For example, the specific compound T1.1.23 is the compound of the formula T1, in which each of the of the variables $R_{91}$, $R_{92}$, $R_{93}$ and $R_{35}$ has the specific meaning given in the line A.1.23 of the Table A. According to the same system, also all of the other 359 specific compounds disclosed in the Table 1 as well as all of the specific compounds disclosed in the Tables 2 to 44 are specified analogously.

TABLE 2

This table discloses the 465 compounds T2.1.1 to T2.1.465 of the formula

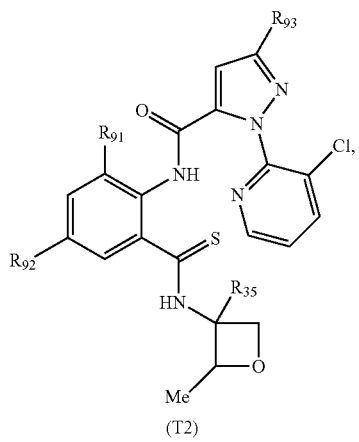

(T2)

in which, for each of these 465 specific compounds, each of the variables $R_{91}$, $R_{92}$, $R_{93}$ and $R_{35}$ has the specific meaning given in the corresponding line, appropriately selected from the 465 lines A.1.1 to A.1.465, of the Table A.

TABLE 3

This table discloses the 465 compounds T3.1.1 to T3.1.465 of the formula

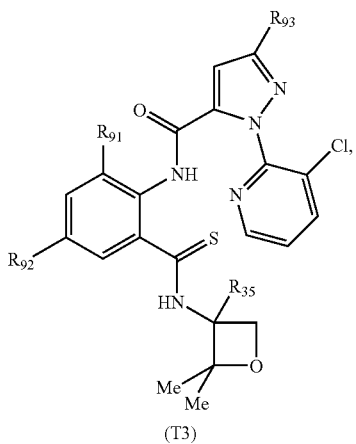

(T3)

in which, for each of these 465 specific compounds, each of the variables $R_{91}$, $R_{92}$, $R_{93}$ and $R_{35}$ has the specific meaning given in the corresponding line, appropriately selected from the 465 lines A.1.1 to A.1.465, of the Table A.

TABLE 4

This table discloses the 465 compounds T4.1.1 to T4.1.465 of the formula

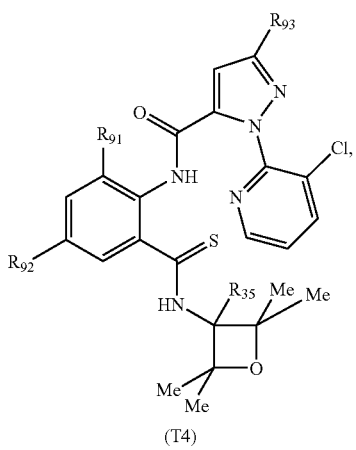

(T4)

in which, for each of these 465 specific compounds, each of the variables $R_{91}$, $R_{92}$, $R_{93}$ and $R_{35}$ has the specific meaning given in the corresponding line, appropriately selected from the 465 lines A.1.1 to A.1.465, of the Table A.

TABLE 5

This table discloses the 465 compounds T5.1.1 to T5.1.465 of the formula

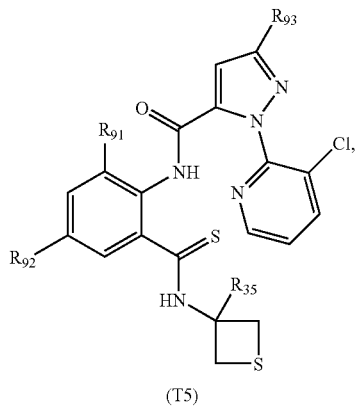

(T5)

in which, for each of these 465 specific compounds, each of the variables $R_{91}$, $R_{92}$, $R_{93}$ and $R_{35}$ has the specific meaning given in the corresponding line, appropriately selected from the 465 lines A.1.1 to A.1.465, of the Table A.

TABLE 6

This table discloses the 465 compounds T6.1.1 to T6.1.465 of the formula

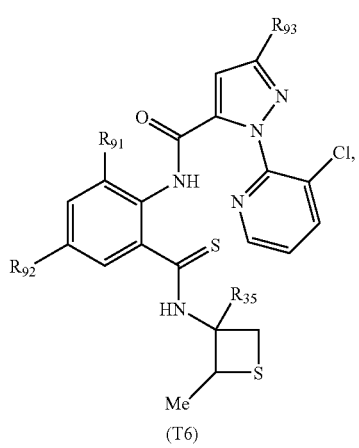

(T6)

in which, for each of these 465 specific compounds, each of the variables $R_{91}$, $R_{92}$, $R_{93}$ and $R_{35}$ has the specific meaning given in the corresponding line, appropriately selected from the 465 lines A.1.1 to A.1.465, of the Table A.

TABLE 7

This table discloses the 465 compounds T7.1.1 to T7.1.465 of the formula

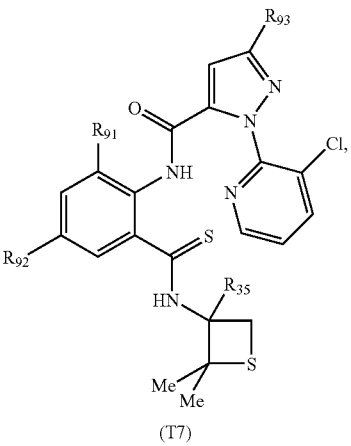

(T7)

in which, for each of these 465 specific compounds, each of the variables $R_{91}$, $R_{92}$, $R_{93}$ and $R_{35}$ has the specific meaning given in the corresponding line, appropriately selected from the 465 lines A.1.1 to A.1.465, of the Table A.

TABLE 8

This table discloses the 465 compounds T8.1.1 to T8.1.465 of the formula

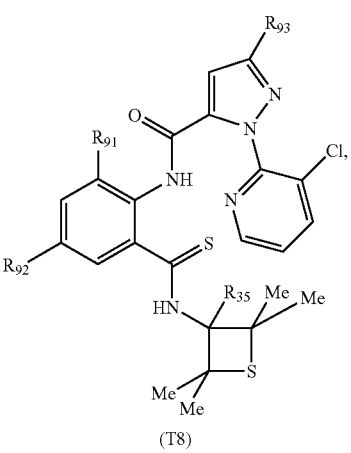

(T8)

in which, for each of these 465 specific compounds, each of the variables $R_{91}$, $R_{92}$, $R_{93}$ and $R_{35}$ has the specific meaning given in the corresponding line, appropriately selected from the 465 lines A.1.1 to A.1.465, of the Table A.

TABLE 9

This table discloses the 465 compounds T9.1.1 to T9.1.465 of the formula

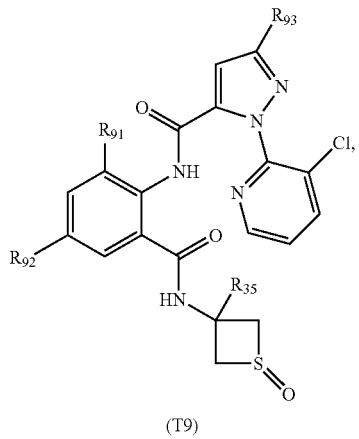

(T9)

in which, for each of these 465 specific compounds, each of the variables $R_{91}$, $R_{92}$, $R_{93}$ and $R_{35}$ has the specific meaning given in the corresponding line, appropriately selected from the 465 lines A.1.1 to A.1.465, of the Table A.

TABLE 10

This table discloses the 465 compounds T10.1.1 to T10.1.465 of the formula

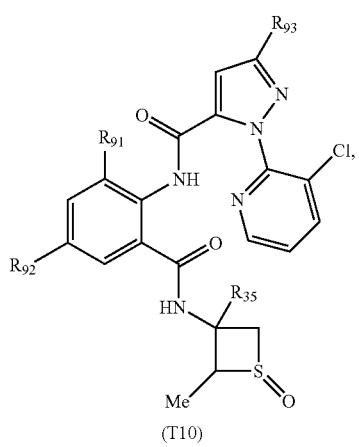

(T10)

in which, for each of these 465 specific compounds, each of the variables $R_{91}$, $R_{92}$, $R_{93}$ and $R_{35}$ has the specific meaning given in the corresponding line, appropriately selected from the 465 lines A.1.1 to A.1.465, of the Table A.

TABLE 11

This table discloses the 465 compounds T11.1.1 to T11.1.465 of the formula

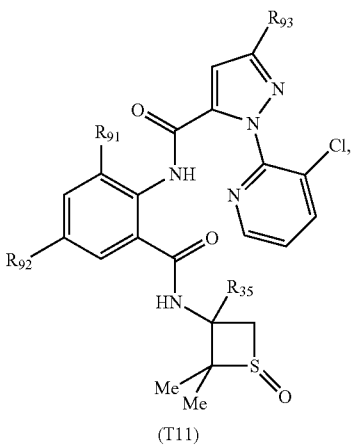

(T11)

in which, for each of these 465 specific compounds, each of the variables $R_{91}$, $R_{92}$, $R_{93}$ and $R_{35}$ has the specific meaning given in the corresponding line, appropriately selected from the 465 lines A.1.1 to A.1.465, of the Table A.

TABLE 12

This table discloses the 465 compounds T12.1.1 to T12.1.465 of the formula

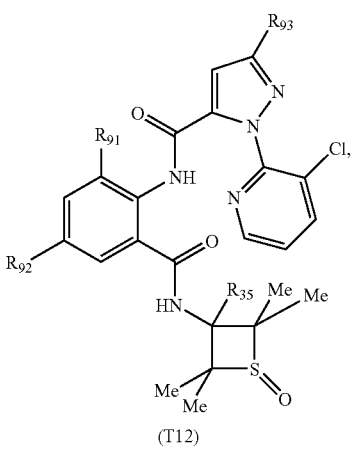

(T12)

in which, for each of these 465 specific compounds, each of the variables $R_{91}$, $R_{92}$, $R_{93}$ and $R_{35}$ has the specific meaning given in the corresponding line, appropriately selected from the 465 lines A.1.1 to A.1.465, of the Table A.

TABLE 13

This table discloses the 465 compounds T13.1.1 to T13.1.465 of the formula

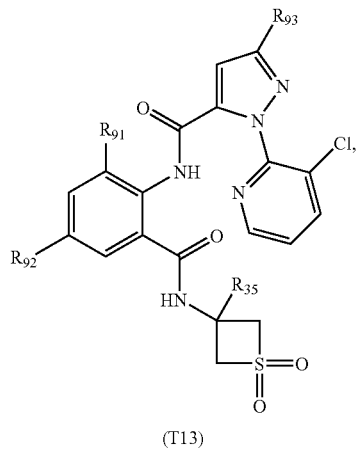

(T13)

in which, for each of these 465 specific compounds, each of the variables $R_{91}$, $R_{92}$, $R_{93}$ and $R_{35}$ has the specific meaning given in the corresponding line, appropriately selected from the 465 lines A.1.1 to A.1.465, of the Table A.

TABLE 14

This table discloses the 465 compounds T14.1.1 to T14.1.465 of the formula

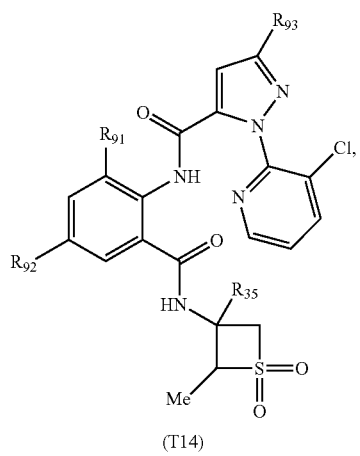

(T14)

in which, for each of these 465 specific compounds, each of the variables $R_{91}$, $R_{92}$, $R_{93}$ and $R_{35}$ has the specific meaning given in the corresponding line, appropriately selected from the 465 lines A.1.1 to A.1.465, of the Table A.

TABLE 15

This table discloses the 465 compounds T15.1.1 to T15.1.465 of the formula

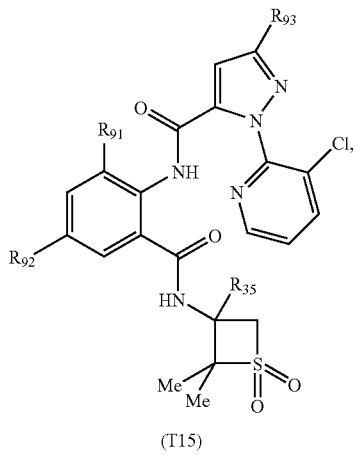

(T15)

in which, for each of these 465 specific compounds, each of the variables $R_{91}$, $R_{92}$, $R_{93}$ and $R_{35}$ has the specific meaning given in the corresponding line, appropriately selected from the 465 lines A.1.1 to A.1.465, of the Table A.

TABLE 16

This table discloses the 465 compounds T16.1.1 to T16.1.465 of the formula

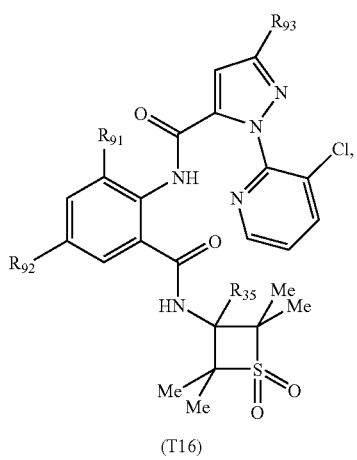

(T16)

in which, for each of these 465 specific compounds, each of the variables $R_{91}$, $R_{92}$, $R_{93}$ and $R_{35}$ has the specific meaning given in the corresponding line, appropriately selected from the 465 lines A.1.1 to A.1.465, of the Table A.

TABLE 17

This table discloses the 465 compounds T17.1.1 to T17.1.465 of the formula

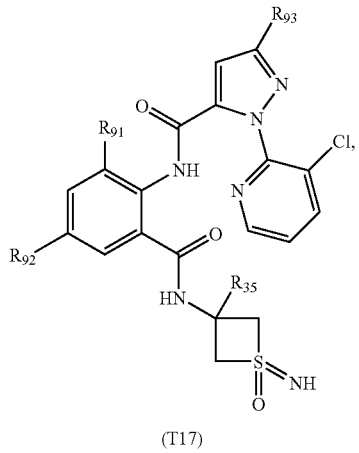

(T17)

in which, for each of these 465 specific compounds, each of the variables $R_{91}$, $R_{92}$, $R_{93}$ and $R_{35}$ has the specific meaning given in the corresponding line, appropriately selected from the 465 lines A.1.1 to A.1.465, of the Table A.

TABLE 18

This table discloses the 465 compounds T18.1.1 to T18.1.465 of the formula

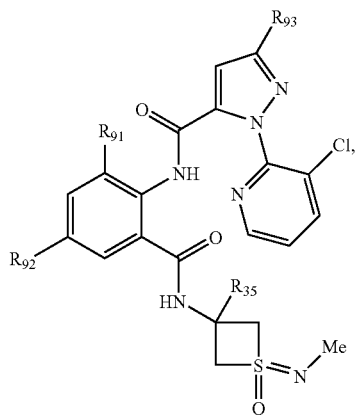

(T18)

in which, for each of these 465 specific compounds, each of the variables $R_{91}$, $R_{92}$, $R_{93}$ and $R_{35}$ has the specific meaning given in the corresponding line, appropriately selected from the 465 lines A.1.1 to A.1.465, of the Table A.

TABLE 19

This table discloses the 465 compounds T19.1.1 to T19.1.465 of the formula

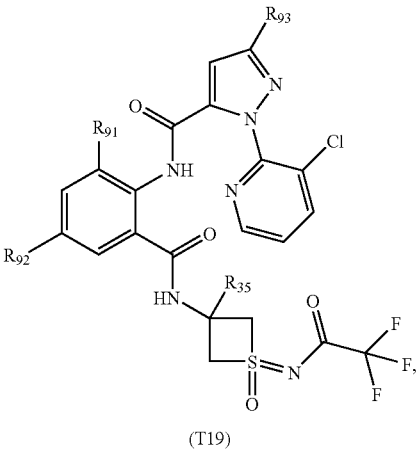

(T19)

in which, for each of these 465 specific compounds, each of the variables $R_{91}$, $R_{92}$, $R_{93}$ and $R_{35}$ has the specific meaning given in the corresponding line, appropriately selected from the 465 lines A.1.1 to A.1.465, of the Table A.

TABLE 20

This table discloses the 465 compounds T20.1.1 to T20.1.465 of the formula

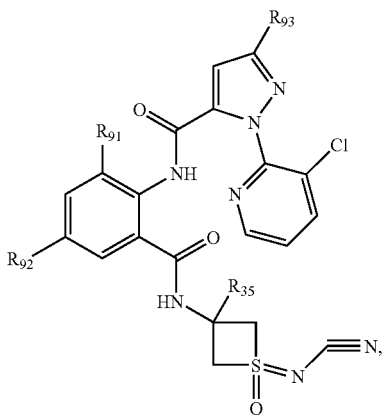

(T20)

in which, for each of these 465 specific compounds, each of the variables $R_{91}$, $R_{92}$, $R_{93}$ and $R_{35}$ has the specific meaning given in the corresponding line, appropriately selected from the 465 lines A.1.1 to A.1.465, of the Table A.

TABLE 21

This table discloses the 465 compounds T21.1.1 to T21.1.465 of the formula

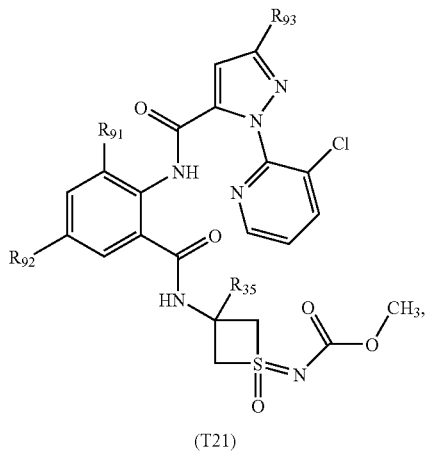

(T21)

in which, for each of these 465 specific compounds, each of the variables $R_{91}$, $R_{92}$, $R_{93}$ and $R_{35}$ has the specific meaning given in the corresponding line, appropriately selected from the 465 lines A.1.1 to A.1.465, of the Table A.

TABLE 22

This table discloses the 465 compounds T22.1.1 to T22.1.465 of the formula

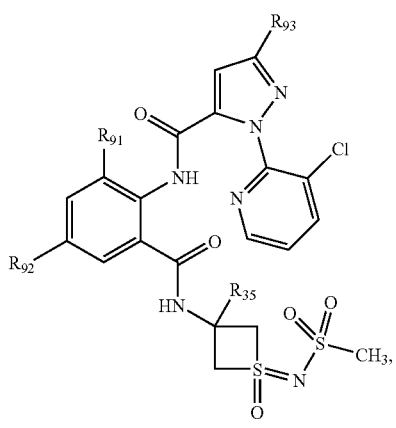

(T22)

in which, for each of these 465 specific compounds, each of the variables $R_{91}$, $R_{92}$, $R_{93}$ and $R_{35}$ has the specific meaning given in the corresponding line, appropriately selected from the 465 lines A.1.1 to A.1.465, of the Table A.

TABLE 23

This table discloses the 465 compounds T23.1.1 to T23.1.465 of the formula

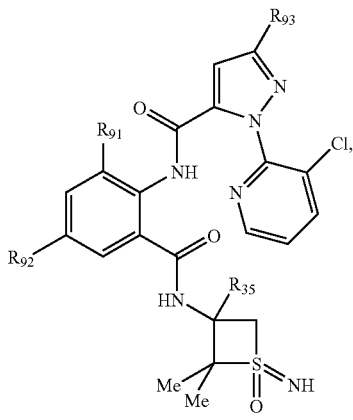

(T23)

in which, for each of these 465 specific compounds, each of the variables $R_{91}$, $R_{92}$, $R_{93}$ and $R_{35}$ has the specific meaning given in the corresponding line, appropriately selected from the 465 lines A.1.1 to A.1.465, of the Table A.

TABLE 24

This table discloses the 465 compounds T24.1.1 to T24.1.465 of the formula

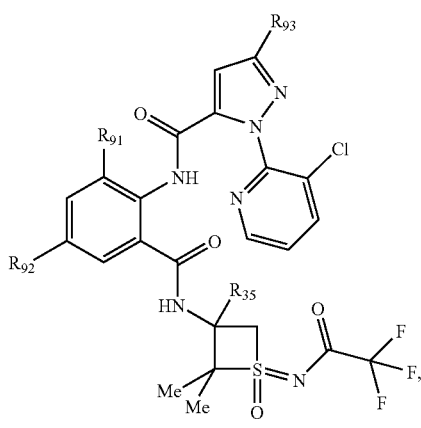

(T24)

in which, for each of these 465 specific compounds, each of the variables $R_{91}$, $R_{92}$, $R_{93}$ and $R_{35}$ has the specific meaning given in the corresponding line, appropriately selected from the 465 lines A.1.1 to A.1.465, of the Table A.

TABLE 25

This table discloses the 465 compounds T25.1.1 to T25.1.465 of the formula

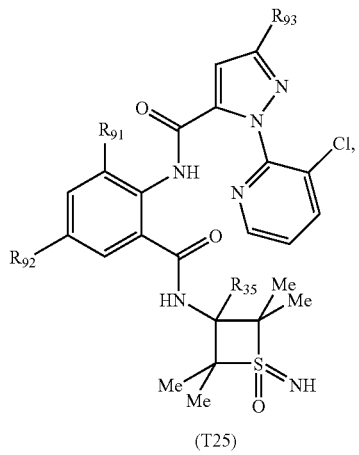

(T25)

in which, for each of these 465 specific compounds, each of the variables $R_{91}$, $R_{92}$, $R_{93}$ and $R_{35}$ has the specific meaning given in the corresponding line, appropriately selected from the 465 lines A.1.1 to A.1.465, of the Table A.

TABLE 26

This table discloses the 465 compounds T26.1.1 to T26.1.465 of the formula

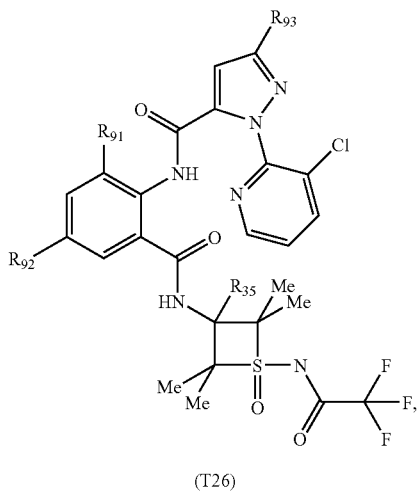

(T26)

in which, for each of these 465 specific compounds, each of the variables $R_{91}$, $R_{92}$, $R_{93}$ and $R_{35}$ has the specific meaning given in the corresponding line, appropriately selected from the 465 lines A.1.1 to A.1.465, of the Table A.

TABLE 27

This table discloses the 465 compounds T27.1.1 to T27.1.465 of the formula

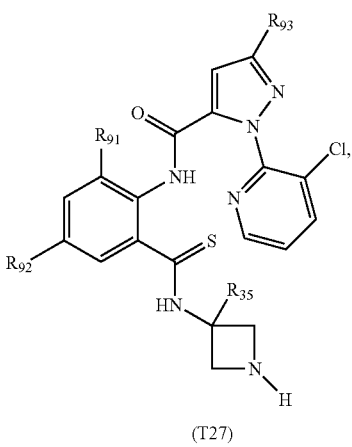

(T27)

in which, for each of these 465 specific compounds, each of the variables $R_{91}$, $R_{92}$, $R_{93}$ and $R_{35}$ has the specific meaning given in the corresponding line, appropriately selected from the 465 lines A.1.1 to A.1.465, of the Table A.

TABLE 28

This table discloses the 465 compounds T28.1.1 to T28.1.465 of the formula

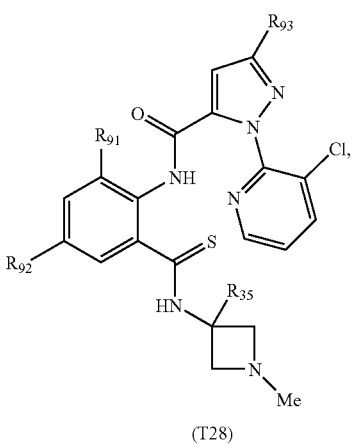

(T28)

in which, for each of these 465 specific compounds, each of the variables $R_{91}$, $R_{92}$, $R_{93}$ and $R_{35}$ has the specific meaning given in the corresponding line, appropriately selected from the 465 lines A.1.1 to A.1.465, of the Table A.

TABLE 29

This table discloses the 465 compounds T29.1.1 to T29.1.465 of the formula

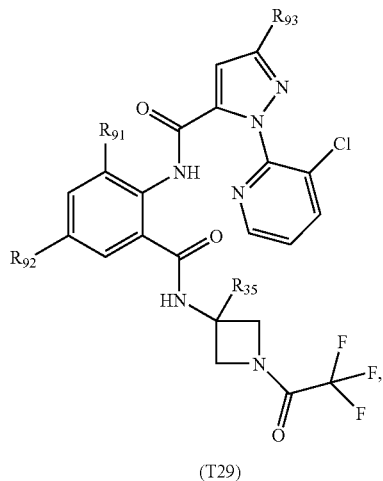

(T29)

in which, for each of these 465 specific compounds, each of the variables $R_{91}$, $R_{92}$, $R_{93}$ and $R_{35}$ has the specific meaning given in the corresponding line, appropriately selected from the 465 lines A.1.1 to A.1.465, of the Table A.

TABLE 30

This table discloses the 465 compounds T30.1.1 to T30.1.465 of the formula

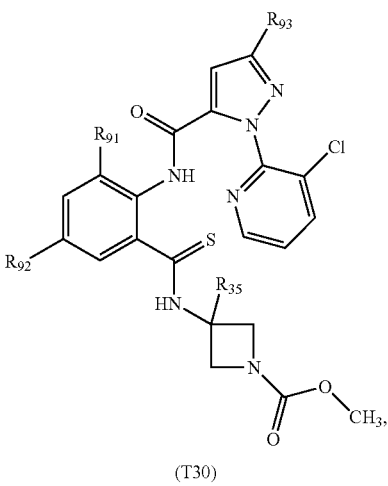

(T30)

in which, for each of these 465 specific compounds, each of the variables $R_{91}$, $R_{92}$, $R_{93}$ and $R_{35}$ has the specific meaning given in the corresponding line, appropriately selected from the 465 lines A.1.1 to A.1.465, of the Table A.

TABLE 31

This table discloses the 465 compounds T31.1.1 to T31.1.465 of the formula

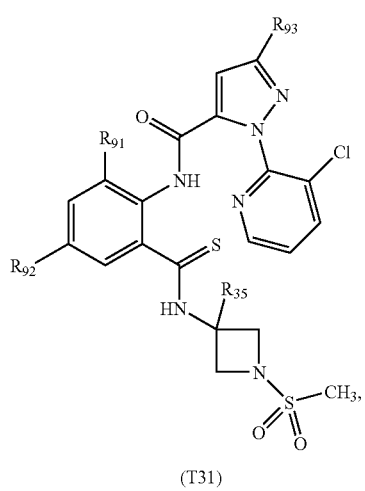

(T31)

in which, for each of these 465 specific compounds, each of the variables $R_{91}$, $R_{92}$, $R_{93}$ and $R_{35}$ has the specific meaning given in the corresponding line, appropriately selected from the 465 lines A.1.1 to A.1.465, of the Table A.

TABLE 32

This table discloses the 465 compounds T32.1.1 to T32.1.465 of the formula

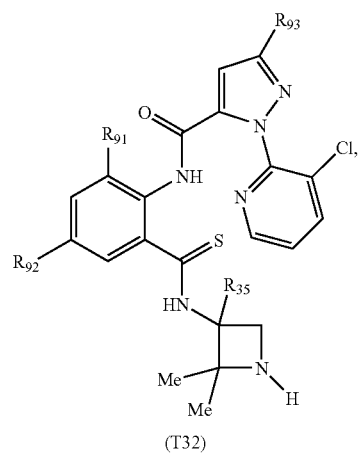

(T32)

in which, for each of these 465 specific compounds, each of the variables $R_{91}$, $R_{92}$, $R_{93}$ and $R_{35}$ has the specific meaning given in the corresponding line, appropriately selected from the 465 lines A.1.1 to A.1.465, of the Table A.

TABLE 33

This table discloses the 465 compounds T33.1.1 to T33.1.465 of the formula

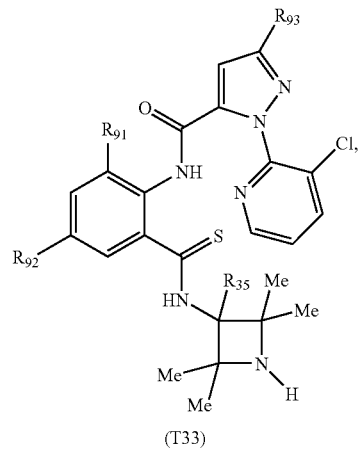

(T33)

in which, for each of these 465 specific compounds, each of the variables $R_{91}$, $R_{92}$, $R_{93}$ and $R_{35}$ has the specific meaning given in the corresponding line, appropriately selected from the 465 lines A.1.1 to A.1.465, of the Table A.

TABLE 34

This table discloses the 465 compounds T34.1.1 to T34.1.465 of the formula

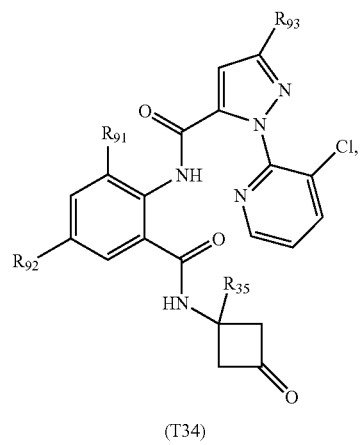

(T34)

in which, for each of these 465 specific compounds, each of the variables $R_{91}$, $R_{92}$, $R_{93}$ and $R_{35}$ has the specific meaning given in the corresponding line, appropriately selected from the 465 lines A.1.1 to A.1.465, of the Table A.

TABLE 35

This table discloses the 465 compounds T35.1.1 to T35.1.465 of the formula

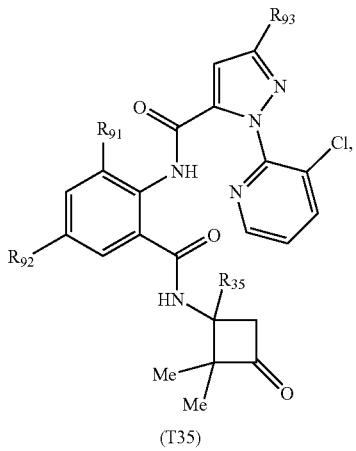

(T35)

in which, for each of these 465 specific compounds, each of the variables $R_{91}$, $R_{92}$, $R_{93}$ and $R_{35}$ has the specific meaning given in the corresponding line, appropriately selected from the 465 lines A.1.1 to A.1.465, of the Table A.

TABLE 36

This table discloses the 465 compounds T36.1.1 to T36.1.465 of the formula

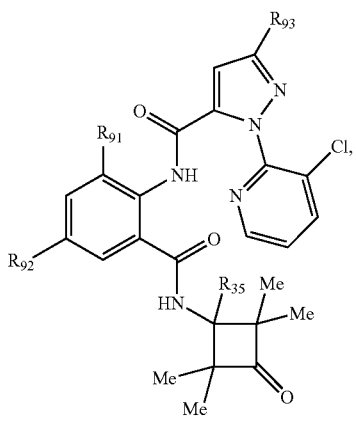

(T36)

in which, for each of these 465 specific compounds, each of the variables $R_{91}$, $R_{92}$, $R_{93}$ and $R_{35}$ has the specific meaning given in the corresponding line, appropriately selected from the 465 lines A.1.1 to A.1.465, of the Table A.

TABLE 37

This table discloses the 465 compounds T37.1.1 to T37.1.465 of the formula

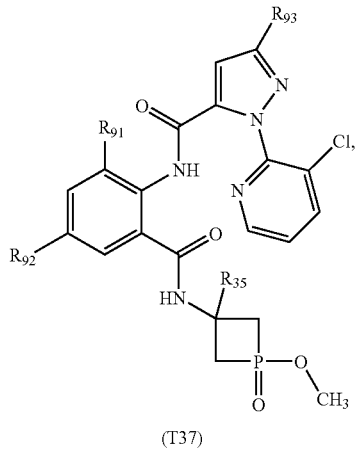

(T37)

in which, for each of these 465 specific compounds, each of the variables $R_{91}$, $R_{92}$, $R_{93}$ and $R_{35}$ has the specific meaning given in the corresponding line, appropriately selected from the 465 tines A.1.1 to A.1.465, of the Table A.

TABLE 38

This table discloses the 465 compounds T38.1.1 to T38.1.465 of the formula

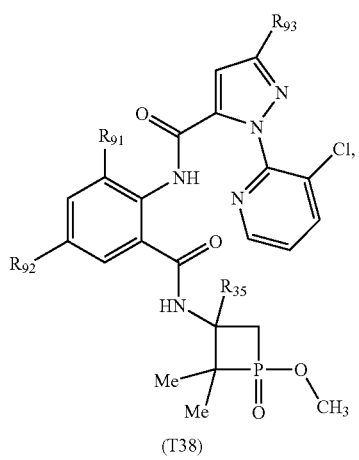

(T38)

in which, for each of these 465 specific compounds, each of the variables $R_{91}$, $R_{92}$, $R_{93}$ and $R_{35}$ has the specific meaning given in the corresponding line, appropriately selected from the 465 lines A.1.1 to A.1.465, of the Table A.

TABLE 39

This table discloses the 465 compounds T39.1.1 to T39.1.465 of the formula

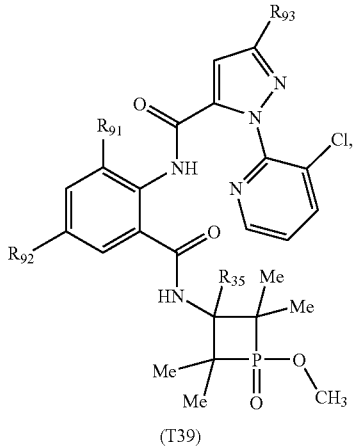

(T39)

in which, for each of these 465 specific compounds, each of the variables $R_{91}$, $R_{92}$, $R_{93}$ and $R_{35}$ has the specific meaning given in the corresponding line, appropriately selected from the 465 lines A.1.1 to A.1.465, of the Table A.

TABLE 40

This table discloses the 465 compounds T40.1.1 to T40.1.465 of the formula

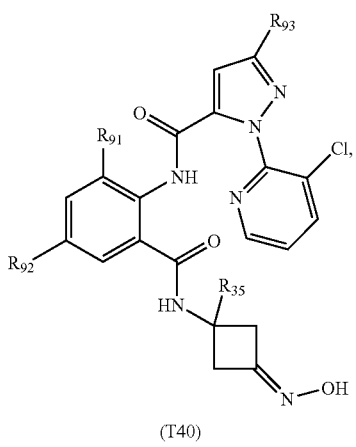

(T40)

in which, for each of these 465 specific compounds, each of the variables $R_{91}$, $R_{92}$, $R_{93}$ and $R_{35}$ has the specific meaning given in the corresponding line, appropriately selected from the 465 lines A.1.1 to A.1.465, of the Table A.

TABLE 41

This table discloses the 465 compounds T41.1.1 to T41.1.465 of the formula

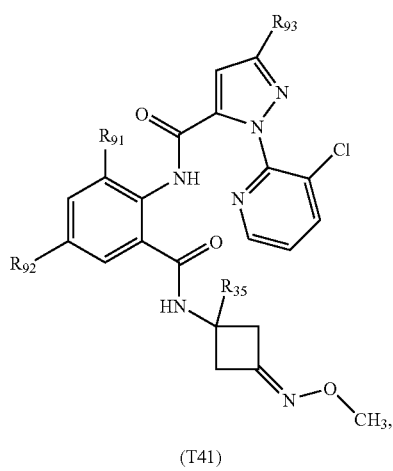

(T41)

in which, for each of these 465 specific compounds, each of the variables $R_{91}$, $R_{92}$, $R_{93}$ and $R_{35}$ has the specific meaning given in the corresponding line, appropriately selected from the 465 lines A.1.1 to A.1.465, of the Table A.

TABLE 42

This table discloses the 465 compounds T42.1.1 to T42.1.465 of the formula

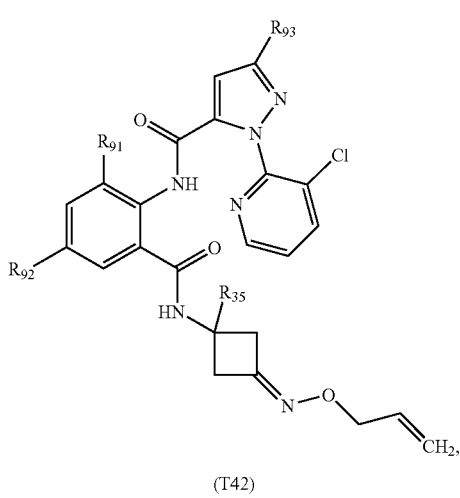

(T42)

in which, for each of these 465 specific compounds, each of the variables $R_{91}$, $R_{92}$, $R_{93}$ and $R_{35}$ has the specific meaning given in the corresponding line, appropriately selected from the 465 lines A.1.1 to A.1.465, of the Table A.

TABLE 43

This table discloses the 465 compounds T43.1.1 to T43.1.465 of the formula

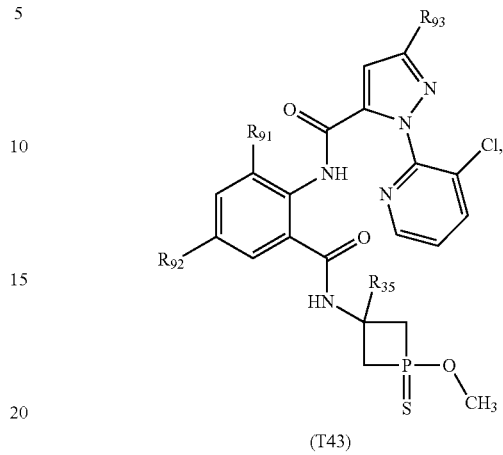

(T43)

in which, for each of these 465 specific compounds, each of the variables $R_{91}$, $R_{92}$, $R_{93}$ and $R_{35}$ has the specific meaning given in the corresponding line, appropriately selected from the 465 lines A.1.1 to A.1.465, of the Table A.

TABLE 44

This table discloses the 465 compounds T44.1.1 to T44.1.465 of the formula

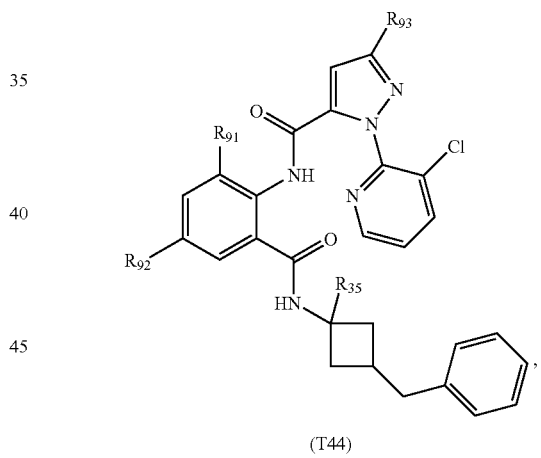

(T44)

in which, for each of these 465 specific compounds, each of the variables $R_{91}$, $R_{92}$, $R_{93}$ and $R_{35}$ has the specific meaning given in the corresponding line, appropriately selected from the 465 lines A.1.1 to A.1.465, of the Table A.

Formulation Examples (%=Percent by Weight)

| Example F1: Emulsion concentrates | a) | b) | c) |
|---|---|---|---|
| Active ingredient | 25% | 40% | 50% |
| Calcium dodecylbenzenesulfonate | 5% | 8% | 6% |
| Castor oil polyethylene glycol ether (36 mol of EO) | 5% | — | — |
| Tributylphenoxypolyethylene glycol ether (30 mol of EO) | — | 12% | 4% |
| Cyclohexanone | — | 15% | 20% |
| Xylene mixture | 65% | 25% | 20% |

Emulsions of any desired concentration can be prepared from such concentrates by dilution with water.

| Example F2: Solutions | a) | b) | c) | d) |
|---|---|---|---|---|
| Active ingredient | 80% | 10% | 5% | 95% |
| Ethylene glycol monomethyl ether | 20% | — | — | — |
| Polyethylene glycol MW 400 | — | 70% | — | — |
| N-Methylpyrrolid-2-one | — | 20% | — | — |
| Epoxidized coconut oil | — | — | 1% | 5% |
| Petroleum ether (boiling range: 160-190°) | — | — | 94% | — |

The solutions are suitable for use in the form of microdrops.

| Example F3: Granules | a) | b) | c) | d) |
|---|---|---|---|---|
| Active ingredient | 5% | 10% | 8% | 21% |
| Kaolin | 94% | — | 79% | 54% |
| Highly disperse silica | 1% | — | 13% | 7% |
| Attapulgite | — | 90% | — | 18% |

The active ingredient is dissolved in dichloromethane, the solution is sprayed onto the carrier(s), and the solvent is subsequently evaporated in vacuo.

| Example F4: Dusts | a) | b) |
|---|---|---|
| Active ingredient | 2% | 5% |
| Highly disperse silica | 1% | 5% |
| Talc | 97% | — |
| Kaolin | — | 90% |

Ready-to-use dusts are obtained by intimately mixing the carriers and the active ingredient.

| Example F5: Wettable powders | a) | b) | c) |
|---|---|---|---|
| Active ingredient | 25% | 50% | 75% |
| Sodium lignosulfonate | 5% | 5% | — |
| Sodium lauryl sulfate | 3% | — | 5% |
| Sodium diisobutylnaphthalenesulfonate | — | 6% | 10% |
| Octylphenoxypolyethylene glycol ether (7-8 mol of EO) | — | 2% | — |
| Highly disperse silica | 5% | 10% | 10% |
| Kaolin | 62% | 27% | — |

The active ingredient is mixed with the additives and the mixture is ground thoroughly in a suitable mill. This gives wettable powders, which can be diluted with water to give suspensions of any desired concentration.

Example F6

Extruder Granules

| Active ingredient | 10% |
|---|---|
| Sodium lignosulfonate | 2% |
| Carboxymethylcellulose | 1% |
| Kaolin | 87% |

The active ingredient is mixed with the additives, and the mixture is ground, moistened with water, extruded, granulated and dried in a stream of air.

Example F7

Coated Granules

| Active ingredient | 3% |
|---|---|
| Polyethylene glycol (MW 200) | 3% |
| Kaolin | 94% |

In a mixer, the finely ground active ingredient is applied uniformly to the kaolin, which has been moistened with the polyethylene glycol. This gives dust-free coated granules.

Example F8

Suspension Concentrate

| Active ingredient | 40% |
|---|---|
| Ethylene glycol | 10% |
| Nonylphenoxypolyethylene glycol ether (15 mol of EO) | 6% |
| Sodium lignosulfonate | 10% |
| Carboxymethylcellulose | 1% |
| 37% aqueous formaldehyde solution | 0.2% |
| Silicone oil (75% aqueous emulsion) | 0.8% |
| Water | 32% |

The finely ground active ingredient is mixed intimately with the additives. Suspensions of any desired concentration can be prepared from the thus resulting suspension concentrate by dilution with water.

The activity of the compounds according to the invention can be broadened considerably, and adapted to prevailing circumstances, by adding other insecticidally or acaricidally active ingredients. Suitable additions to active ingredients here are, for example, representatives of the following classes of active ingredients: organophosphorus compounds, nitrophenol derivatives, thioureas, juvenile hormones, formamidines, benzophenone derivatives, ureas, pyrrole derivatives, carbamates, pyrethroids, chlorinated hydrocarbons, acylureas, pyridylmethyleneamino derivatives, macrolides, neonicotinoids and *Bacillus thuringiensis* preparations.

The following mixtures of the compounds of formula I with active ingredients are preferred (the abbreviation "TX" means: "one compound selected from the group consisting of the compounds specifically described in tables T1 to T44 of the present invention"):

an adjuvant selected from the group of substances consisting of petroleum oils (alternative name) (628)+TX, an acaricide selected from the group of substances consisting of 1,1-bis(4-chloro-phenyl)-2-ethoxyethanol (IUPAC name) (910)+TX, 2,4-dichlorophenyl benzenesulfonate (IUPAC/Chemical Abstracts name) (1059)+TX, 2-fluoro-N-methyl-N-1-naphthylacetamide (IUPAC name) (1295)+TX, 4-chlorophenyl phenyl sulfone (IUPAC name) (981)+TX, abamectin (1)+TX, acequinocyl (3)+TX, acetoprole [CCN]+TX, acrinathrin (9)+TX, aldicarb (16)+TX, aldoxycarb (863)+TX, alpha-cypermethrin (202)+TX, amidithion (870)+TX, amidoflumet [CCN]+TX, amidothioate (872)+TX, amiton (875)+TX, amiton hydrogen oxalate (875)+TX, amitraz (24)+TX, aramite (881)+TX, arsenous oxide (882)+TX, AVI 382 (compound code)+TX, AZ 60541 (compound code)+TX, azinphos-ethyl (44)+TX, azinphos-methyl (45)+TX, azobenzene (IUPAC name) (888)+TX, azocyclotin (46)+TX, azothoate (889)+TX, benomyl (62)+TX, benoxafos (alternative name) [CCN]+TX, benzoximate (71)+TX, benzyl benzoate (IUPAC name) [CCN]+TX, bifenazate (74)+TX, bifenthrin (76)+TX, binapacryl (907)+TX, brofenvalerate (alternative name)+TX, bromocyclen (918)+TX, bromophos (920)+TX, bromophos-ethyl (921)+TX, bromopropylate (94)+TX, buprofezin (99)+TX, butocarboxim (103)+TX, butoxycarboxim (104)+TX, butylpyridaben (alternative name)+TX, calcium polysulfide (IUPAC name) (111)+TX, camphechlor (941)+TX, carbanolate (943)+TX, carbaryl (115)+TX, carbofuran (118)+TX, carbophenothion (947)+TX, CGA 50'439 (development code) (125)+TX, chinomethionat (126)+TX, chlorbenside (959)+TX, chlordimeform (964)+TX, chlordimeform hydrochloride (964)+TX, chlorfenapyr (130)+TX, chlorfenethol (968)+TX, chlorfenson (970)+TX, chlorfensulphide (971)+TX, chlorfenvinphos (131)+TX, chlorobenzilate (975)+TX, chloromebuform (977)+TX, chloromethiuron (978)+TX, chloropropylate (983)+TX, chlorpyrifos (145)+TX, chlorpyrifos-methyl (146)+TX, chlorthiophos (994)+TX, cinerin I (696)+TX, cinerin II (696)+TX, cinerins (696)+TX, clofentezine (158)+TX, closantel (alternative name) [CCN]+TX, coumaphos (174)+TX, crotamiton (alternative name) [CCN]+TX, crotoxyphos (1010)+TX, cufraneb (1013)+TX, cyanthoate (1020)+TX, cyflumetofen (CAS Reg. No.: 400882-07-7)+TX, cyhalothrin (196)+TX, cyhexatin (199)+TX, cypermethrin (201)+TX, DCPM (1032)+TX, DDT (219)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulphon (1039)+TX, diafenthiuron (226)+TX, dialifos (1042)+TX, diazinon (227)+TX, dichlofluanid (230)+TX, dichlorvos (236)+TX, dicliphos (alternative name)+TX, dicofol (242)+TX, dicrotophos (243)+TX, dienochlor (1071)+TX, dimefox (1081)+TX, dimethoate (262)+TX, dinactin (alternative name) (653)+TX, dinex (1089)+TX, dinex-diclexine (1089)+TX, dinobuton (269)+TX, dinocap (270)+TX, dinocap-4 [CCN]+TX, dinocap-6 [CCN]+TX, dinocton (1090)+TX, dinopenton (1092)+TX, dinosulfon (1097)+TX, dinoterbon (1098)+TX, dioxathion (1102)+TX, diphenyl sulfone (IUPAC name) (1103)+TX, disulfiram (alternative name) [CCN]+TX, disulfoton (278)+TX, DNOC (282)+TX, dofenapyn (1113)+TX, doramectin (alternative name) [CCN]+TX, endosulfan (294)+TX, endothion (1121)+TX, EPN (297)+TX, eprinomectin (alternative name) [CCN]+TX, ethion (309)+TX, ethoate-methyl (1134)+TX, etoxazole (320)+TX, etrimfos (1142)+TX, fenazaflor (1147)+TX, fenazaquin (328)+TX, fenbutatin oxide (330)+TX, fenothiocarb (337)+TX, fenpropathrin (342)+TX, fenpyrad (alternative name)+TX, fenpyroximate (345)+TX, fenson (1157)+TX, fentrifanil (1161)+TX, fenvalerate (349)+TX, fipronil (354)+TX, fluacrypyrim (360)+TX, fluazuron (1166)+TX, flubenzimine (1167)+TX, flucycloxuron (366)+TX, flucythrinate (367)+TX, fluenetil (1169)+TX, flufenoxuron (370)+TX, flumethrin (372)+TX, fluorbenside (1174)+TX, fluvalinate (1184)+TX, FMC 1137 (development code) (1185)+TX, formetanate (405)+TX, formetanate hydrochloride (405)+TX, formothion (1192)+TX, formparanate (1193)+TX, gamma-HCH (430)+TX, glyodin (1205)+TX, halfenprox (424)+TX, heptenophos (432)+TX, hexadecyl cyclopropanecarboxylate (IUPAC/Chemical Abstracts name) (1216)+TX, hexythiazox (441)+TX, iodomethane (IUPAC name) (542)+TX, isocarbophos (alternative name) (473)+TX, isopropyl O-(methoxyaminothiophosphoryl)salicylate (IUPAC name) (473)+TX, ivermectin (alternative name) [CCN]+TX, jasmolin I (696)+TX, jasmolin II (696)+TX, jodfenphos (1248)+TX, lindane (430)+TX, lufenuron (490)+TX, malathion (492)+TX, malonoben (1254)+TX, mecarbam (502)+TX, mephosfolan (1261)+TX, mesutfen (alternative name) [CCN]+TX, methacrifos (1266)+TX, methamidophos (527)+TX, methidathion (529)+TX, methiocarb (530)+TX, methomyl (531)+TX, methyl bromide (537)+TX, metolcarb (550)+TX, mevinphos (556)+TX, mexacarbate (1290)+TX, milbemectin (557)+TX, milbemycin oxime (alternative name) [CCN]+TX, mipafox (1293)+TX, monocrotophos (561)+TX, morphothion (1300)+TX, moxidectin (alternative name) [CCN]+TX, naled (567)+TX, NC-184 (compound code)+TX, NC-512 (compound code)+TX, nifluridide (1309)+TX, nikkomycins (alternative name) [CCN]+TX, nitrilacarb (1313)+TX, nitrilacarb 1:1 zinc chloride complex (1313)+TX, NNI-0101 (compound code)+TX, NNI-0250 (compound code)+TX, omethoate (594)+TX, oxamyl (602)+TX, oxydeprofos (1324)+TX, oxydisulfoton (1325)+TX, pp-DDT (219)+TX, parathion (615)+TX, permethrin (626)+TX, petroleum oils (alternative name) (628)+TX, phenkapton (1330)+TX, phenthoate (631)+TX, phorate (636)+TX, phosalone (637)+TX, phosfolan (1338)+TX, phosmet (638)+TX, phosphamidon (639)+TX, phoxim (642)+TX, pirimiphos-methyl (652)+TX, polychloroterpenes (traditional name) (1347)+TX, polynactins (alternative name) (653)+TX, proclonol (1350)+TX, profenofos (662)+TX, promacyl (1354)+TX, propargite (671)+TX, propetamphos (673)+TX, propoxur (678)+TX, prothidathion (1360)+TX, prothoate (1362)+TX, pyrethrin I (696)+TX, pyrethrin II (696)+TX, pyrethrins (696)+TX, pyridaben (699)+TX, pyridaphenthion (701)+TX, pyrimidifen (706)+TX, pyrimitate (1370)+TX, quinalphos (711)+TX, quintiofos (1381)+TX, R-1492 (development code) (1382)+TX, RA-17 (development code) (1383)+TX, rotenone (722)+TX, schradan (1389)+TX, sebufos (alternative name)+TX, selamectin (alternative name) [CCN]+TX, SI-0009 (compound code)+TX, sophamide (1402)+TX, spirodiclofen (738)+TX, spiromesifen (739)+TX, SSI-121 (development code) (1404)+TX, sulfiram (alternative name) [CCN]+TX, sulfluramid (750)+TX, sulfotep (753)+TX, sulfur (754)+TX, SZI-121 (development code) (757)+TX, tau-fluvalinate (398)+TX, tebufenpyrad (763)+TX, TEPP (1417)+TX, terbam (alternative name)+TX, tetrachlorvinphos (777)+TX, tetradifon (786)+TX, tetranactin (alternative name) (653)+TX, tetrasul (1425)+TX, thiafenox (alternative name)+TX, thiocarboxime (1431)+TX, thiofanox (800)+TX, thiometon (801)+TX, thioquinox (1436)+TX, thuringiensin (alternative name) [CCN]+TX, triamiphos (1441)+TX, triarathene (1443)+TX, triazophos (820)+TX, triazuron (alternative name)+TX, trichlorfon (824)+TX, trifenofos (1455)+TX, trinactin (alternative name) (653)+TX, vamidothion (847)+TX, vaniliprole [CCN] and YI-5302 (compound code)+TX, an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX, an anthelmintic selected from the group of substances consisting of abamectin (1)+TX, crufomate (1011)+TX, doramectin (alternative name) [CCN]+TX, emamectin (291)+

TX, emamectin benzoate (291)+TX, eprinomectin (alternative name) [CCN]+TX, ivermectin (alternative name) [CCN]+TX, milbemycin oxime (alternative name) [CCN]+TX, moxidectin (alternative name) [CCN]+TX, piperazine [CCN]+TX, selamectin (alternative name) [CCN]+TX, spinosad (737) and thiophanate (1435)+TX, an avicide selected from the group of substances consisting of chloralose (127)+TX, endrin (1122)+TX, fenthion (346)+TX, pyridin-4-amine (IUPAC name) (23) and strychnine (745)+TX, a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen (alternative name) [CCN]+TX, kasugamycin (483)+TX, kasugamycin hydrochloride hydrate (483)+TX, nickel bis(dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal (alternative name) [CCN]+TX, a biological agent selected from the group of substances consisting of *Adoxophyes orana* GV (alternative name) (12)+TX, *Agrobacterium radiobacter* (alternative name) (13)+TX, *Amblyseius* spp. (alternative name) (19)+TX, *Anagrapha falcifera* NPV (alternative name) (28)+TX, *Anagrus atomus* (alternative name) (29)+TX, *Aphelinus abdominalis* (alternative name) (33)+TX, *Aphidius colemani* (alternative name) (34)+TX, *Aphidoletes aphidimyza* (alternative name) (35)+TX, *Autographa califomica* NPV (alternative name) (38)+TX, *Bacillus firmus* (alternative name) (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. *kurstaki* (scientific name) (51)+TX, *Bacillus thuringiensis* subsp. *tenebrionis* (scientific name) (51)+TX, *Beauveria bassiana* (alternative name) (53)+TX, *Beauveria brongniartii* (alternative name) (54)+TX, *Chrysoperla camea* (alternative name) (151)+TX, *Cryptolaemus montrouzieri* (alternative name) (178)+TX, *Cydia pomonella* GV (alternative name) (191)+TX, *Dacnusa sibirica* (alternative name) (212)+TX, *Diglyphus isaea* (alternative name) (254)+TX, *Encarsia formosa* (scientific name) (293)+TX, *Eretmocerus eremicus* (alternative name) (300)+TX, *Helicoverpa zea* NPV (alternative name) (431)+TX, *Heterorhabditis bacteriophora* and *H. megidis* (alternative name) (433)+TX, *Hippodamia convergens* (alternative name) (442)+TX, *Leptomastix dactylopii* (alternative name) (488)+TX, *Macrolophus caliginosus* (alternative name) (491)+TX, *Mamestra brassicae* NPV (alternative name) (494)+TX, *Metaphycus helvolus* (alternative name) (522)+TX, *Metarhizium anisopliae* var. *acridum* (scientific name) (523)+TX, *Metarhizium anisopliae* var. *anisopliae* (scientific name) (523)+TX, *Neodiprion sertifer* NPV and *N. lecontei* NPV (alternative name) (575)+TX, *Onus* spp. (alternative name) (596)+TX, *Paecilomyces fumosoroseus* (alternative name) (613)+TX, *Phytoseiulus persimilis* (alternative name) (644)+TX, *Spodoptera exigua* multicapsid nuclear polyhedrosis virus (scientific name) (741)+TX, *Steinernema bibionis* (alternative name) (742)+TX, *Steinernema carpocapsae* (alternative name) (742)+TX, *Steinernema feltiae* (alternative name) (742)+TX, *Steinernema glaseri* (alternative name) (742)+TX, *Steinemema riobrave* (alternative name) (742)+TX, *Steinernema riobravis* (alternative name) (742)+TX, *Steinernema scapterisci* (alternative name) (742)+TX, *Steinemema* spp. (alternative name) (742)+TX, *Trichogramma* spp. (alternative name) (826)+TX, *Typhlodromus occidentalis* (alternative name) (844) and *Verticillium lecanii* (alternative name) (848)+TX, a soil sterilant selected from the group of substances consisting of iodomethane (IUPAC name) (542) and methyl bromide (537)+TX, a chemosterilant selected from the group of substances consisting of apholate [CCN]+TX, bisazir (alternative name) [CCN]+TX, busulfan (alternative name) [CCN]+TX, diflubenzuron (250)+TX, dimatif (alternative name) [CCN]+TX, hemel [CCN]+TX, hempa [CCN]+TX, metepa [CCN]+TX, methiotepa [CCN]+TX, methyl apholate [CCN]+TX, morzid [CCN]+TX, penfluron (alternative name) [CCN]+TX, tepa [CCN]+TX, thiohempa (alternative name) [CCN]+TX, thiotepa (alternative name) [CCN]+TX, tretamine (alternative name) [CCN] and uredepa (alternative name) [CCN]+TX, an insect pheromone selected from the group of substances consisting of (E)-dec-5-en-1-ylacetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E+TX, Z)-tetradeca-4+TX, 10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (2)-hexadec-11-en-1-ylacetate (IUPAC name) (437)+TX, (Z)-hexadec-13-en-11-yn-1-ylacetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E+TX, 9Z)-dodeca-7+TX, 9-dien-1-ylacetate (IUPAC name) (283)+TX, (9Z+TX, 11E)-tetradeca-9+TX, 11-dien-1-ylacetate (IUPAC name) (780)+TX, (9Z+TX, 12E)-tetradeca-9+TX, 12-dien-1-ylacetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin (alternative name) [CCN]+TX, brevicomin (alternative name) [CCN]+TX, codlelure (alternative name) [CCN]+TX, codlemone (alternative name) (167)+TX, cuelure (alternative name) (179)+TX, disparlure (277)+TX, dodec-8-en-1-ylacetate (IUPAC name) (286)+TX, dodec-9-en-1-yl acetate (IUPAC name) (287)+TX, dodeca-8+TX, 10-dien-1-ylacetate (IUPAC name) (284)+TX, dominicalure (alternative name) [CCN]+TX, ethyl 4-methyloctanoate (IUPAC name) (317)+TX, eugenol (alternative name) [CCN]+TX, frontalin (alternative name) [CCN]+TX, gossyplure (alternative name) (420)+TX, grandlure (421)+TX, grandlure I (alternative name) (421)+TX, grandlure II (alternative name) (421)+TX, grandlure III (alternative name) (421)+TX, grandlure IV (alternative name) (421)+TX, hexalure [CCN]+TX, ipsdienol (alternative name) [CCN]+TX, ipsenol (alternative name) [CCN]+TX, japonilure (alternative name) (481)+TX, lineatin (alternative name) [CCN]+TX, litlure (alternative name) [CCN]+TX, looplure (alternative name) [CCN]+TX, medlure [CCN]+TX, megatomoic acid (alternative name) [CCN]+TX, methyl eugenol (alternative name) (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure (alternative, name) [CCN]+TX, oryctalure (alternative name) (317)+TX, ostramone (alternative name) [CCN]+TX, siglure [CCN]+TX, sordidin (alternative name) (736)+TX, sulcatol (alternative name) [CCN]+TX, tetradec-11-en-1-yl acetate (IUPAC name) (785)+TX, trimedlure (839)+TX, trimedlure A (alternative name) (839)+TX, trimedlure B₁ (alternative name) (839)+TX, trimedlure B₂ (alternative name) (839)+TX, trimedlure C (alternative name) (839) and trunc-call (alternative name) [CCN]+TX, an insect repellent selected from the group of substances consisting of 2-(octylthio)-ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquin-butyl (1276)+TX, methylneodecanamide [CCN]+TX, oxamate [CCN] and picaridin [CCN]+TX, an insecticide selected from the group of substances consisting of 1-dichloro-1-nitroethane (IUPAC/Chemical Abstracts name) (1058)+TX, 1,1-dichloro-2,2-bis(4-ethylphenyl)ethane (IUPAC name) (1056)+TX, 1,2-dichloropropane (IUPAC/Chemical Abstracts name) (1062)+TX, 1,2-dichloropropane with 1,3-dichloropropene (IUPAC name) (1063)+TX, 1-bromo-2-chloroethane (IUPAC/Chemical Abstracts name) (916)+TX, 2,2,2-trichloro-1-(3,4-dichlorophenyl)ethyl acetate (IUPAC name) (1451)+TX, 2,2-dichlorovinyl 2-ethylsulfinylethyl methyl phosphate (IUPAC name) (1066)+TX, 2-(1,3-dithiolan-2-yl)phenyl dimethylcarbamate (IUPAC/Chemical Abstracts name) (1109)+TX, 2-(2-butoxyethoxy)ethyl thiocyanate (IUPAC/Chemical Abstracts name) (935)+TX, 2-(4,5-dimethyl-1,3-dioxolan-2-yl)phenyl methylcarbamate (IUPAC/Chemical Abstracts name) (1084)+TX, 2-(4-chloro-3,5-xylyloxy)ethanol (IUPAC name) (986)+TX, 2-chlorovinyl diethyl phosphate (IUPAC name) (984)+TX, 2-imidazolidone (IUPAC name) (1225)+TX, 2-isovalerylindan-1,3-dione (IUPAC name) (1246)+TX, 2-methyl(prop-2-ynyl)aminophenyl methylcarbamate (IUPAC name) (1284)+TX, 2-thiocyanatoethyl laurate (IUPAC name) (1433)+TX, 3-bromo-1-chloroprop-1-ene (IUPAC name) (917)+TX, 3-methyl-1-phenylpyrazol-5-yl dimethylcarbamate (IUPAC name) (1283)+TX, 4-methyl(prop-2-ynyl)amino-3,5-xylyl methylcarbamate (IUPAC name) (1285)+TX, 5,5-dimethyl-3-oxocyclohex-1-enyl dimethylcarbamate (IUPAC name) (1085)+TX, abamectin (1)+TX, acephate (2)+TX, acetamiprid (4)+TX, acethion (alternative name) [CCN]+TX, acetoprole [CCN]+TX, acrinathrin (9)+TX, acrylonitrile (IUPAC name) (861)+TX, alanycarb (15)+TX, aldicarb (16)+TX, aldoxycarb (863)+TX, aldrin (864)+TX, allethrin (17)+TX, allosamidin (alternative name) [CCN]+TX, allyxycarb (866)+TX, alpha-cypermethrin (202)+TX, alpha-ecdysone (alternative name) [CCN]+TX, aluminium phosphide (640)+TX, amidithion (870)+TX, amidothioate (872)+TX, aminocarb (873)+TX, amiton (875)+TX, amiton hydrogen oxalate (875)+TX, amitraz (24)+TX, anabasine (877)+TX, athidathion (883)+TX, AVI 382 (compound code)+TX, AZ 60541 (compound code)+TX, azadirachtin (alternative name) (41)+TX, azamethiphos (42)+TX, azinphos-ethyl (44)+TX, azinphos-methyl (45)+TX, azothoate (889)+TX, *Bacillus thuringiensis* delta endotoxins (alternative name) (52)+TX, barium hexafluorosilicate (alternative name) [CCN]+TX, barium polysulfide (IUPAC/Chemical Abstracts name) (892)+TX, barthrin [CCN]+TX, Bayer 22/190 (development code) (893)+TX, Bayer 22408 (development code) (894)+TX, bendiocarb (58)+TX, benfuracarb (60)+TX, bensultap (66)+TX, beta-cyfluthrin (194)+TX, beta-cypermethrin (203)+TX, bifenthrin (76)+TX, bioallethrin (78)+TX, bioallethrin S-cyclopentenyl isomer (alternative name) (79)+TX, bioethanomethrin [CCN]+TX, biopermethrin (908)+TX, bioresmethrin (80)+TX, bis(2-chloroethyl) ether (IUPAC name) (909)+TX, bistrifluron (83)+TX, borax (86)+TX, brofenvalerate (alternative name)+TX, bromfenvinfos (914)+TX, bromocyclen (918)+TX, bromo-DDT (alternative name) [CCN]+TX, bromophos (920)+TX, bromophos-ethyl (921)+TX, bufencarb (924)+TX, buprofezin (99)+TX, butacarb (926)+TX, butathiofos (927)+TX, butocarboxim (103)+TX, butonate (932)+TX, butoxycarboxim (104)+TX, butylpyridaben (alternative name)+TX, cadusafos (109)+TX, calcium arsenate [CCN]+TX, calcium cyanide (444)+TX, calcium polysulfide (IUPAC name) (111)+TX, camphechlor (941)+TX, carbanolate (943)+TX, carbaryl (115)+TX, carbofuran (118)+TX, carbon disulfide (IUPAC/Chemical Abstracts name) (945)+TX, carbon tetrachloride (IUPAC name) (946)+TX, carbophenothion (947)+TX, carbosulfan (119)+TX, cartap (123)+TX, cartap hydrochloride (123)+TX, cevadine (alternative name) (725)+TX, chlorbicyclen (960)+TX, chlordane (128)+TX, chlordecone (963)+TX, chlordimeform (964)+TX, chlordimeform hydrochloride (964)+TX, chlorethoxyfos (129)+TX, chlorfenapyr (130)+TX, chlorfenvinphos (131)+TX, chlorfluazuron (132)+TX, chlormephos (136)+TX, chloroform [CCN]+TX, chloropicrin (141)+TX, chlorphoxim (989)+TX, chlorprazophos (990)+TX, chlorpyrifos (145)+TX, chlorpyrifos-methyl (146)+TX, chlorthiophos (994)+TX, chromafenozide (150)+TX, cinerin I (696)+TX, cinerin II (696)+TX, cinerins (696)+TX, cis-resmethrin (alternative name)+TX, cismethrin (80)+TX, clocythrin (alternative name)+TX, cloethocarb (999)+TX, closantel (alternative name) [CCN]+TX, clothianidin (165)+TX, copper acetoarsenite [CCN]+TX, copper arsenate [CCN]+TX, copper oleate [CCN]+TX, coumaphos (174)+TX, coumithoate (1006)+TX, crotamiton (alternative name) [CCN]+TX, crotoxyphos (1010)+TX, crufomate (1011)+TX, cryolite (alternative name) (177)+TX, CS 708 (development code) (1012)+TX, cyanofenphos (1019)+TX, cyanophos (184)+TX, cyanthoate (1020)+TX, cyclethrin [CCN]+TX, cycloprothrin (188)+TX, cyfluthrin (193)+TX, cyhalothrin (196)+TX, cypermethrin (201)+TX, cyphenothrin (206)+TX, cyromazine (209)+TX, cythioate (alternative name) [CCN]+TX, d-limonene (alternative name) [CCN]+TX, d-tetramethrin (alternative name) (788)+TX, DAEP (1031)+TX, dazomet (216)+TX, DDT (219)+TX, decarbofuran (1034)+TX, deltamethrin (223)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulphon (1039)+TX, diafenthiuron (226)+TX, dialifos (1042)+TX, diamidafos (1044)+TX, diazinon (227)+TX, dicapthon (1050)+TX, dichlofenthion (1051)+TX, dichlorvos (236)+TX, dicliphos (alternative name)+TX, dicresyl (alternative name) [CCN]+TX, dicrotophos (243)+TX, dicyclanil (244)+TX, dieldrin (1070)+TX, diethyl 5-methylpyrazol-3-yl phosphate (IUPAC name) (1076)+TX, diflubenzuron (250)+TX, dilor (alternative name) [CCN]+TX, dimefluthrin [CCN]+TX, dimefox (1081)+TX, dimetan (1085)+TX, dimethoate (262)+TX, dimethrin (1083)+TX, dimethylvinphos (265)+TX, dimetilan (1086)+TX, dinex (1089)+TX, dinex-diclexine (1089)+TX, dinoprop (1093)+TX, dinosam (1094)+TX, dinoseb (1095)+TX, dinotefuran (271)+TX, diofenolan (1099)+TX, dioxabenzofos (1100)+TX, dioxacarb (1101)+TX, dioxathion (1102)+TX, disulfoton (278)+TX, dithicrofos (1108)+TX, DNOC (282)+TX, doramectin (alternative name) [CCN]+TX, DSP (1115)+TX, ecdysterone (alternative name) [CCN]+TX, El 1642 (development code) (1118)+TX, emamectin (291)+TX, emamectin benzoate (291)+TX, EMPC (1120)+TX, empenthrin (292)+TX, endosulfan (294)+TX, endothion (1121)+TX, endrin (1122)+TX, EPBP (1123)+TX, EPN (297)+TX, epofenonane (1124)+TX, eprinomectin (alternative name) [CCN]+TX, esfenvalerate (302)+TX, etaphos (alternative name) [CCN]+TX, ethiofencarb (308)+TX, ethion (309)+TX, ethiprole (310)+TX, ethoate-methyl (1134)+TX, ethoprophos (312)+TX, ethyl formate (IUPAC name) [CCN]+TX, ethyl-DDD (alternative name) (1056)+TX, ethylene dibromide (316)+TX, ethylene dichloride (chemical name) (1136)+TX, ethylene oxide [CCN]+TX, etofenprox (319)+TX, etrimfos (1142)+TX, EXD (1143)+TX, famphur (323)+TX, fenamiphos (326)+TX, fenazaflor (1147)+TX, fenchlorphos (1148)+TX, fenethacarb (1149)+TX, fenfluthrin (1150)+TX, fenitrothion (335)+TX, fenobucarb (336)+TX, fenoxacrim (1153)+TX, fenoxycarb (340)+TX, fenpirithrin (1155)+TX, fenpropathrin (342)+TX, fenpyrad (alternative name)+TX, fensulfothion (1158)+TX, fenthion (346)+TX, fenthion-ethyl [CCN]+TX, fenvalerate (349)+TX, fipronil (354)+TX, flonicamid (358)+TX, flubendiamide (CAS. Reg. No.: 272451-65-7)+TX, flucofuron (1168)+TX, flucycloxuron (366)+TX, flucythrinate (367)+TX, fluenetil (1169)+TX, flufenerim [CCN]+TX, flufenoxuron (370)+TX, flufenprox (1171)+TX, flumethrin (372)+TX, fluvalinate (1184)+TX, FMC 1137 (development code) (1185)+TX, fonofos (1191)+TX, formetanate (405)+TX, formetanate hydrochloride (405)+TX, formothion (1192)+TX, formparanate (1193)+TX, fosmethilan (1194)+TX, fospirate (1195)+TX, fosthiazate (408)+TX, fosthietan (1196)+TX, furathiocarb (412)+TX, furethrin (1200)+TX, gamma-cyhalothrin (197)+TX, gamma-HCH (430)+TX, guazatine (422)+TX, guazatine acetates (422)+TX, GY-81 (development code) (423)+TX, halfenprox (424)+TX, halofenozide (425)+TX, HCH (430)+TX, HEOD (1070)+TX, heptachlor (1211)+TX, heptenophos (432)+TX, heterophos [CCN]+TX, hexaflumuron (439)+TX, HHDN (864)+TX, hydramethylnon (443)+TX, hydrogen cyanide (444)+TX, hydroprene (445)+TX, hyquincarb (1223)+TX, imidacloprid (458)+TX, imiprothrin (460)+TX, indoxacarb (465)+TX, iodomethane (IUPAC name) (542)+TX, IPSP (1229)+TX, isazofos (1231)+TX, isobenzan (1232)+TX, isocarbophos (alternative name) (473)+TX, isodrin (1235)+TX, isofenphos (1236)+TX, isolane (1237)+TX, isoprocarb (472)+TX, isopropyl O-(methoxyaminothiophosphoryl)salicylate (IUPAC name) (473)+TX, isoprothiolane (474)+TX, isothioate (1244)+TX, isoxathion (480)+TX, ivermectin (alternative name) [CCN]+TX, jasmolin I (696)+TX, jasmolin II (696)+TX, jodfenphos (1248)+TX, juvenile hormone I (alternative name) [CCN]+TX, juvenile hormone II (alternative name) [CCN]+TX, juvenile hormone III (alternative name) [CCN]+TX, kelevan (1249)+TX, kinoprene (484)+TX, lambda-cyhalothrin (198)+TX, lead arsenate [CCN]+TX, lepimectin (CCN)+TX, leptophos (1250)+TX, lindane (430)+TX, lirimfos (1251)+TX, lufenuron (490)+TX, lythidathion (1253)+TX, m-cumenyl methylcarbamate (IUPAC name) (1014)+TX, magnesium phosphide (IUPAC name) (640)+TX, malathion (492)+TX, malonoben (1254)+TX, mazidox (1255)+TX, mecarbam (502)+TX, mecarphon (1258)+TX, menazon (1260)+TX, mephosfolan (1261)+TX, mercurous chloride (513)+TX, mesulfenfos (1263)+TX, metaflumizone (CCN)+TX, metam (519)+TX, metam-potassium (alternative name) (519)+TX, metam-sodium (519)+TX, methacrifos (1266)+TX, methamidophos (527)+TX, methanesulfonyl fluoride (IUPAC/Chemical Abstracts name) (1268)+TX, methidathion (529)+TX, methiocarb (530)+TX, methocrotophos (1273)+TX, methomyl (531)+TX, methoprene (532)+TX, methoquin-butyl (1276)+TX, methothrin (alternative name) (533)+TX, methoxychlor (534)+TX, methoxyfenozide (535)+TX, methyl bromide (537)+TX, methyl isothiocyanate (543)+TX, methylchloroform (alternative name) [CCN]+TX, methylene chloride [CCN]+TX, metofluthrin [CCN]+TX, metolcarb (550)+TX, metoxadiazone (1288)+TX, mevinphos (556)+TX, mexacarbate (1290)+TX, milbemectin (557)+TX, milbemycin oxime (alternative name) [CCN]+TX, mipafox (1293)+TX, mirex (1294)+TX, monocrotophos (561)+TX, morphothion (1300)+TX, moxidectin (alternative name) [CCN]+TX, naftalofos (alternative name) [CCN]+TX, naled (567)+TX, naphthalene (IUPAC/Chemical Abstracts name) (1303)+TX, NC-170 (development code) (1306)+TX, NC-184 (compound code)+TX, nicotine (578)+TX, nicotine sulfate (578)+TX, nifluridide (1309)+TX, nitenpyram (579)+TX, nithiazine (1311)+TX, nitrilacarb (1313)+TX, nitrilacarb 1:1 zinc chloride complex (1313)+TX, NNI-0101 (compound code)+TX, NNI-0250 (compound code)+TX, nornicotine (traditional name) (1319)+TX, novaluron (585)+TX, noviflumuron (586)+TX, O-5-dichloro-4-iodophenyl O-ethyl ethylphosphonothioate (IUPAC name) (1057)+TX, O,O-diethyl O-4-methyl-2-oxo-2H-chromen-7-yl phosphorothioate (IUPAC name) (1074)+TX, O,O-diethyl O-6-methyl-2-propylpyrimidin-4-yl phosphorothioate (IUPAC name) (1075)+TX, O,O,O,O-tetrapropyl dithiopyrophosphate (IUPAC name) (1424)+TX, oleic acid (IUPAC name) (593)+TX, omethoate (594)+TX, oxamyl (602)+TX, oxydemeton-methyl (609)+TX, oxydeprofos (1324)+TX, oxydisulfoton (1325)+TX, pp'-DDT (219)+TX, para-dichlorobenzene [CCN]+TX, parathion (615)+TX, parathion-methyl (616)+TX, penfluron (alternative name) [CCN]+TX, pentachlorophenol (623)+TX, pentachlorophenyl laurate (IUPAC name) (623)+TX, permethrin (626)+TX, petroleum oils (alternative name) (628)+TX, PH 60-38 (development code) (1328)+TX, phenkapton (1330)+TX, phenothrin (630)+TX, phenthoate (631)+TX, phorate (636)+TX, phosalone (637)+TX, phosfolan (1338)+TX, phosmet (638)+TX, phosnichlor (1339)+TX, phosphamidon (639)+TX, phosphine (IUPAC name) (640)+TX, phoxim (642)+TX, phoxim-methyl (1340)+TX, pirimetaphos (1344)+TX, pirimicarb (651)+TX, pirimiphos-ethyl (1345)+TX, pirimiphos-methyl (652)+TX, polychlorodicyclopentadiene isomers (IUPAC name) (1346)+TX, polychloroterpenes (traditional name) (1347)+TX, potassium arsenite [CCN]+TX, potassium thiocyanate [CCN]+TX, prallethrin (655)+TX, precocene I (alternative name) [CCN]+TX, precocene II (alternative name) [CCN]+TX, precocene III (alternative name) [CCN]+TX, primidophos (1349)+TX, profenofos (662)+TX, profluthrin [CCN]+TX, promacyl (1354)+TX, promecarb (1355)+TX, propaphos (1356)+TX, propetamphos (673)+TX, propoxur (678)+TX, prothidathion (1360)+TX, prothiofos (686)+TX, prothoate (1362)+TX, protrifenbute [CCN]+TX, pymetrozine (688)+TX, pyraclofos (689)+TX, pyrazophos (693)+TX, pyresmethrin (1367)+TX, pyrethrin I (696)+TX, pyrethrin II (696)+TX, pyrethrins (696)+TX, pyridaben (699)+TX, pyridalyl (700)+TX, pyridaphenthion (701)+TX, pyrimidifen (706)+TX, pyrimitate (1370)+TX, pyriproxyfen (708)+TX, quassia (alternative name) [CCN]+TX, quinalphos (711)+TX, quinalphos-methyl (1376)+TX, quinothion (1380)+TX, quintiofos (1381)+TX, R-1492 (development code) (1382)+TX, rafoxanide (alternative name) [CCN]+TX, resmethrin (719)+TX, rotenone (722)+TX, RU 15525 (development code) (723)+TX, RU 25475 (development code) (1386)+TX, ryania (alternative name) (1387)+TX, ryanodine (traditional name) (1387)+TX, sabadilla (alternative name) (725)+TX, schradan (1389)+TX, sebufos (alternative name)+TX, selamectin (alternative name) [CCN]+TX, SI-0009 (compound code)+TX, SI-0205 (compound code)+TX, SI-0404 (compound code)+TX, SI-0405 (compound code)+TX, silafluofen (728)+TX, SN 72129 (development code) (1397)+TX, sodium arsenite [CCN]+TX, sodium cyanide (444)+TX, sodium fluoride (IUPAC/Chemical Abstracts name) (1399)+TX, sodium hexafluorosilicate (1400)+TX, sodium pentachlorophenoxide (623)+TX, sodium selenate (IUPAC name) (1401)+TX, sodium thiocyanate [CCN]+TX, sophamide (1402)+TX, spinosad (737)+TX, spiromesifen (739)+TX, spirotetrmat (CCN)+TX, sulcofuron (746)+TX, sulcofuron-sodium (746)+TX, sulfluramid (750)+TX, sulfotep (753)+TX, sulfuryl fluoride (756)+TX, sulprofos (1408)+TX, tar oils (alternative name) (758)+TX, tau-fluvalinate (398)+TX, tazimcarb (1412)+TX, TDE (1414)+TX, tebufenozide (762)+TX, tebufenpyrad (763)+TX, tebupirimfos (764)+TX, teflubenzuron (768)+TX, tefluthrin (769)+TX, temephos (770)+TX, TEPP (1417)+TX, terallethrin (1418)+TX, terbam (alternative name)+TX, terbufos (773)+TX, tetrachloroethane [CCN]+TX, tetrachlorvinphos (777)+TX, tetramethrin (787)+TX, theta-cypermethrin (204)+TX, thiacloprid (791)+TX, thiafenox (alternative name)+TX, thiamethoxam (792)+TX, thicrofos (1428)+TX, thiocarboxime (1431)+TX, thiocyclam (798)+TX, thiocyclam hydrogen oxalate (798)+TX, thiodicarb (799)+TX, thiofanox (800)+TX, thiometon (801)+TX, thionazin (1434)+TX, thiosultap (803)+TX, thiosultap-sodium (803)+TX, thuringiensin (alternative name) [CCN]+TX, tolfenpyrad (809)+TX, tralomethrin (812)+TX, transfluthrin (813)+TX, transpermethrin (1440)+TX, triamiphos (1441)+TX, triazamate (818)+TX, triazophos (820)+TX, triazuron (alternative name)+TX, trichlorfon (824)+TX, trichlormetaphos-3 (alternative name) [CCN]+TX, trichloronat (1452)+TX, trifenofos (1455)+TX, triflumuron (835)+TX, trimethacarb (840)+TX, triprene (1459)+TX, vamidothion (847)+TX, vaniliprole [CON]+TX, veratridine (alternative name) (725)+TX, veratrine (alternative name) (725)+TX, XMC (853)+TX, xylylcarb (854)+TX, YI-5302 (compound code)+TX, zeta-cypermethrin (205)+TX, zetamethrin (alternative name)+TX, zinc phosphide (640)+TX, zolaprofos (1469) and ZXI 8901 (development code) (858)+TX, a molluscicide selected from the group of substances consisting of bis(tributyltin) oxide (IUPAC name) (913)+TX, bromoacetamide [CCN]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, a nematicide selected from the group of substances consisting of AKD-3088 (compound code)+TX, 1,2-dibromo-3-chloropropane (IUPAC/Chemical Abstracts name) (1045)+TX, 1,2-dichloiopropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (alternative name) (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben (alternative name)+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, cytokinins (alternative name) (210)+TX, dazomet (216)+TX, DBCP (1045)+TX, DCIP (218)+TX, diamidafos (1044)+TX, dichlofenthion (1051)+TX, dicliphos (alternative name)+TX, dimethoate (262)+TX, doramectin (alternative name) [CCN]+TX, emamectin (291)+TX, emamectin benzoate (291)+TX, eprinomectin (alternative name) [CCN]+TX, ethoprophos (312)+TX, ethylene dibromide (316)+TX, fenamiphos (326)+TX, fenpyrad (alternative name)+TX, fensulfothion (1158)+TX, fosthiazate (408)+TX, fosthietan (1196)+TX, furfural (alternative name) [CCN]+TX, GY-81 (development code) (423)+TX, heterophos [CCN]+TX, iodomethane (IUPAC name) (542)+TX, isamidofos (1230)+TX, isazofos (1231)+TX, ivermectin (alternative name) [CCN]+TX, kinetin (alternative name) (210)+TX, mecarphon (1258)+TX, metam (519)+TX, metam-potassium (alternative name) (519)+TX, metam-sodium (519)+TX, methyl bromide (537)+TX, methyl isothiocyanate (543)+TX, milbemycin oxime (alternative name) [CCN]+TX, moxidectin (alternative name) [CCN]+TX, *Myrothecium verrucaria* composition (alternative name) (565)+TX, NC-184 (compound code)+TX, oxamyl (602)+TX, phorate (636)+TX, phosphamidon (639)+TX, phosphocarb [CCN]+TX, sebufos (alternative name)+TX, selamectin (alternative name) [CCN]+TX, spinosad (737)+TX, terbam (alternative name)+TX, terbufos (773)+TX, tetrachlorothiophene (IUPAC/Chemical Abstracts name) (1422)+TX, thiafenox (alternative name)+TX, thionazin (1434)+TX, triazophos (820)+TX, triazuron (alternative name)+TX, xylenols [CCN]+TX, YI-5302 (compound code) and zeatin (alternative name) (210)+TX, a nitrification inhibitor selected from the group of substances consisting of potassium ethylxanthate [CCN] and nitrapyrin (580)+TX, a plant activator selected from the group of substances consisting of acibenzolar (6)+TX, acibenzolar-S-methyl (6)+TX, probenazole (658) and *Reynoutria sachalinensis* extract (alternative name) (720)+TX, a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CON]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (91)+TX, bromethalin (92)+TX, calcium cyanide (444)+TX, chloralose (127)+TX, chlorophacinone (140)+TX, cholecalciferol (alternative name) (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CON]+TX, sodium cyanide (444)+TX, sodium fluoroacetate (735)+TX, strychnine (745)+TX, thallium sulfate [CCN]+TX, warfarin (851) and zinc phosphide (640)+TX, a synergist selected from the group of substances consisting of 2-(2-butoxyethoxy)-ethyl piperonylate (IUPAC name) (934)+TX, 5-(1,3-benzodioxol-5-yl)-3-hexylcyclohex-2-enone (IUPAC name) (903)+TX, farnesol with nerolidol (alternative name) (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesasmolin (1394) and sulfoxide (1406)+TX, an animal repellent selected from the group of substances consisting of anthraquinone (32)+TX, chloralose (127)+TX, copper naphthenate [CON]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CON] and ziram (856)+TX, a virucide selected from the group of substances consisting of imanin (alternative name) [CON] and ribavirin (alternative name) [CON]+TX, a wound protectant selected from the group of substances consisting of mercuric oxide (512)+TX, octhilinone (590) and thiophanate-methyl (802)+TX, an insecticide selected from the group consisting of the compound of formula A-1 the formula A-3

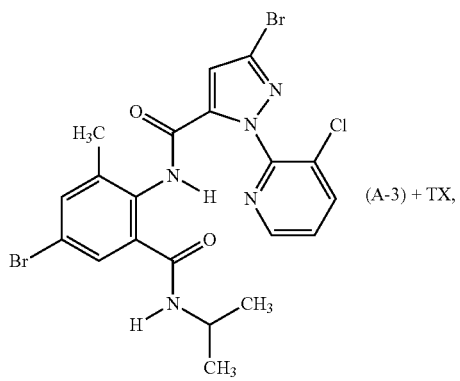

(A-3) + TX, the formula A-4

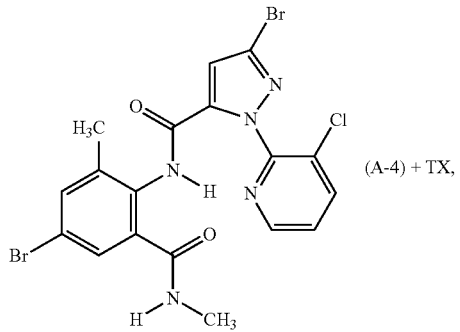

(A-4) + TX, the formula A-5

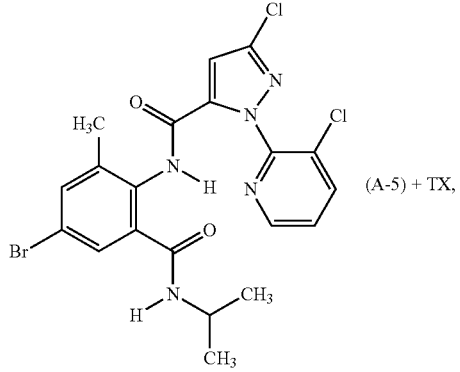

(A-5) + TX, the formula A-2

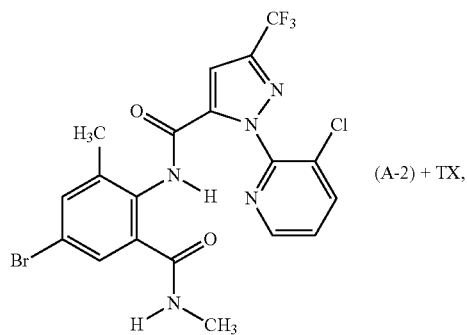

(A-2) + TX, the formula A-6

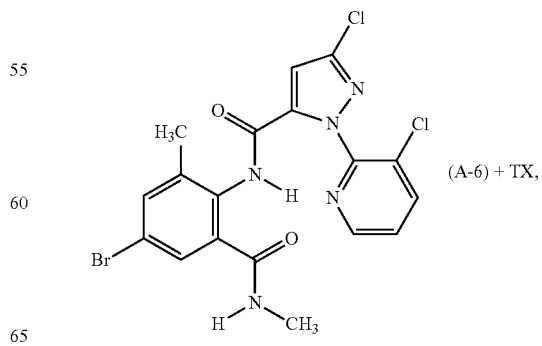

(A-6) + TX, the formula A-7
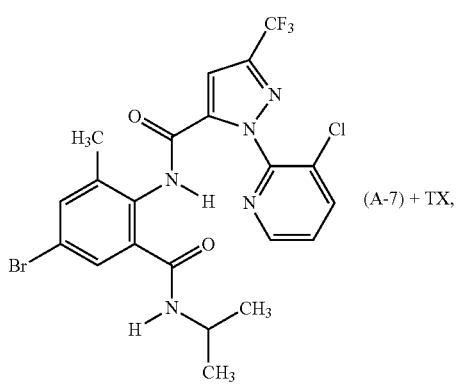
(A-7) + TX,
the formula A-8
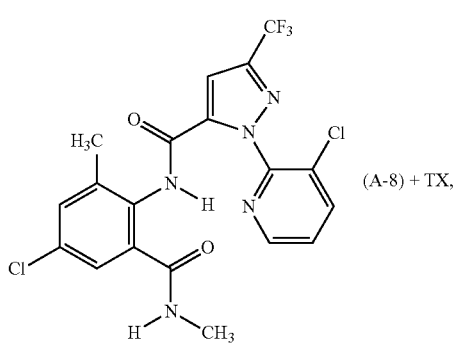
(A-8) + TX,
the formula A-9
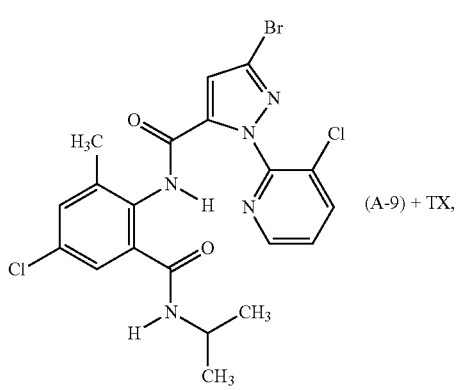
(A-9) + TX,
the formula A-10
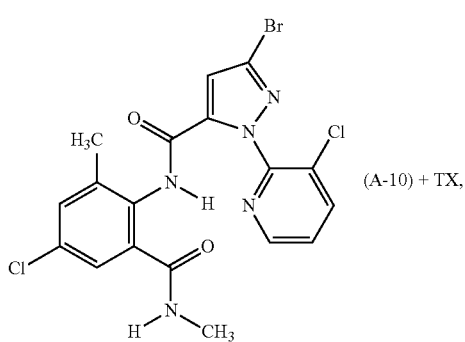
(A-10) + TX,
the formula A-11
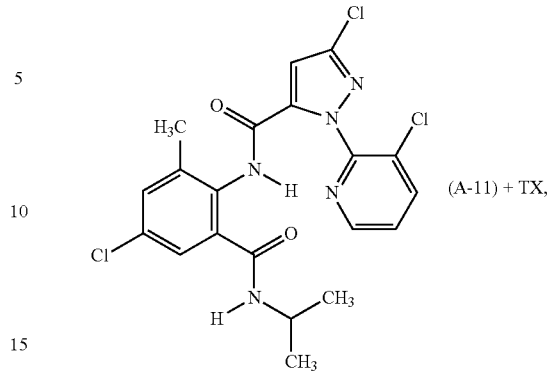
(A-11) + TX,
the formula A-12
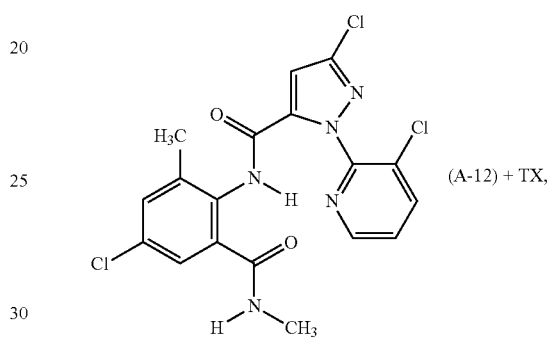
(A-12) + TX,
the formula A-13
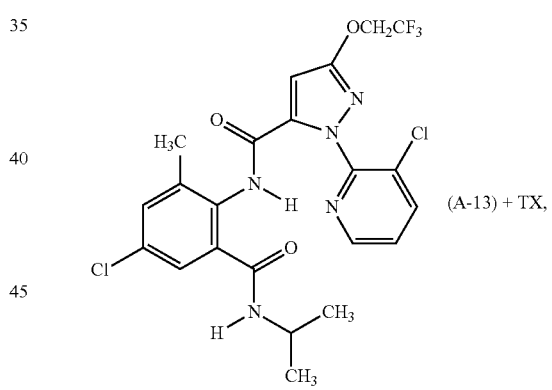
(A-13) + TX,
the formula A-14
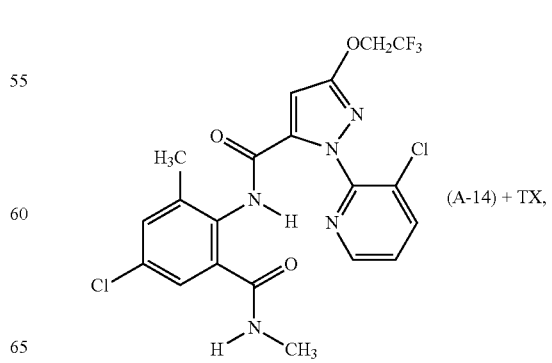
(A-14) + TX, the formula A-15
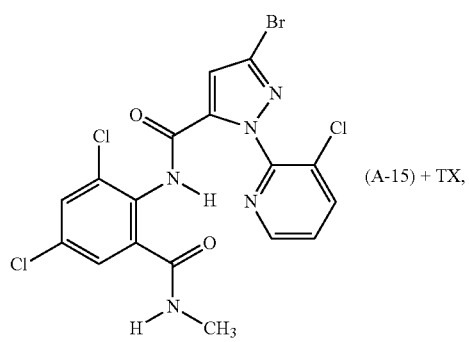
(A-15) + TX,
the formula A-16
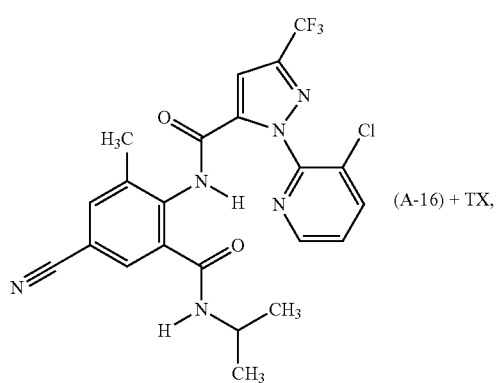
(A-16) + TX,
the formula A-17
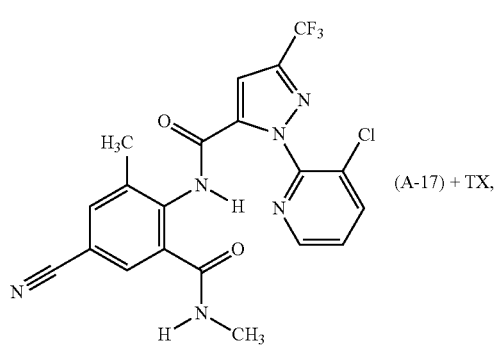
(A-17) + TX,
the formula A-18
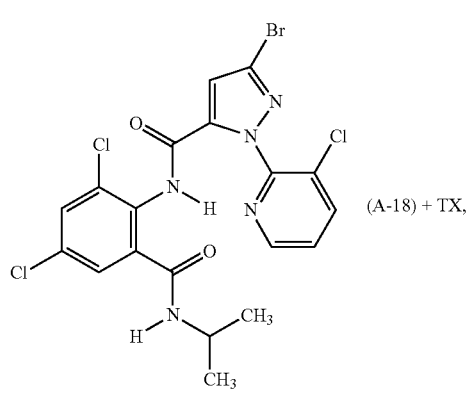
(A-18) + TX,
the formula A-19
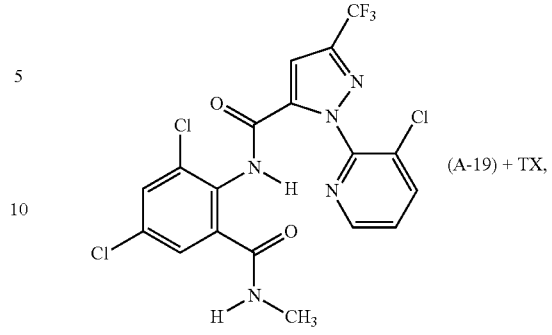
(A-19) + TX,
the formula A-20
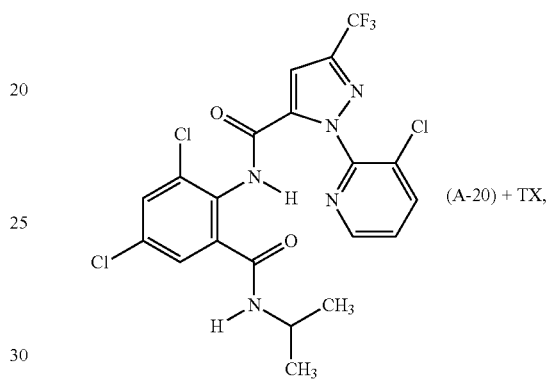
(A-20) + TX,
the formula A-21
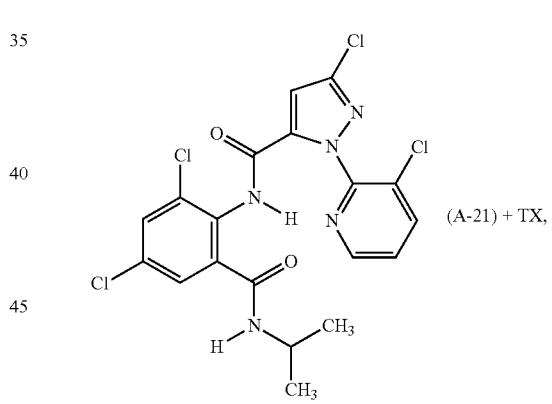
(A-21) + TX,
the formula A-22
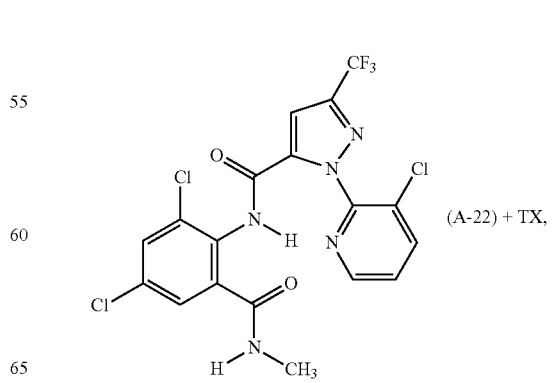
(A-22) + TX, the formula A-23

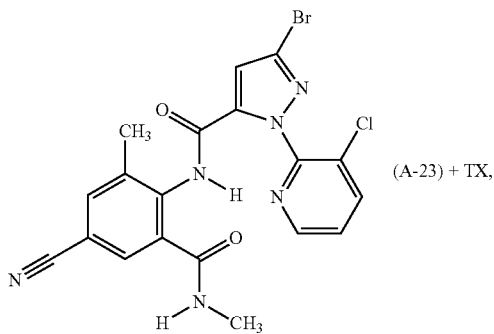

(A-23) + TX, the formula A-24

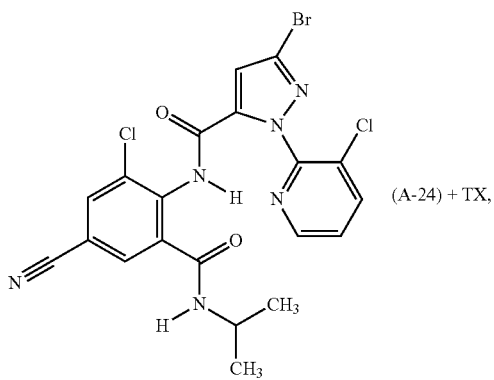

(A-24) + TX, the formula A-25

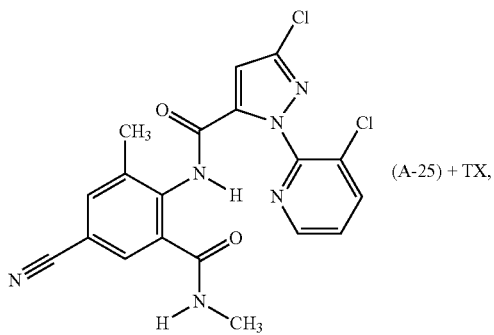

(A-25) + TX, and the formula A-26

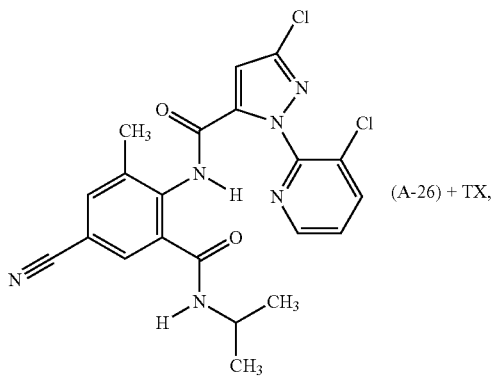

(A-26) + TX, and biologically active compounds selected from the group consisting of Azaconazole (60207-31-0]+TX, Bitertanol [70585-36-3]+TX, Bromuconazole [116255-48-2]+TX, Cyproconazole [94361-06-5]+TX, Difenoconazole [119446-68-3]+TX, Diniconazole [83657-24-3]+TX, Epoxiconazole [106325-08-0]+TX, Fenbuconazole [114369-43-6]+TX, Fluquinconazole [136426-54-5]+TX, Flusilazole [85509-19-9]+TX, Flutriafol [76674-21-0]+TX, Hexaconazole [79983-71-4]+TX, Imazalil [35554-44-0]+TX, Imibenconazole [86598-92-7]+TX, Ipconazole [125225-28-7]+TX, Metconazole [125116-23-6]+TX, Myclobutanil [88671-89-0]+TX, Pefurazoate [101903-30-4]+TX, Penconazole [66246-88-6]+TX, Prothioconazole [178928-70-6]+TX, Pyrifenox [88283-41-4]+TX, Prochloraz [67747-09-5]+TX, Propiconazole [60207-90-1]+TX, Simeconazole [149508-90-7]+TX, Tebuconazole [107534-96-3]+TX, Tetraconazole [112281-77-3]+TX, Triadimefon [43121-43-3]+TX, Triadimenol [55219-65-3]+TX, Triflumizole [99387-89-0]+TX, Triticonazole [131983-72-7]+TX, Ancymidol [12771-68-5]+TX, Fenarimol [60168-88-9]+TX, Nuarimol [63284-71-9]+TX, Bupirimate [41483-43-6]+TX, Dimethirimol [5221-53-4]+TX, Ethirimol [23947-60-6]+TX, Dodemorph [1593-77-7]+TX, Fenpropidine [67306-00-7]+TX, Fenpropimorph [67564-91-4]+TX, Spiroxamine [118134-30-8]+TX, Tridemorph [81412-43-3]+TX, Cyprodinil [121552-61-2]+TX, Mepanipyrim [110235-47-7]+TX, Pyrimethanil [53112-28-0]+TX, Fenpiclonil [74738-17-3]+TX, Fludioxonil [131341-86-1]+TX, Benalaxyl [71626-11-4]+TX, Furalaxyl [57646-30-7]+TX, Metalaxyl [57837-19-1]+TX, R-Metalaxyl [70630-17-0]+TX, Ofurace [58810-48-3]+TX, Oxadixyl [77732-09-3]+TX, Benomyl [17804-35-2]+TX, Carbendazim [10605-21-7]+TX, Debacarb [62732-91-6]+TX, Fuberidazole [3878-19-1]+TX, Thiabendazole [148-79-8]+TX, Chlozolinate [84332-86-5]+TX, Dichlozoline [24201-58-9]+TX, Iprodione [36734-19-7]+TX, Myclozoline [54864-61-8]+TX, Procymidone [32809-16-8]+TX, Vinclozoline [50471-44-8]+TX, Boscalid [188425-85-6]+TX, Carboxin [5234-68-4]+TX, Fenfuram [24691-80-3]+TX, Flutolanil [66332-96-5]+TX, Mepronil [55814-41-0]+TX, Oxycarboxin [5259-88-1]+TX, Penthiopyrad [183675-82-3]+TX, Thifluzamide [130000-40-7]+TX, Guazatine [108173-90-6]+TX, Dodine [2439-10-3] [112-65-2] (freie Base)+TX, Iminoctadine [13516-27-3]+TX, Azoxystrobin [131860-33-8]+TX, Dimoxystrobin [149961-52-4]+TX, enestroburin {Proc. BCPC, Int. Congr., Glasgow, 2003, 1, 93}+TX, Fluoxastrobin [361377-29-9]+TX, Kresoxim-methyl [143390-89-0]+TX, Metominostrobin [133408-50-1]+TX, Trifloxystrobin [141517-21-7]+TX, Orysastrobin [248593-16-0]+TX, Picoxystrobin [117428-22-5]+TX, Pyraclostrobin [175013-18-0]+TX, Ferbam [14484-64-1]+TX, Mancozeb [8018-01-7]+TX, Maneb [12427-38-2]+TX, Metiram [9006-42-2]+TX, Propineb [12071-83-9]+TX, Thiram [137-26-8]+TX, Zineb [12122-67-7]+TX, Ziram [137-30-4]+TX, Captafol [2425-06-1]+TX, Captan [133-06-2]+TX, Dichlofluanid [1085-98-9]+TX, Fluoroimide [41205-21-4]+TX, Folpet [133-07-3]+TX, Tolylfluanid [731-27-1]+TX, Bordeaux Mixture [8011-63-0]+TX, Copperhydroxid [20427-59-2]+TX, Copperoxychlorid [1332-40-7]+TX, Coppersulfat [7758-98-7]+TX, Copperoxid [1317-39-1]+TX, Mancopper [53988-93-5]+TX, Oxine-copper [10380-28-6]+TX, Dinocap [131-72-6]+TX, Nitrothal-isopropyl [10552-74-6]+TX, Edifenphos [17109-49-8]+TX, Iprobenphos [26087-47-8]TX, Isoprothiolane [50512-35-1]+TX, Phosdiphen [36519-00-3]+TX, Pyrazophos [13457-18-6]+TX, Tolclofos-methyl [57018-04-9]+TX, Acibenzolar-S-methyl [135158-54-2]+TX, Anilazine [101-05-3]+TX, Benthiavalicarb [413615-35-7]+TX, Blasticidin-S [2079-00-7]+TX, Chinomethionat [2439-01-2]+TX, Chloroneb [2675-77-6]+TX, Chlorothalonil [1897-45-6]+TX, Cyflufenamid [180409-60-3]+TX, Cymoxanil [57966-95-

7]+TX, Dichlone [117-80-6]+TX, Diclocymet [139920-32-4]+TX, Diclomezine [62865-36-5]+TX, Dicloran [99-30-9]+TX, Diethofencarb [87130-20-9]+TX, Dimethomorph [110488-70-5]+TX, SYP-LI90 (Flumorph) [211867-47-9]+TX, Dithianon [3347-22-6]+TX, Ethaboxam [162650-77-3]+TX, Etridiazole [2593-15-9]+TX, Famoxadone [131807-57-3]+TX, Fenamidone [161326-34-7]+TX, Fenoxanil [115852-48-7]+TX, Fentin [668-34-8]+TX, Ferimzone [89269-64-7]+TX, Fluazinam [79622-59-6]+TX, Fluopicolide [239110-15-7]+TX, Flusulfamide [106917-52-6]+TX, Fenhexamid [126833-17-8]+TX, Fosetyl-aluminium [39148-24-8]+TX, Hymexazol [10004-44-1]+TX, Iprovalicarb [140923-17-7]+TX, IKF-916 (Cyazofamid) [120116-88-3]+TX, Kasugamycin [6980-18-3]+TX, Methasulfocarb [66952-49-6]+TX, Metrafenone [220899-03-6]+TX, Pencycuron [66063-05-6]+TX, Phthalide [27355-22-2]+TX, Polyoxins [11113-80-7]+TX, Probenazole [27605-76-1]+TX, Propamocarb [25606-41-1]+TX, Proquinazid [189278-12-4]+TX, Pyroquilon [57369-32-1]+TX, Quinoxyfen [124495-18-7]+TX, Quintozene [82-68-8]+TX, Schwefel [7704-34-9]+TX, Tiadinil [223580-51-6]+TX, Triazoxide [72459-58-6]+TX, Tricyclazole [41814-78-2]+TX, Triforine [26644-46-2]+TX, Validamycin [37248-47-8]+TX, Zoxamide (RH7281) [156052-68-5]+TX, Mandipropamid [374726-62-2]+TX, the compound of formula F-1

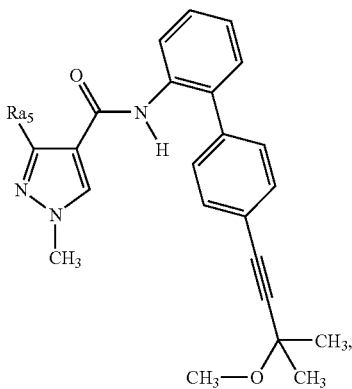

(F-1)

wherein $Ra_5$ is trifluoromethyl or difluoromethyl (WO2004/058723)+TX, the compound of formula F-2

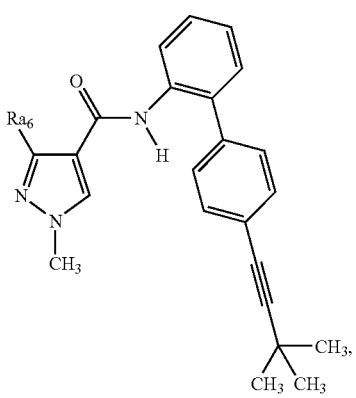

(F-2)

wherein $Ra_6$ is trifluoromethyl or difluoromethyl (WO2004/058723)+TX, the racemic compound of formula F-3 (syn)

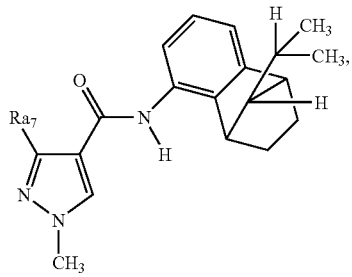

(F-3)

wherein $Ra_7$ is trifluoromethyl or difluoromethyl (WO2004/035589)+TX, the racemic mixture of formula F-4 (anti)

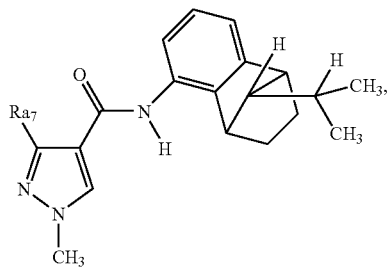

(F-4)

wherein $Ra_7$ is trifluoromethyl or difluoromethyl (WO2004/035589)+TX, the compound of formula F-5

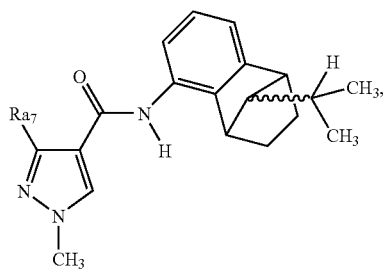

(F-5)

which is an epimeric mixture of racemic compounds of formulae F-3 (syn) and F-4 (anti), wherein the ratio from racemic compounds of formula F-3 (syn) to racemic cmpounds of formula F-4 (anti) is from 1000:1 to 1:1000 and wherein $Ra_7$ is trifluoromethyl or difluoromethyl (WO2004/035589)+TX, the compound of formula F-6

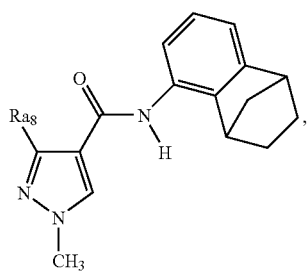

(F-6)

wherein $Ra_8$ is trifluoromethyl or difluoromethyl (WO2004/035589)+TX, the racemic compound of formula F-7 (trans)

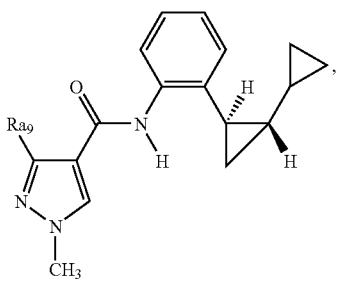
(F-7)

wherein $Ra_9$ is trifluoromethyl or difluoromethyl (WO03/074491)+TX, the racemic compound of formula F-8 (cis)

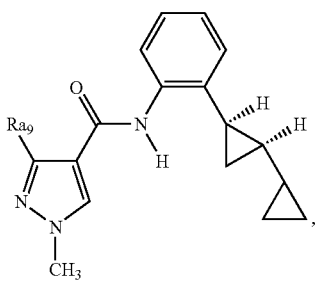
(F-8)

wherein $Ra_9$ is trifluoromethyl or difluoromethyl (WO03/074491)+TX, the compound of formula F-9

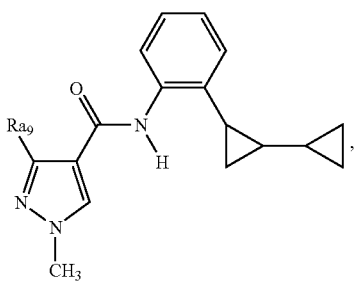
(F-9)

which is a mixture of the racemic compounds of formulae F-7 (trans) and F-8 (cis), wherein the ratio of the racemic compound of formula F-7 (trans) to the racemic compound of formula F-8 (cis) is 2:1 to 100:1; and wherein $Ra_9$ is trifluoromethyl or difluoromethyl (WO03/074491)+TX, the compound of formula F-10

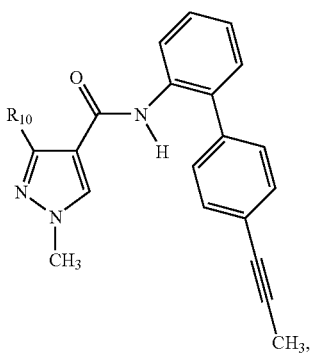
(F-10)

wherein $R_{10}$ is trifluoromethyl or difluoromethyl (WO2004/058723)+TX, the racemic compound of formula F-11 (trans)

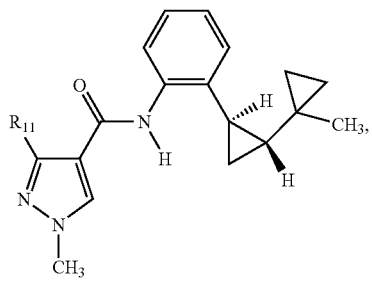
(F-11)

wherein $R_{11}$ is trifluoromethyl or difluoromethyl (WO03/074491)+TX, the racemic compound of formula F-12 (cis)

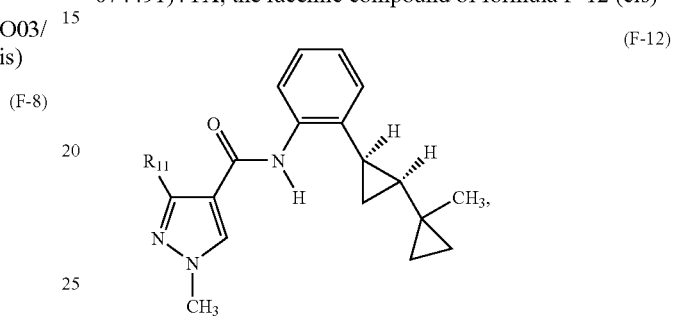
(F-12)

wherein $R_{11}$ is trifluoromethyl or difluoromethyl (WO03/074491)+TX, the compound of formula F-13

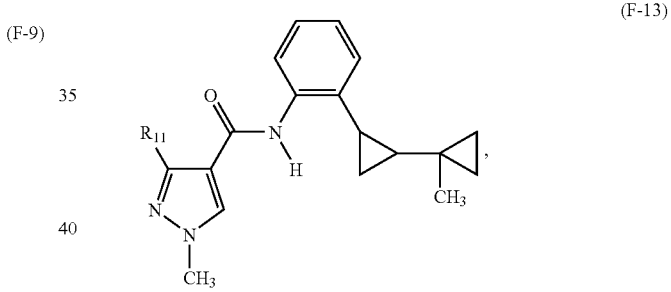
(F-13)

which is a racemic mixture of formulae F-11 (trans) and F-12 (cis), and wherein $R_{11}$ is trifluoromethyl or difluoromethyl (WO 03/074491)+TX, the compound of formula F-14

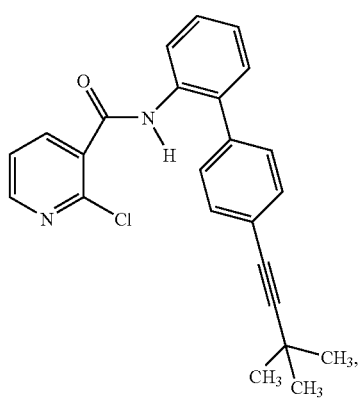
(F-14)

(WO2004/058723)+TX, and the compound of formula F-15

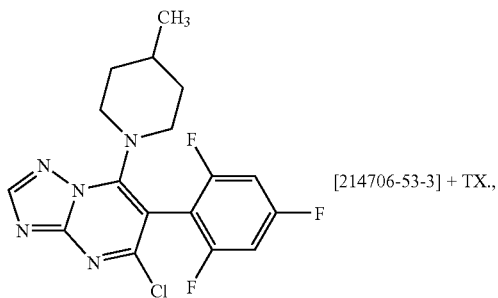

(F-15)

[214706-53-3] + TX.,

The active ingredient mixture of the compounds of formula I selected from tables T1 to T43 with active ingredients described above comprises a compound selected from tables T1 to T43 and an active ingredient as described above preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are understood to include, on the one hand, ratios by weight and also, on other hand, molar ratios.

The mixtures comprising a compound of formula I selected from tables T1 to T43 and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula I selected from tables T1 to T43 and the active ingredients as described above is not essential for working the present invention.

The references in brackets behind the active ingredients, e.g. [3878-19-1] refer to the Chemical Abstracts Registry number. The compouds of formulae A-1 to A-26 are described in WO 03/015518 or in WO 04/067528. The above described mixing partners are known. Where the active ingredients are included in "The Pesticide Manual" [The Pesticide Manual—A World Compendium; Thirteenth Edition; Editor: C. D. S. Tomlin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; *Compendium of Pesticide Common Names*, Copyright © 1995-2004]; for example, the compound "acetoprole" is described under the internet address http://www.alanwood.net/pesticides/acetoprole.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "development code" is used or, if neither one of those designations nor a "common name" is used, an "alternative name" is employed. "CAS Reg. No" means the Chemical Abstracts Registry Number.

Biological Examples (%=per cent by weight, unless otherwise specified)

Example B1

Activity Against *Spodoptera littoralis* (Egyptian Cotton Leaf Worm)

Cotton leaf discs are placed on agar in a 24-well microtiter plate and sprayed with test solutions. After drying, the leaf discs are infested with 5 $L_1$ larvae. The samples are checked for mortality, repellent effect, feeding behaviour, and growth regulation 3 days after treatment (DAT).

In this test, compounds listed in the Tables above show good activity. In particular compounds T13.1.2, T15.1.1, T15.1.91, T13.1.1, T9.1.2 (diastereomer A), T9.1.2 (diastereomer B), T16.1.1, T17.1.2 (diastereomer A), T17.1.2 (diastereomer B), T16.1.91, T13.1.92, T13.1.361, T13.1.391, T13.1.91, T13.1.6, T13.1.96, T44.1.2, T13.1.8, T13.1.23, T13.1.93, T13.1.113, T13.1.21, T13.1.111 have an activity of over 80% at 400 ppm.

Example B2

Activity Against *Heliothis virescens* (Tobacco Budworm)

Eggs (0-24 h old) are placed in 24-well microtiter plate on artificial diet and treated with test solutions by pipetting. After an incubation period of 4 days, samples are checked for egg mortality, larval mortality, and growth regulation.

In this test, compounds listed in the Tables above show good activity. In particular compounds T13.1.2, T15.1.1, T15.1.91, T13.1.1, T9.1.2 (diastereomer A), T9.1.2 (diastereomer B), T16.1.1, T17.1.2 (diastereomer A), T17.1.2 (diastereomer B), T16.1.91, T13.1.92, T13.1.361, T13.1.391, T13.1.91, T13.1.6, T13.1.96, T44.1.2, T13.1.8, T13.1.23, T13.1.93, T13.1.113, T13.1.21, T13.1.111 have an activity of over 80% at 400 ppm.

Example B3

Activity Against *Plutella xvlostella* (Diamond Back Moth)

24-well microtiter plate (MTP) with artificial diet is treated with test solutions by pipetting. After drying, the MTP's are infested with larvae (L2)(10-15 per well). After an incubation period of 5 days, samples are checked for larval mortality, antifeedant and growth regulation. In this test, compounds listed in the Tables above show good activity. In particular compounds T13.1.2, T15.1.1, T15.1.91, T13.1.1, T9.1.2 (diastereomer A), T9.1.2 (diastereomer B), T16.1.1, T17.1.2 (diastereomer A), T17.1.2 (diastereomer B), T16.1.91, T13.1.92, T13.1.361, T13.1.391, T13.1.91, T13.1.6, T13.1.96, T44.1.2, T13.1.8, T13.1.23, T13.1.93, T13.1.113, T13.1.21, T13.1.111 have an activity of over 80% at 400 ppm.

Example B4

Activity Against *Diabrotica balteata* (Corn Root Worm)

24-well microtiter plate (MTP) with artificial diet is treated with test solutions by pipetting. After drying, the MTP's are infested with larvae (L2)(6-10 per well). After an incubation period of 5 days, samples are checked for larval mortality, antifeedant and growth regulation.

In this test, compounds listed in the Tables above show good activity. In particular compounds T13.1.2, T15.1.1, T15.1.91, T13.1.1, T9.1.2 (diastereomer A), T9.1.2 (diastereomer B), T17.1.2 (diastereomer A), T17.1.2 (diastereomer B), T16.1.91, T13.1.92, T13.1.91, T13.1.6, T13.1.96, T44.1.2, T13.1.8, T13.1.23, T13.1.113, T13.1.21, T13.1.111 have an activity of over 80% at 400 ppm.

Example B5

Activity Against *Myzus persicae* (Green Peach Aphid): (Contact)

Sunflower leaf discs are placed on agar in a 24-well microtiter plate and sprayed with test solutions. After drying, the leaf discs are infested with an aphid population of mixed ages. After an incubation period of 6 DAT, samples are checked for mortality and special effects (e.g. phytotoxicity).

In this test, compounds listed in the Tables above show good activity. In particular compounds T13.1.2, T15.1.91, T9.1.2 (diastereomer A), T9.1.2 (diastereomer B), T17.1.2 (diastereomer A), T17.1.2 (diastereomer B), T13.1.92, T13.1.91, T13.1.96, T13.1.21 have an activity of over 80% at 400 ppm.

Example B6

Activity Against *Myzus persicae* (Green Peach Aphid): (Systemic)

Roots of pea seedlings, infested with an aphid population of mixed ages, are placed directly in the test solutions. 6 days after introduction, samples are checked for mortality and special effects on the plant.

In this test, compounds listed in the Tables above show good activity. In particular compounds T13.1.2, T13.1.1, T9.1.2 (diastereomer A), T9.1.2 (diastereomer B), T17.1.2 (diastereomer A), T17.1.2 (diastereomer B), T13.1.92, T13.1.6, T13.1.96, T13.1.93, T13.1.113, T13.1.21 have an activity of over 80% at 400 ppm.

Example B7

Activity Against *Thrips tabaci* (Onion Thrips)

Sunflower leaf discs are placed on agar in a 24-well microtiter plate and sprayed with test solutions. After drying, the leaf discs are infested with a thrips population of mixed ages. After an incubation period of 6 days, samples are checked for mortality and special effects (e.g. phytotoxicity).

In this test, compounds listed in the Tables above show good activity. In particular compounds T13.1.2, T15.1.91, T13.1.1, T9.1.2 (diastereomer A), T9.1.2 (diastereomer B), T17.1.2 (diastereomer A), T17.1.2 (diastereomer B), T16.1.91, T13.1.92, T13.1.91, T13.1.6, T13.1.96, T44.1.2, T13.1.93, T13.1.113, T13.1.21, T13.1.111 have an activity of over 80% at 400 ppm.

Example B8

Activity Against *Tetranychus urticae* (Two-Spotted Spider Mite)

Bean leaf discs on agar in 24-well microtiter plates are sprayed with test solutions. After drying, the leaf discs are infested with mite populations of mixed ages. 8 days later, discs are checked for egg mortality, larval mortality, and adult mortality.

In this test, compounds listed in the Tables above show good activity. In particular compounds T9.1.2 (diastereomer A), T17.1.2 (diastereomer B), T13.1.21 have an activity of over 80% at 400 ppm.

Example B9

Systemic Insecticide Test for *Spodoptera littoralis* (Cotton Leafworm)

Four day old maize seedlings (*Zea mais*, variety Stoneville) are placed individual in vials containing 24 ml water into which the chemical is diluted at 12.5 ppm. Seedlings are allowed to grow for six days. Subsequently leaves are cut and placed in a Petri dish (5 cm diameter), inoculated with twelve to fifteen 1st instar *S. littoralis* larvae and incubated for four days in a growth chamber (25° C., 50% r.h., 18:6 L:D photo period). Number of alive insects are counted and percentage of dead calculated. Tests were conducted with one replicate.

In this test, compounds listed in the Tables above show good activity. In particular compounds T13.1.2, T15.1.1, T13.1.1, T9.1.2 (diastereomer A), T9.1.2 (diastereomer B), T17.1.2 (diastereomer A), T17.1.2 (diastereomer B), T13.1.92, T13.1.361, T13.1.391, T13.1.91, T13.1.6, T13.1.96, T44.1.2, T13.1.8, T13.1.23, T13.1.113 have an activity of over 80%.

Example B10

Activity Against *Cydia pomonella* (Codling Moth)

Standard Cydia diet cubes (1.5 cm width) are pierced with a tooth-pick and are immersed in liquid paraffin (ca. 80° C.). After the paraffin coat has hardened, an aqueous emulsion containing 400 ppm of active ingredient is applied using a De Vilbis sprayer (25 ml, 1 bar). After the spray coating has dried, the cubes are put into plastic containers which are then populated with two freshly hatched *Cydia pomonella* (1$^{st}$ instar). The containers are then closed with a plastic cap. After 14 days incubation at 26° C. and 40-60% relative humidity, the survival rate of the caterpillars as well as their growth regulation is determined.

In this test, compounds listed in the Tables above show good activity. In particular compounds T9.1.2 (diastereomer A), T9.1.2 (diastereomer B), T17.1.2 (diastereomer A), T13.1.92 have an activity of over 80%.

Example B11

Comparison of the Insecticidal Activity of Compounds According to the Invention with the Structurally Most Closely Comparable Compound from the State of the Art (Compound No. 296 Described on Page 108 of WO2003/015518)

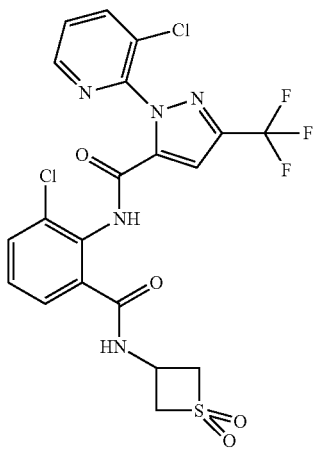

(Compound No. T13.1.391 according to the invention)

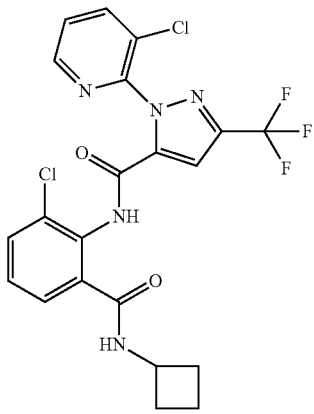

(Compound No. 296 according to the state of the art)

Four day old maize seedlings (*Zea mais*, variety Stoneville) are placed individual in vials containing 24 ml water into which the chemical is diluted at the prescribed concentrations (3 and 0.8 ppm). Seedlings are allowed to grow for six days. Subsequently leaves are cut and placed in a Petri dish (3.5 cm diameter), inoculated with twelve to fifteen 1st instar *S. littoralis* larvae and incubated for four days in a growth chamber (25° C., 50% r.h., 18:6 L:D photo period). Number of alive insects are counted and percentage of dead calculated. Effects on larvae growth were compared to the control and percentage of larvae growth reduction calculated. Tests were conducted with one replicate. Results are shown in Table B11:

TABLE B11

| | Systemic Insecticide Test for *Spodoptera littoralis* (Lepidoptera: Noctuidae): | | |
|---|---|---|---|
| Compound: | Concentration (ppm) | Death rate (%) after 4 days | Larvae growth reduction (% compared to control) |
| Comp. 296 (state of the art) | 3 | 0 | 0 |
| Comp. 296 (state of the art) | 0.8 | 0 | 0 |
| Comp. T13.1.391 (invention) | 3 | 55 | 100 |
| Comp. T13.1.391 (invention) | 0.8 | 10 | 0 |

Table B11 shows that compound No. T13.1.391 according to the invention exerts a substantially better insecticidal action on *Spodoptera littoralis* than the compound from the state of the art. Especially at an application rate of 3 ppm the compound according to the invention is far superior to the compound of the state of the art. This enhanced effect was not to be expected on the basis of the structural similarity of these compounds.

What is claimed is:

1. A compound of formula I

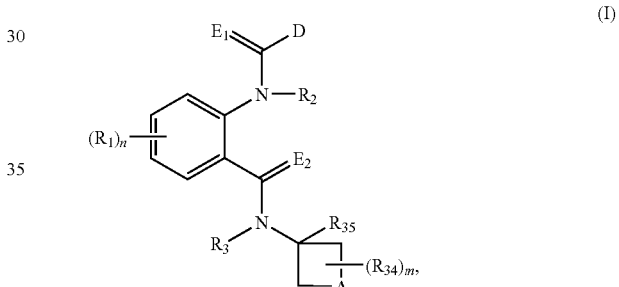

wherein or D is a group

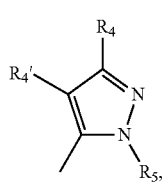

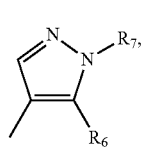

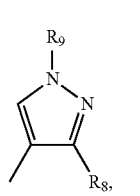

-continued

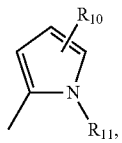
(D4)

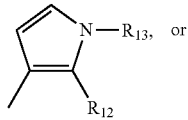
(D5)

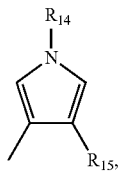
(D6)

R₄, R₄', R₁₀, R₁₇, and R₁₉ independently from each other, are hydrogen, C₁-C₆alkyl, C₃-C₆cycloalkyl, C₁-C₆haloalkyl, halogen, cyano, C₁-C₄alkoxy, C₁-C₄haloalkoxy, C₂-C₄alkoxycarbonyl, C₁-C₄alkylthio, C₁-C₄haloalkylthio, C₁-C₄alkylsulfinyl, C₁-C₄alkylsulfonyl, C₁-C₄haloalkylsulfinyl or C₁-C₄haloalkylsulfonyl;

R₅, R₆, R₈, R₁₁, R₁₂, R₁₅, R₁₆ and R₁₈ independently from each other, are C₁-C₆alkyl, or C₁-C₆alkyl mono-, di- or trisubstituted by halogen, cyano, nitro, hydroxy, C₁-C₄alkoxy, C₂-C₄alkoxycarbonyl, C₁-C₄alkylthio, C₁-C₄alkylsulfinyl, C₁-C₄alkylsulfonyl, C₁-C₄alkylamino, C₂-C₄dialkylamino or C₃-C₆cycloalkylamino; or are phenyl, 2-pyridyl, 3-pyridyl, 4-pyridyl; or are phenyl, 2-pyridyl, 3-pyridyl or 4-pyridyl mono-, di- or trisubstituted by C₁-C₆alkyl, C₃-C₆cycloalkyl, C₁-C₆haloalkyl, halogen, cyano, C₁-C₄alkoxy, C₁-C₄haloalkoxy, C₁-C₄alkylthio, C₁-C₄haloalkylthio, C₁-C₄alkylsulfinyl, C₁-C₄alkylsulfonyl, C₁-C₄haloalkylsulfinyl or C₁-C₄haloalkylsulfonyl;

R₇, R₉, R₁₃ and R₁₄ independently from each other, are hydrogen, C₁-C₆alkyl, C₁-C₆haloalkyl, C₂-C₆alkenyl, C₂-C₆haloalkenyl, C₃-C₆alkenyl or C₃-C₆haloalkenyl;

each R₁ independently is halogen, nitro, cyano, hydroxy, C₁-C₆alkyl, C₂-C₆alkenyl, C₂-C₆alkynyl, C₃-C₆cycloalkyl, C₁-C₆haloalkyl, C₂-C₆haloalkenyl, C₂-C₆haloalkynyl, C₃-C₆halocycloalkyl, C₁-C₄alkoxy, C₁-C₄haloalkoxy, C₁-C₄alkylthio, C₁-C₄haloalkylthio, C₁-C₄haloalkylsulfinyl, C₁-C₄haloalkylsulfonyl, C₁-C₄alkylsulfinyl, C₁-C₄alkylsulfonyl, C₁-C₄alkylamino, C₂-C₄dialkylamino, C₃-C₆cycloalkylamino, C₁-C₆alkyl-C₃-C₆cycloalkylamino, C₂-C₄alkylcarbonyl, C₂-C₆alkoxycarbonyl, C₂-C₆alkylaminocarbonyl, C₃-C₆dialkylaminocarbonyl, C₂-C₆alkoxycarbonyloxy, C₂-C₆alkylaminocarbonyloxy, C₃-C₆dialkylaminocarbonyloxy or C₃-C₆-trialkylsilyl, phenyl, benzyl or phenoxy, or phenyl, benzyl or phenoxy mono-, di- or trisubstituted by halogen, cyano, nitro, halogen, C₁-C₆alkyl, C₂-C₆alkenyl, C₂-C₆alkynyl, C₃-C₆cycloalkyl, C₁-C₆haloalkyl, C₂-C₆haloalkenyl, C₂-C₆haloalkynyl, C₃-C₆halocycloalkyl, C₁-C₄alkoxy, C₁-C₄haloalkoxy, C₁-C₄alkylthio, C₁-C₄haloalkylthio, C₁-C₄alkylsulfinyl, C₁-C₄alkylsulfonyl, C₁-C₄alkylamino, C₂-C₄dialkylamino, C₃-C₆cycloalkylamino, C₁-C₆alkyl-C₃-C₆cycloalkylamino, C₂-C₄alkylcarbonyl, C₂-C₆alkoxycarbonyl, C₂-C₆alkylaminocarbonyl, C₃-C₆dialkylaminocarbonyl, C₂-C₆alkoxycarbonyloxy, C₂-C₆alkylaminocarbonyloxy, C₃-C₆dialkylaminocarbonyloxy or C₃-C₆-trialkylsilyl;

n is 0, 1, 2 or 3;

each of R₂ and R₃, which may be the same or different, represents hydrogen, C₁-C₆alkyl, C₂-C₆alkenyl, C₂-C₆alkynyl or C₃-C₈cycloalkyl; or C₁-C₆alkyl, C₂-C₆alkenyl, C₂-C₆alkynyl or C₃-C₈cycloalkyl substituted by one or more substituents selected from halogen nitro, cyano, hydroxy, C₁-C₄alkoxy, C₁-C₄haloalkoxy, C₁-C₄alkylthio, C₁-C₄haloalkylthio, C₁-C₄alkylsulfinyl, C₁-C₄alkylsulfonyl, C₁-C₄alkylamino, C₂-C₄dialkylamino, C₃-C₆cycloalkylamino and C₁-C₆alkyl-C₃-C₆cycloalkylamino;

each of E₁ and E₂, which may be the same or different, represents oxygen or sulfur;

A is oxygen, sulfur, SO, SO₂, S(O)ₚ=N—R, C=N—OR₃₆, N—R₀, C=O or P(X)ₜ—R₃₃;

R₃₃ is hydrogen, C₁-C₆alkyl, C₂-C₆alkenyl, C₂-C₆alkynyl, C₁-C₆haloalkyl, C₁-C₆alkoxy, hydroxy, C₃-C₆cycloalkyl, C₃-C₆cycloalkyl-C₁-C₆alkyl, benzyl or phenyl; where phenyl and benzyl for their part may be mono- di- or trisubstituted by C₁-C₆alkyl, C₁-C₆haloalkyl, halogen, cyano or nitro; or R₃₃ is O⁻Na⁺, O⁻Li⁺ or O⁻K⁺;

R₃₆ is hydrogen, C₁-C₆alkyl, C₂-C₆alkenyl, C₂-C₆alkynyl, C₁-C₆haloalkyl, C₂-C₆haloalkenyl, C₂-C₆haloalkynyl, C₁-C₆alkoxy-C₁-C₆alkyl, C₁-C₆haloalkoxy-C₁-C₆alkyl or benzyl;

X is oxygen or sulfur;

p is 0 or 1;

t is 0 or 1;

each of R₃₄ and R₃₅, which may be the same or different, represents hydrogen, COOH, halogen, nitro, cyano, hydroxy, C₁-C₆alkyl, C₁-C₆haloalkyl, C₂-C₆alkenyl, C₂-C₆alkynyl, C₂-C₆haloalkenyl, C₂-C₆haloalkynyl, C₁-C₆alkylthio, C₁-C₆alkylsulfinyl, C₁-C₆alkylsulfonyl, C₁-C₆haloalkylthio, C₁-C₆haloalkylsulfinyl, C₁-C₆haloalkylsulfonyl, C₁-C₆alkoxycarbonyl, C₁-C₆alkylcarbonyl, C₃-C₆alkylaminocarbonyl, C₃-C₆dialkylaminocarbonyl, C₁-C₆alkoxy-C₁-C₆alkyl, C₁-C₆haloalkoxy-C₁-C₆alkyl, C₁-C₆alkoxy, C₁-C₆haloalkoxy, C₁-C₆alkylamino, C₂-C₆dialkylamino, C₃-C₆-trialkylsilyl, benzyl or phenyl; where phenyl and benzyl for their part may be mono- di- or trisubstituted by C₁-C₆alkyl, C₁-C₆haloalkyl, C₁-C₆alkoxy, C₁-C₆haloalkoxy, halogen, cyano, hydroxyl or nitro;

m is 0, 1, 2, 3 or 4;

R is hydrogen, C₁-C₆alkyl, C₁-C₆haloalkyl, C₃-C₆cycloalkyl, C₃-C₆halocycloalkyl, C₁-C₆alkylthio, C₁-C₆haloalkylthio, C₁-C₆alkoxy-C₁-C₆alkyl or C₁-C₆haloalkoxy-C₁-C₆alkyl; or R is C₁-C₆alkyl, C₁-C₆haloalkyl, C₃-C₆cycloalkyl, C₃-C₆halocycloalkyl, C₁-C₆alkylthio, C₁-C₆haloalkylthio, C₁-C₆alkoxy-C₁-C₆alkyl or C₁-C₆haloalkoxy-C₁-C₆alkyl substituted by C₁-C₆alkyl, C₁-C₆haloalkyl, C₃-C₆cycloalkyl, C₃-C₆halocycloalkyl, C₁-C₆alkoxy, or $C_1$-$C_6$haloalkoxy; or R is cyano, nitro, —C(O)$R_{26}$, —C(O)O$R_{27}$, —CON$R_{28}R_{29}$, $SO_2R_{30}$ or —P(O)(O$R_{31}$)(O$R_{32}$);

$R_0$ is hydrogen, $C_1$-$C_6$alkyl, $C_1$-$C_6$haloalkyl, $C_3$-$C_6$cycloalkyl, $C_3$-$C_6$halocycloalkyl, $C_1$-$C_6$alkylthio, $C_1$-$C_6$haloalkylthio, $C_1$-$C_6$alkoxy-$C_1$-$C_6$alkyl or $C_1$-$C_6$haloalkoxy-$C_1$-$C_6$alkyl; or $R_0$ is $C_1$-$C_6$alkyl, $C_1$-$C_6$haloalkyl, $C_3$-$C_6$cycloalkyl, $C_3$-$C_6$halocycloalkyl, $C_1$-$C_6$alkylthio, $C_1$-$C_6$haloalkylthio, $C_1$-$C_6$alkoxy-$C_1$-$C_6$alkyl or $C_1$-$C_6$haloalkoxy-$C_1$-$C_6$alkyl substituted by $C_1$-$C_6$alkyl, $C_1$-$C_6$haloalkyl, $C_3$-$C_6$cycloalkyl, $C_3$-$C_6$halocycloalkyl, $C_1$-$C_6$alkoxy, or $C_1$-$C_6$haloalkoxy; or $R_0$ is cyano, nitro, —C(O)$R_{026}$, —C(O)O$R_{027}$, —CON$R_{028}R_{029}$, —$SO_2R_{030}$ or —P(O)(O$R_{031}$)(O$R_{032}$); or $R_0$ is phenyl or benzyl, or phenyl or benzyl mono-, di- or trisubstituted by substituents selected from $C_1$-$C_6$alkyl, $C_3$-$C_6$cycloalkyl, $C_1$-$C_6$haloalkyl, halogen, cyano, $C_1$-$C_4$alkoxy, $C_1$-$C_4$haloalkoxy, $C_1$-$C_4$alkylthio, $C_1$-$C_4$haloalkylthio, $C_1$-$C_4$alkylsulfinyl, $C_1$-$C_4$alkylsulfonyl, $C_1$-$C_4$haloalkylsulfinyl and $C_1$-$C_4$haloalkylsulfonyl;

each of $R_{26}$ and $R_{026}$, which may be the same or different, represents hydrogen, $C_1$-$C_6$alkyl, $C_1$-$C_6$haloalkyl, $C_3$-$C_6$cycloalkyl, $C_3$-$C_6$halocycloalkyl, $C_1$-$C_6$alkylthio, $C_1$-$C_6$haloalkylthio, $C_1$-$C_6$alkoxycarbonyl, $C_1$-$C_6$alkylcarbonyl or $C_1$-$C_6$alkoxy-$C_1$-$C_6$alkyl; or $C_1$-$C_6$alkyl, $C_1$-$C_6$haloalkyl, $C_3$-$C_6$cycloalkyl, $C_3$-$C_6$halocycloalkyl, $C_1$-$C_6$alkylthio, $C_1$-$C_6$haloalkylthio, $C_1$-$C_6$alkoxycarbonyl, $C_1$-$C_6$alkylcarbonyl or $C_1$-$C_6$alkoxy-$C_1$-$C_6$alkyl substituted by $C_1$-$C_6$alkyl, $C_1$-$C_6$haloalkyl, $C_3$-$C_6$cycloalkyl, $C_3$-$C_6$halocycloalkyl, $C_1$-$C_6$alkoxy, or $C_1$-$C_6$haloalkoxy;

each of $R_{27}$, $R_{28}$, $R_{29}$, $R_{30}$, $R_{31}$, $R_{32}$, $R_{027}$, $R_{028}$, $R_{029}$, $R_{030}$, $R_{031}$ and $R_{032}$ which may be the same or different, represents $C_1$-$C_6$alkyl, $C_1$-$C_6$haloalkyl, $C_3$-$C_6$cycloalkyl or $C_3$-$C_6$halocycloalkyl; or $C_1$-$C_6$alkyl, $C_1$-$C_6$haloalkyl, $C_3$-$C_6$cycloalkyl or $C_3$-$C_6$halocycloalkyl substituted by $C_1$-$C_6$alkyl, $C_1$-$C_6$haloalkyl, $C_3$-$C_6$cycloalkyl, $C_3$-$C_6$halocycloalkyl, $C_1$-$C_6$alkoxy or $C_1$-$C_6$haloalkoxy; with the proviso that $E_1$ or $E_2$ is sulfur if A is oxygen, sulfur or N—$R_0$, wherein $R_0$ is hydrogen, $C_1$-$C_3$alkyl, $C_1$-$C_3$haloalkyl, $C_2$-$C_4$alkylcarbonyl, $C_2$-$C_4$haloalkylcarbonyl, $C_2$-$C_4$alkoxycarbonyl or $C_1$-$C_3$alkylsulfonyl;

and agronomically acceptable salts/isomers/diastereomers/enantiomers/tautomers/N-oxides of those compounds said compound.

2. A pesticidal composition, which comprises at least one compound according to claim 1 or, where appropriate, a tautomer thereof, in each case in free form or in agrochemically utilizable salt form, as active ingredient and at least one auxiliary.

3. A composition according to claim 2 for controlling insects or representatives of the order Acarina.

4. A method for controlling pests, which comprises applying a composition according to claim 2 to the pests or their environment.

5. A method according to claim 4 for controlling insects or representatives of the order Acarina.

6. A method according to claim 4 for the protection of plant propagation material from the attack by pests, which comprises treating the propagation material or the site, where the propagation material is planted.

7. Plant propagation material treated in accordance with the method described in claim 6.

8. A compound according to claim 1, wherein D is a group

(D₁)

(D₂)

(D₃)

9. A compound according to claim 1, wherein D is

(D₁)

10. A compound according to claim 9, wherein
$R_4$ and $R_4'$ independently from each other, are hydrogen, $C_1$-$C_6$alkyl, $C_1$-$C_6$haloalkyl, and halogen; and
$R_5$ is $C_1$-$C_6$alkyl; or $C_1$-$C_6$alkyl mono-, di- or trisubstituted by halogen, cyano, nitro, hydroxy; or phenyl, 2-pyridyl, 3-pyridyl, 4-pyridyl; or are phenyl, 2-pyridyl, 3-pyridyl or 4-pyridyl mono-, di- or trisubstituted by $C_1$-$C_6$alkyl, $C_3$-$C_6$cycloalkyl, $C_1$-$C_6$haloalkyl, halogen or cyano.

11. A compound according to claim 10, wherein
$R_4$ and $R_4'$ independently from each other, are hydrogen and $C_1$-$C_6$haloalkyl; and
$R_5$ is 2-pyridyl mono-, di- or trisubstituted by halogen.

12. A compound according to claim 10, wherein A is SO.

13. A compound according to claim 12, wherein
$R_4$ and $R_4'$ independently from each other, are hydrogen, $C_1$-$C_6$alkyl, $C_1$-$C_6$haloalkyl, and halogen;
$R_5$ is $C_1$-$C_6$alkyl; or $C_1$-$C_6$alkyl mono-, di- or trisubstituted by halogen, cyano, nitro, hydroxy; or phenyl, 2-pyridyl, 3-pyridyl, 4-pyridyl; or are phenyl, 2-pyridyl, 3-pyridyl or 4-pyridyl mono-, di- or trisubstituted by $C_1$-$C_6$alkyl, $C_3$-$C_6$cycloalkyl, $C_1$-$C_6$haloalkyl, halogen or cyano;
each $R_1$ independently is halogen, nitro, cyano, hydroxyl or $C_1$-$C_6$alkyl;
n is 0, 1, 2 or 3;
each of $R_2$ and $R_3$ is hydrogen;
each of $E_1$ and $E_2$ is oxygen;
each of $R_{34}$ and $R_{35}$ is hydrogen; and
m is 0, 1, 2, 3 or 4.

14. A compound according to claim 8, wherein D is

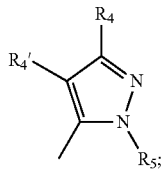
(D₁)

$R_4$ and $R_4'$ independently from each other, are hydrogen, $C_1$-$C_6$alkyl, $C_1$-$C_6$haloalkyl, and halogen;
$R_5$ is $C_1$-$C_6$alkyl; or $C_1$-$C_6$alkyl mono-, di- or trisubstituted by halogen, cyano, nitro, hydroxy; or phenyl, 2-pyridyl, 3-pyridyl, 4-pyridyl; or are phenyl, 2-pyridyl, 3-pyridyl or 4-pyridyl mono-, di- or trisubstituted by $C_1$-$C_6$alkyl, $C_3$-$C_6$cycloalkyl, $C_1$-$C_6$haloalkyl, halogen or cyano;
each $R_1$ independently is halogen, nitro, cyano, hydroxyl or $C_1$-$C_6$alkyl;
n is 0, 1, 2 or 3;
each of $R_2$ and $R_3$ is hydrogen;
each of $E_1$ and $E_2$ is oxygen;
A is oxygen, sulfur, SO, $SO_2$, $S(O)_p$=N—R, C=N—$OR_{36}$, N—$R_0$, C=O or $P(X)_t$—$R_{33}$;
each of $R_{34}$ and $R_{35}$ is hydrogen; and
m is 0, 1, 2, 3 or 4.

15. A compound according to claim 14, wherein
$R_4$ and $R_4'$ independently from each other, are hydrogen and $C_1$-$C_6$haloalkyl;
$R_5$ is 2-pyridyl mono-, di- or trisubstituted by $C_1$-$C_6$alkyl, $C_1$-$C_6$haloalkyl or halogen;
each $R_1$ independently is halogen or $C_1$-$C_6$alkyl;
n is 1, 2 or 3; and
A is SO.

16. A compound according to claim 15, wherein
$R_4$ is trifluoromethyl and $R_4'$ is hydrogen;
$R_5$ is 2-pyridyl mono-substituted by Cl;
n is 2;
each $R_1$ independently is methyl and Cl; and
A is SO.

17. A pesticidal composition, which comprises at least one compound according to claim 8 or, where appropriate, a tautomer thereof, in each case in free form or in agrochemically utilizable salt form, as active ingredient and at least one auxiliary.

18. A pesticidal composition, which comprises at least one compound according to claim 14 or, where appropriate, a tautomer thereof, in each case in free form or in agrochemically utilizable salt form, as active ingredient and at least one auxiliary.

19. A pesticidal composition, which comprises at least one compound according to claim 16 or, where appropriate, a tautomer thereof, in each case in free form or in agrochemically utilizable salt form, as active ingredient and at least one auxiliary.

* * * * *